US011083579B2

(12) United States Patent
Subramanian et al.

(10) Patent No.: US 11,083,579 B2
(45) Date of Patent: *Aug. 10, 2021

(54) TRANSVALVULAR INTRAANULAR BAND AND CHORDAE CUTTING FOR ISCHEMIC AND DILATED CARDIOMYOPATHY

(71) Applicant: Heart Repair Technologies, Inc., Menlo Park, CA (US)

(72) Inventors: Valavanur A. Subramanian, New York, NY (US); Thomas Afzal, Menlo Park, CA (US); Gary Hulme, San Jose, CA (US); Jeffrey Christian, Morgan Hill, CA (US); Michael L. Reo, Redwood City, CA (US)

(73) Assignee: Heart Repair Technologies, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/290,195

(22) Filed: Mar. 1, 2019

(65) Prior Publication Data
US 2019/0298522 A1    Oct. 3, 2019

Related U.S. Application Data

(63) Continuation of application No. 15/482,650, filed on Apr. 7, 2017, now Pat. No. 10,219,903, which is a (Continued)

(51) Int. Cl.
*A61F 2/24*    (2006.01)
(52) U.S. Cl.
CPC ............ *A61F 2/2445* (2013.01); *A61F 2/246* (2013.01); *A61F 2/2454* (2013.01); *A61F 2/2466* (2013.01); *A61F 2/2457* (2013.01)

(58) Field of Classification Search
CPC .... A61F 2/2418; A61F 2/2409; A61F 2/2455; A61F 2/2412; A61F 2220/0016
See application file for complete search history.

(56) References Cited

U.S. PATENT DOCUMENTS 3,789,851 A    2/1974  LeVeen
4,270,143 A    5/1981  Morris
(Continued)

FOREIGN PATENT DOCUMENTS

DE    29618925    1/1997
EP    1 059 893    9/2005
(Continued)

OTHER PUBLICATIONS

U.S. Appl. No. 16/361,694, filed Mar. 22, 2019, Subramanian et al.
(Continued)

*Primary Examiner* — Jennifer Dieterle
*Assistant Examiner* — Tiffany P Shipmon
(74) *Attorney, Agent, or Firm* — Knobbe, Martens, Olson & Bear, LLP

(57) ABSTRACT

Mitral valve prolapse and mitral regurgitation can be treating by implanting in the mitral annulus a transvalvular intraannular band. The band is positioned so that it extends transversely across a coaptive edge formed by the closure of the mitral valve leaflets, to inhibit prolapse into the left atrium. At least one marginal chordae is severed, to permit leaflet closure against the band.

17 Claims, 47 Drawing Sheets

Related U.S. Application Data continuation of application No. 14/622,611, filed on Feb. 13, 2015, now Pat. No. 9,615,925, which is a continuation of application No. 13/630,197, filed on Sep. 28, 2012, now Pat. No. 8,956,406, which is a continuation of application No. 12/579,331, filed on Oct. 14, 2009, now abandoned, which is a continuation-in-part of application No. 12/104,011, filed on Apr. 16, 2008, now Pat. No. 8,262,725.

(56) References Cited

U.S. PATENT DOCUMENTS

| | | |
|---|---|---|
| 5,181,513 A | 1/1993 | Touboul et al. |
| 5,291,889 A | 3/1994 | Kenet et al. |
| 5,360,444 A | 11/1994 | Kusuhara |
| 5,381,791 A | 1/1995 | Qian |
| 5,398,691 A | 3/1995 | Martin et al. |
| 5,400,771 A | 3/1995 | Pirak et al. |
| 5,434,617 A | 7/1995 | Bianchi |
| 5,572,999 A | 11/1996 | Funda et al. |
| 5,593,424 A | 1/1997 | Northrup, III |
| 5,631,970 A | 5/1997 | Hsu |
| 5,631,981 A | 5/1997 | Rao |
| 5,638,819 A | 6/1997 | Manwaring et al. |
| 5,690,108 A | 11/1997 | Chakeres |
| 5,765,561 A | 6/1998 | Chen et al. |
| 5,792,155 A | 8/1998 | Van Cleef |
| 5,906,578 A | 5/1999 | Rajan et al. |
| 6,001,127 A | 12/1999 | Schoon et al. |
| 6,019,791 A | 2/2000 | Wood |
| 6,332,893 B1 | 12/2001 | Mortier et al. |
| 6,419,695 B1 | 7/2002 | Gabbay |
| 6,626,899 B2 | 9/2003 | Houser et al. |
| 6,726,717 B2 | 4/2004 | Alfieri et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,805,710 B2 | 10/2004 | Bolling et al. |
| 6,869,444 B2 | 3/2005 | Gabbay |
| 6,913,608 B2 | 7/2005 | Liddicoat et al. |
| 7,070,618 B2 | 7/2006 | Streeter |
| 7,077,862 B2 | 7/2006 | Vidlund et al. |
| 7,087,064 B1 | 8/2006 | Hyde |
| 7,101,395 B2 | 9/2006 | Tremulis et al. |
| 7,125,421 B2 | 10/2006 | Tremulis et al. |
| 7,160,322 B2 | 1/2007 | Gabbay |
| 7,291,168 B2 | 11/2007 | Macoviak et al. |
| 7,381,220 B2 | 6/2008 | Macoviak et al. |
| 7,455,690 B2 | 11/2008 | Cartledge |
| 7,527,646 B2 | 5/2009 | Randert et al. |
| 7,691,144 B2 | 4/2010 | Chang et al. |
| 7,704,277 B2 | 4/2010 | Zakay et al. |
| 8,262,725 B2 | 9/2012 | Subramanian |
| 8,333,777 B2 | 12/2012 | Schaller et al. |
| 8,348,963 B2 | 1/2013 | Wilson |
| 8,382,829 B1 | 2/2013 | Call et al. |
| 8,480,732 B2 | 7/2013 | Subramanian |
| 8,956,406 B2 | 2/2015 | Subramanian et al. |
| 8,961,597 B2 | 2/2015 | Subramanian et al. |
| 9,168,137 B2 | 10/2015 | Subramanian et al. |
| 9,468,526 B2 | 10/2016 | Subramanian et al. |
| 9,554,903 B2 | 1/2017 | Rowe et al. |
| 9,585,753 B2 | 3/2017 | Subramanian et al. |
| 9,615,925 B2 | 4/2017 | Subramanian et al. |
| 9,968,451 B2 | 5/2018 | Marquez et al. |
| 10,143,553 B2 | 12/2018 | Alon et al. |
| 10,219,903 B2 | 3/2019 | Subramanian et al. |
| 10,238,488 B2 | 3/2019 | Subramanian et al. |
| 10,456,259 B2 | 10/2019 | Subramanian et al. |
| 2002/0065554 A1 | 5/2002 | Streeter |
| 2003/0033009 A1 | 2/2003 | Gabbay |
| 2003/0083742 A1 | 5/2003 | Spence et al. |
| 2003/0093148 A1 | 5/2003 | Bolling et al. |
| 2003/0120340 A1 | 6/2003 | Liska et al. |
| 2003/0199974 A1 | 10/2003 | Lee et al. |
| 2004/0088047 A1 | 5/2004 | Spence et al. |
| 2004/0106989 A1 | 6/2004 | Wilson et al. |
| 2004/0127981 A1 | 7/2004 | Randert et al. |
| 2004/0127982 A1 | 7/2004 | Machold et al. |
| 2004/0138745 A1 | 7/2004 | Macoviak et al. |
| 2004/0152947 A1 | 8/2004 | Schroeder et al. |
| 2004/0162610 A1 | 8/2004 | Liska et al. |
| 2004/0225300 A1 | 11/2004 | Goldfarb et al. |
| 2004/0260393 A1* | 12/2004 | Rahdert ............ A61B 17/00234 623/2.36 |
| 2005/0004665 A1 | 1/2005 | Aklog et al. |
| 2005/0004666 A1 | 1/2005 | Alfieri et al. |
| 2005/0004668 A1* | 1/2005 | Aklog ............... A61F 2/2448 623/2.36 |
| 2005/0010287 A1 | 1/2005 | Macoviak et al. |
| 2005/0038505 A1 | 2/2005 | Shulze et al. |
| 2005/0038508 A1 | 2/2005 | Gabbay |
| 2005/0070999 A1 | 3/2005 | Spence |
| 2005/0075723 A1 | 4/2005 | Schroeder et al. |
| 2005/0107871 A1 | 5/2005 | Realyvasquez et al. |
| 2005/0143811 A1 | 6/2005 | Realyvasquez |
| 2005/0216039 A1 | 9/2005 | Lederman |
| 2005/0256568 A1 | 11/2005 | Lim et al. |
| 2005/0267573 A9 | 12/2005 | Macoviak et al. |
| 2005/0288776 A1 | 12/2005 | Shaoulian et al. |
| 2006/0004443 A1 | 1/2006 | Liddicoat et al. |
| 2006/0020336 A1 | 1/2006 | Liddicoat |
| 2006/0058871 A1 | 3/2006 | Zakay et al. |
| 2006/0069430 A9 | 3/2006 | Randert et al. |
| 2006/0106456 A9 | 5/2006 | Machold et al. |
| 2006/0149368 A1 | 7/2006 | Spence |
| 2006/0161040 A1 | 7/2006 | McCarthy et al. |
| 2006/0195012 A1 | 8/2006 | Mortier et al. |
| 2006/0229708 A1 | 10/2006 | Powell et al. |
| 2006/0247492 A1 | 11/2006 | Streeter |
| 2006/0287661 A1 | 12/2006 | Bolduc et al. |
| 2008/0243245 A1 | 10/2008 | Thambar et al. |
| 2009/0228099 A1 | 9/2009 | Randert et al. |
| 2009/0264995 A1 | 10/2009 | Subramanian |
| 2009/0276055 A1 | 11/2009 | Harris et al. |
| 2010/0076550 A1 | 3/2010 | Subramanian |
| 2010/0121435 A1 | 5/2010 | Subramanian et al. |
| 2010/0121437 A1 | 5/2010 | Subramanian et al. |
| 2010/0131057 A1 | 5/2010 | Subramanian et al. |
| 2012/0101489 A1 | 4/2012 | Bloom et al. |
| 2013/0090724 A1 | 4/2013 | Subramanian et al. |
| 2013/0103140 A1 | 4/2013 | Subramanian et al. |
| 2013/0103142 A1 | 4/2013 | Subramanian et al. |
| 2013/0331930 A1 | 12/2013 | Rowe et al. |
| 2014/0343601 A1 | 11/2014 | Abbott et al. |
| 2015/0223935 A1 | 8/2015 | Subramanian et al. |
| 2015/0257884 A1 | 9/2015 | Subramanian et al. |
| 2015/0366556 A1 | 12/2015 | Khairkhahan et al. |
| 2016/0045314 A1 | 2/2016 | Keren et al. |
| 2016/0143735 A1 | 5/2016 | Subramanian et al. |
| 2016/0324636 A1 | 11/2016 | Rourke et al. |
| 2017/0100245 A1 | 4/2017 | Subramanian et al. |
| 2017/0105839 A1 | 4/2017 | Subramanian et al. |
| 2017/0172741 A1 | 6/2017 | Subramanian et al. |
| 2018/0055638 A1 | 3/2018 | Subramanian et al. |
| 2018/0214270 A1 | 8/2018 | Subramanian et al. |
| 2018/0256153 A1 | 9/2018 | Stone et al. |
| 2019/0298522 A1 | 10/2019 | Subramanian et al. |

FOREIGN PATENT DOCUMENTS

| | | |
|---|---|---|
| GB | 2 254 254 | 7/1992 |
| JP | 05-184611 | 7/1993 |
| JP | 2008-523886 | 7/2008 |
| WO | WO 1998/18411 | 5/1998 |
| WO | WO 2000/60995 | 10/2000 |
| WO | WO 2006/065212 | 6/2006 |
| WO | WO 2007/029252 | 3/2007 |
| WO | WO 2009/129189 | 10/2009 |
| WO | WO 2011/047168 | 4/2011 |
| WO | WO 2011/086401 | 7/2011 |

(56) References Cited

FOREIGN PATENT DOCUMENTS

WO  WO 2017/066480  4/2017
WO  WO 2018/119304  6/2018

OTHER PUBLICATIONS

Final Office Action for U.S. Appl. No. 12/104,011, dated Nov. 15, 2010, in 9 pages.
Final Office Action for U.S. Appl. No. 12/104,011 dated Mar. 30, 2012, in 8 pages.
Non-Final Office Action for U.S. Appl. No. 12/104,011 dated Jul. 12, 2011, in 9 pages.
Non-Final Office Action for U.S. Appl. No. 12/104,011 dated Feb. 23, 2010, in 12 pages.
Non-Final Office Action for U.S. Appl. No. 12/104,011 dated Feb. 3, 2011, in 9 pages.
Notice of Allowance for U.S. Appl. No. 12/104,011 dated Jun. 25, 2012, in 7 pages.
Australian 1st Office Action for App. No. 2009/236358, dated Nov. 26, 2013, in 4 pages.
Australian Notice of Acceptance for Application No. 2009/236358, dated Aug. 17, 2015 in 5 pages.
Australian 1st Office Action for App. No. 2015/261696, dated Feb. 10, 2017, in 5 pages.
Australian 1st Office Action for App. No. 2018200859, dated Sep. 21, 2018, in 3 pages.
Canadian 1st Office Action for Application No. 2,721,450, dated Feb. 1, 2016, in 4 pages.
Canadian Notice of Allowance for Application No. 2,721,450, dated Oct. 27, 2016, in 4 pages.
Canadian Notice of Abandonment for Application No. 2,965,632, dated Oct. 30, 2017, in 1 page.
Non-Final Office Action for U.S. Appl. No. 12/579,330 dated Jul. 13, 2012, in 13 pages.
Non-Final Office Action for U.S. Appl. No. 12/579,331 dated Jun. 26, 2012, in 14 pages.
Non-Final Office Action for U.S. Appl. No. 12/579,364 dated Jul. 18, 2012, in 18 pages.
Non-Final Office Action for U.S. Appl. No. 12/626,272 dated Apr. 29, 2010, in 10 pages.
Non-Final Office Action for U.S. Appl. No. 12/626,272 dated Jan. 6, 2012, in 8 pages.
Final Office Action for U.S. Appl. No. 12/626,272 dated Jan. 24, 2011, in 9 pages.
Notice of Allowance for U.S. Appl. No. 12/626,272 dated May 13, 2013, in 6 pages.
Extended European Search Report for Application No. EP 09732605 dated Jul. 31, 2013, in 6 pages.
EPO Communcaiton for Application No. EP 09732605 dated May 9, 2014, in 4 pages.
EPO Communcaiton for Application No. EP 09732605 dated Aug. 13, 2015, in 4 pages.
EPO Communcaiton for Application No. EP 09732605 dated Aug. 22, 2016, in 4 pages.
EPO Communication for Application No. EP 09732605 dated Jan. 15, 2019, in 4 pages.
Japanese First Office Action for Application No. 2011/505117 dated May 28, 2013, in 4 pages.
Japanese Office Action for Application No. 2011-505117 dated Nov. 26, 2013, in 3 pages.
Japanese Notice of Allowance for Application No. 2011/505117 dated May 26, 2014, in 3 pages.
International Search Report for PCT/US2009/040386 dated Jun. 4, 2009, in 7 pages.
Australian 1st Office Action for Application No. 2010/306762 dated Jan. 9, 2014, in 6 pages.
Australian Notice of Acceptance for Application No. 2010/306762 dated Sep. 29, 2015, in 3 pages.
Canadian 1st Office Action for Application No. 2,777,067 dated Sep. 1, 2016, in 4 pages.
Canadian $2^{nd}$ Office Action for Application No. 2,777,067 dated May 17, 2017, in 4 pages.
Canadian $3^{nd}$ Office Action for Application No. 2,777,067 dated Feb. 11, 2019, in 4 pages.
Canadian Notice of Abandonment for Application No. 2,777,067, dated Nov. 17, 2017, in 1 page.
Office Action for Application No. 10824103.5 dated Nov. 12, 2018, in 4 pages.
Notice of Allowance for U.S. Appl. No. 13/650998 dated Oct. 10, 2014, in 7 pages.
Non-Final Office Action for U.S. Appl. No. 14/628,114 dated Oct. 7, 2015, in 13 pages.
Notice of Allowance for U.S. Appl. No. 13/650998 dated Jun. 15, 2016, in 5 pages.
Non-Final Office Action for U.S. Appl. No. 15/295204 dated Apr. 20, 2018, in 13 pages.
Notice of Allowance for U.S. Appl. No. 15/295204 dated Nov. 6, 2018, in 6 pages.
Extended European Search Report for Application No. 10824103.5 dated Sep. 16, 2013, in 9 pages.
EPO Communication for Application No. EP 10824103 dated Jan. 12, 2017, in 4 pages.
Japanese First Office Action for Application No. 2012-534360 dated Aug. 25, 2014, in 3 pages.
Japanese Notice of Allowance for Application No. 2012-534360 dated Jun. 1, 2015, in 3 pages.
International Search Report and Written Opinion for PCT/US2010/052695 dated Dec. 6, 2010, in 18 pages.
Non-Final Office Action for U.S. Appl. No. 13/630,197 dated Sep. 12, 2013, in 12 pages.
Notice of Allowance for U.S. Appl. No. 13/630,197 dated Oct. 10, 2014, in 5 pages.
Non-Final Office Action for U.S. Appl. No. 14/622,611 dated Nov. 6, 2015, in 9 pages.
Final Office Action for U.S. Appl. No. 14/622,611 dated Jun. 3, 2016, in 6 pages.
Notice of Allowance for U.S. Appl. No. 14/622,611 dated Nov. 9, 2016, in 5 pages.
Non-Final Office Action for U.S. Appl. No. 15/482,650 dated Mar. 27, 2018, in 15 pages.
Notice of Allowance for U.S. Appl. No. 15/482,650 dated Oct. 24, 2018, in 8 pages.
Non-Final Office Action for U.S. Appl. No. 13/653,783 dated Oct. 24, 2014, in 11 pages.
Notice of Allowance for U.S. Appl. No. 13/653,783 dated Aug. 14, 2015, in 5 pages.
Non-Final Office Action for U.S. Appl. No. 14/919,525 dated Apr. 4, 2016, in 5 pages.
Notice of Allowance for U.S. Appl. No. 14/919,525 dated Oct. 17, 2016, in 5 pages.
Non-Final Office Action for U.S. Appl. No. 15/450,971 dated Oct. 20, 2017, in 4 pages.
Final Office Action for U.S. Appl. No. 15/450,971 dated Oct. 5, 2018, in 18 pages.
Non-Final Office Action for U.S. Appl. No. 15/293,111 dated Apr. 25, 2018, in 26 pages.
Notice of Allowance for U.S. Appl. No. 15/293,111 dated Oct. 11, 2018, in 7 pages.
Extended European Search Report for Application No. EP 16856213.0 dated Apr. 9, 2019 in 8 pages.
International Search Report and Written Opinion for PCT/US2016/056900 dated Jan. 12, 2017, in 7 pages.
International Search Report and Written Opinion for PCT/US2017/068011 dated Mar. 29, 2018, in 11 pages.
U.S. Appl. No. 16/655,786, filed Oct. 17, 2019, Subramanian et al.
U.S. Appl. No. 16/786,580, filed Feb. 10, 2020, Subramanian et al.
Non-Final Office Action for U.S. Appl. No. 15/450,971 dated Jul. 18, 2019, in 11 pages.
EPO Communcaiton for Application No. EP 09732605 dated Sep. 3, 2019, in 44 pages.

(56) References Cited

OTHER PUBLICATIONS

Australian Notice of Acceptance for App. No. 2018200859, dated Sep. 9, 2019, in 4 pages.
Non-Final Office Action for U.S. Appl. No. 15/851,577 dated Dec. 9, 2019, in 26 pages.
Non-Final Office Action for U.S. Appl. No. 16/290,195 dated Nov. 18, 2019, in 15 pages.
Notice of Acceptance for Application No. 2,965,632, dated Sep. 25, 2019, in 1 page.
Final Office Action for U.S. Appl. No. 15/450,971 dated Apr. 9, 2020 in 11 pages.
International Search Report and Written Opinion for PCT/US2020/017526 dated May 21, 2020, in 7 pages.
Non-Final Office Action for U.S. Appl. No. 16/361,694 dated Jun. 25, 2020, in 16 pages.

* cited by examiner

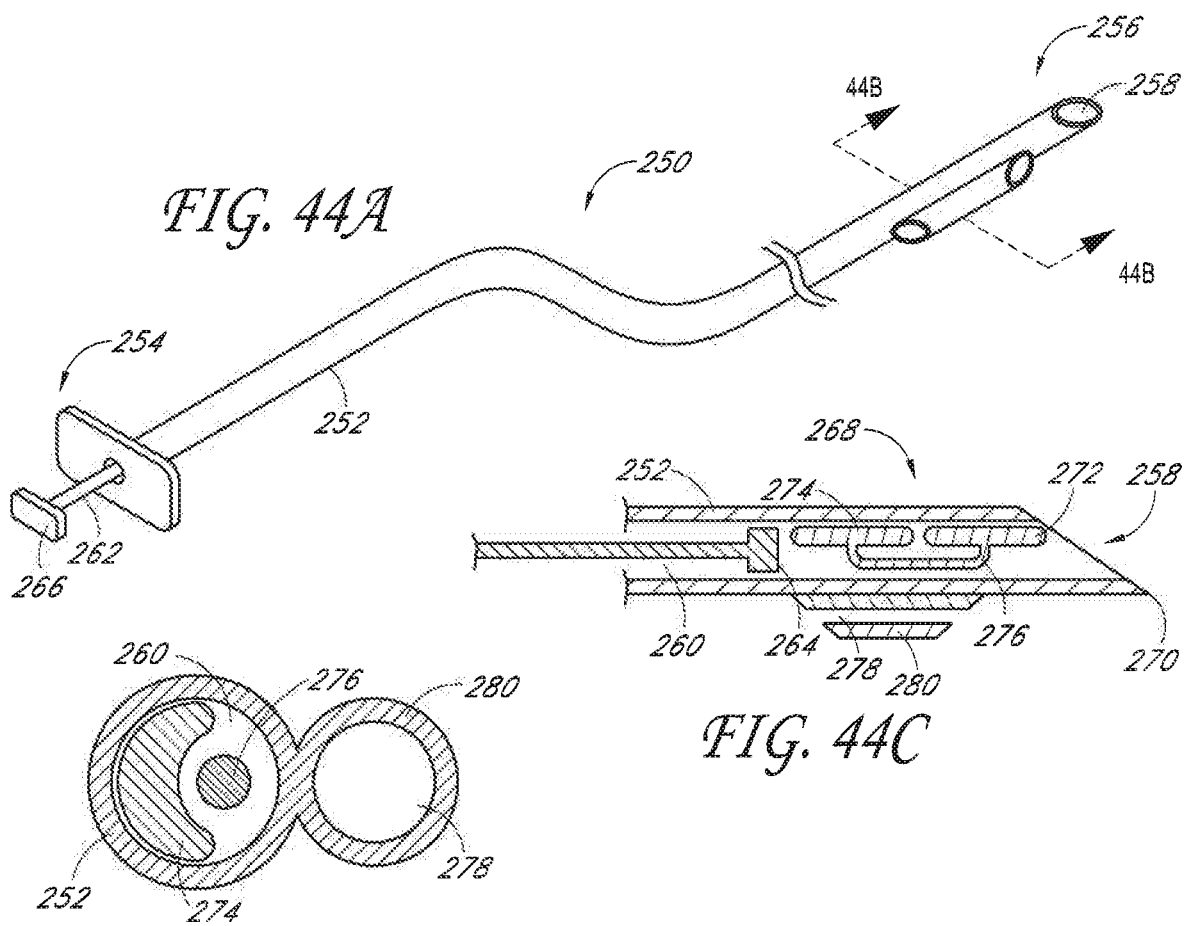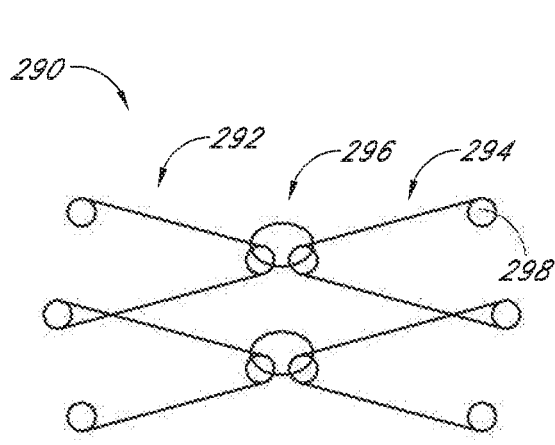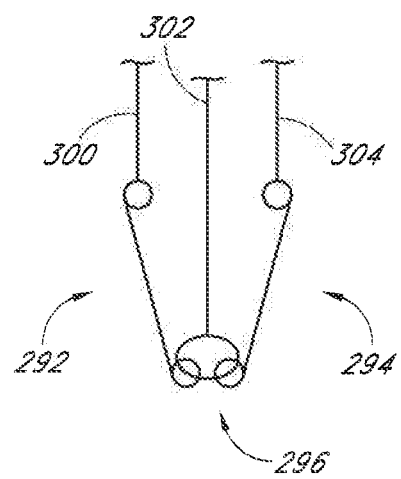

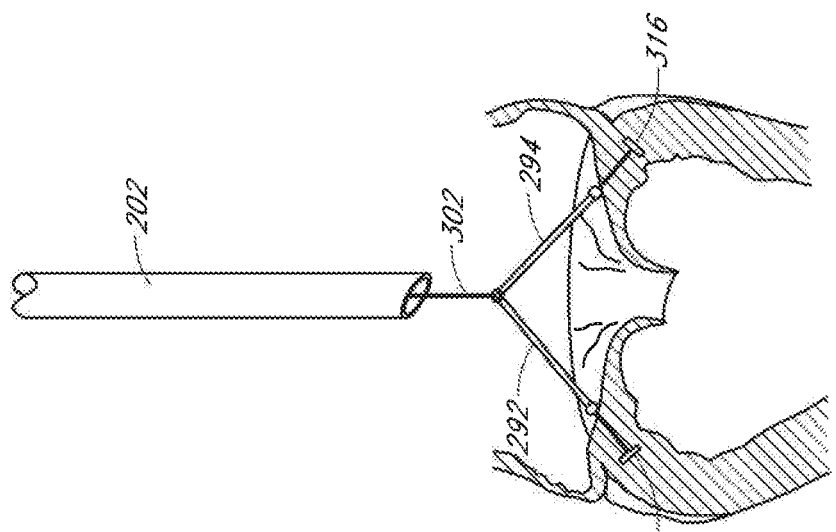
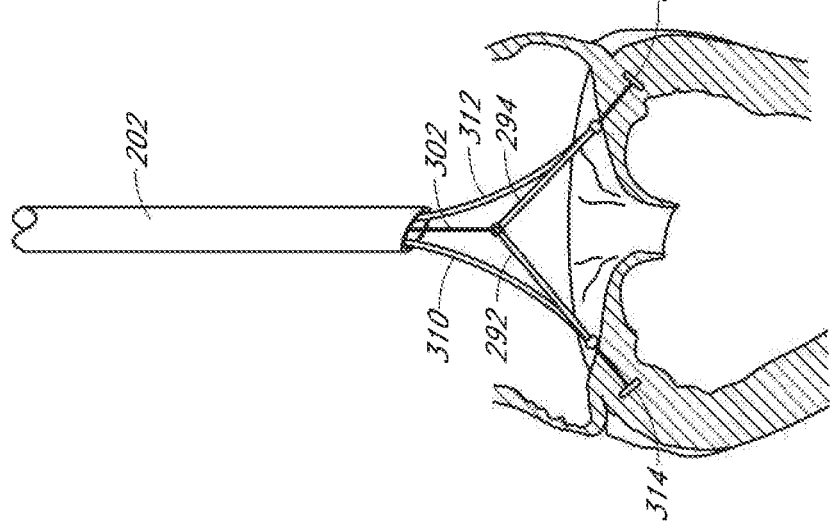
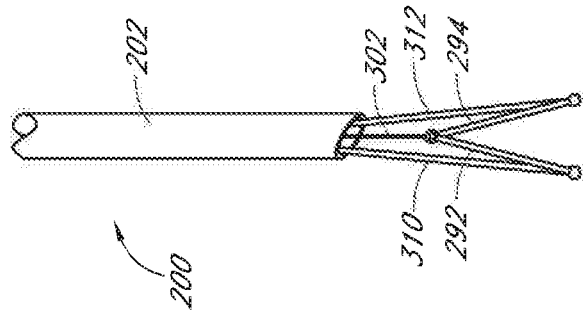
FIG. 47A
FIG. 47B
FIG. 47C

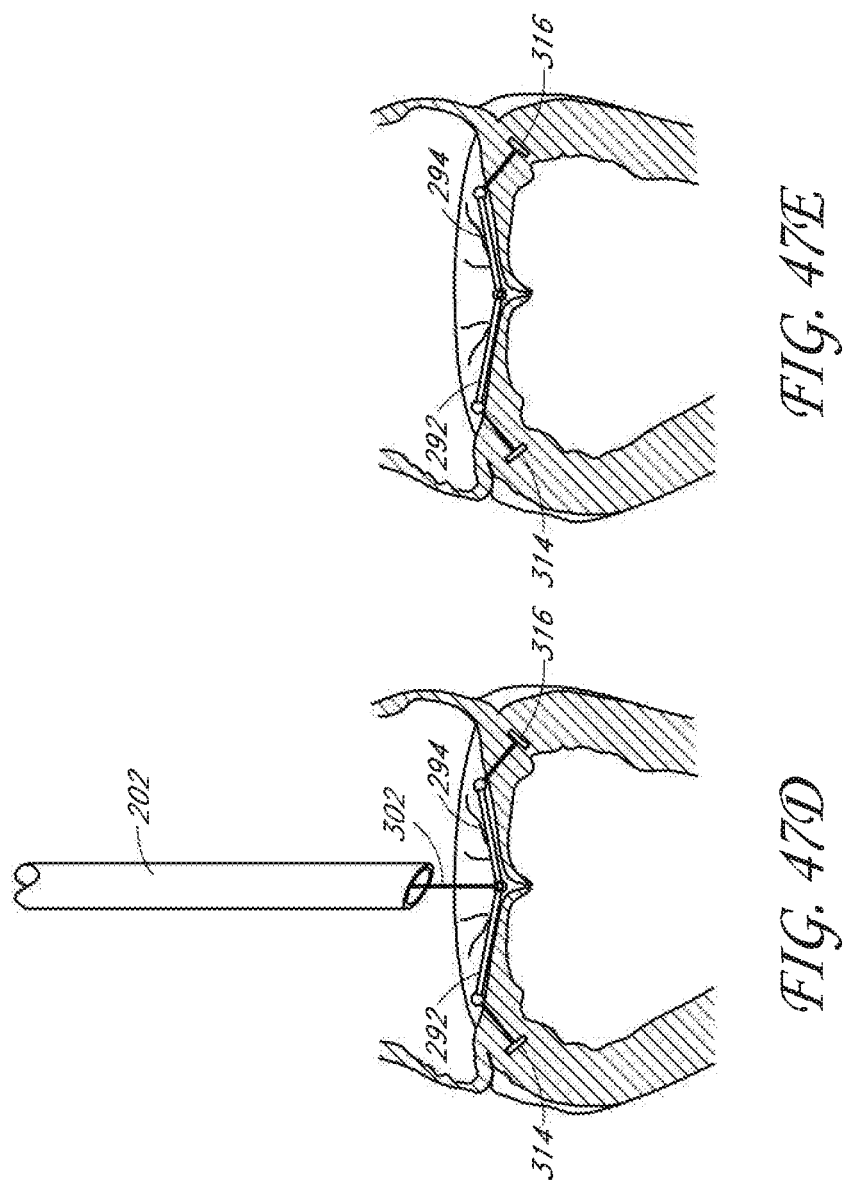

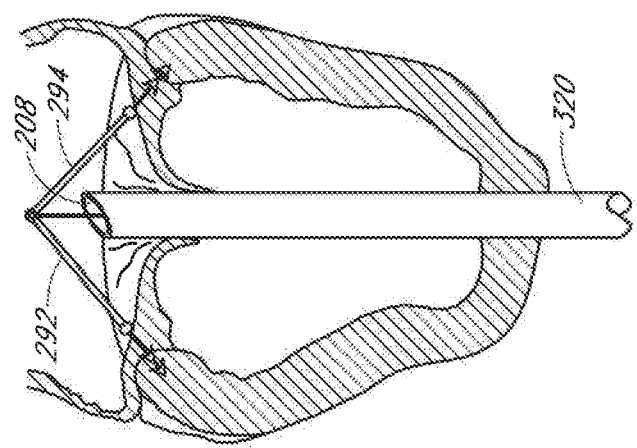
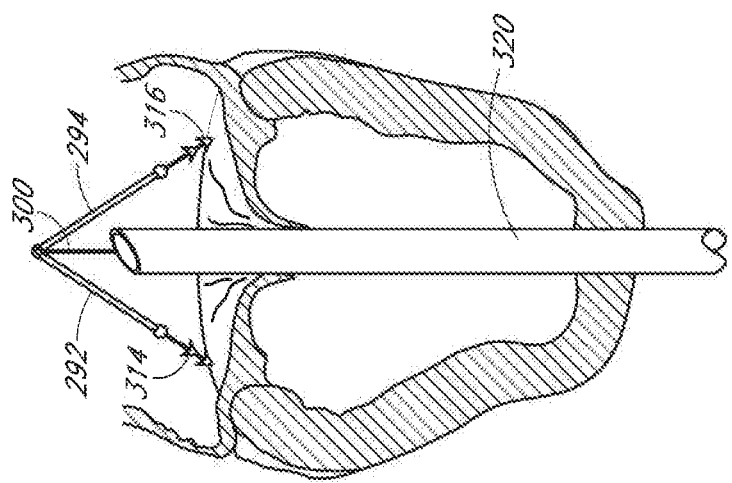

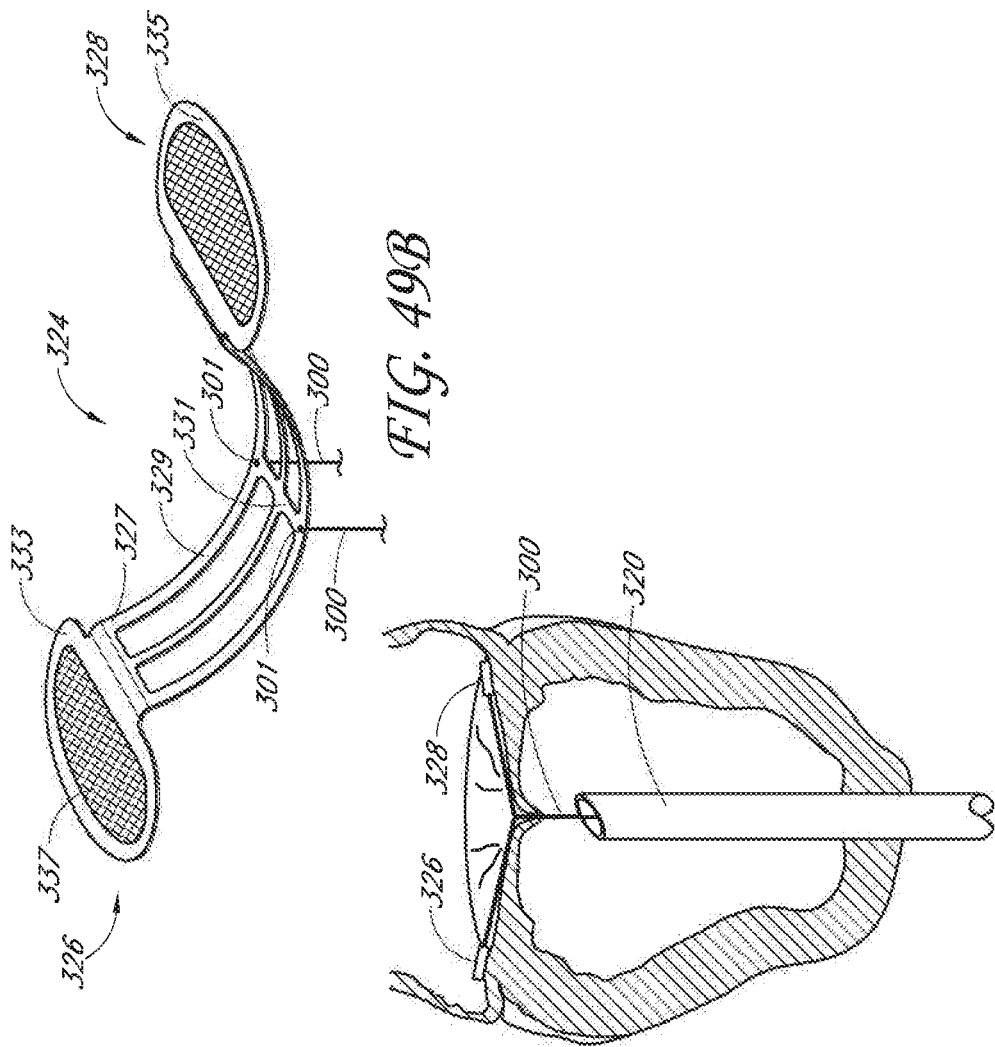
FIG. 49B
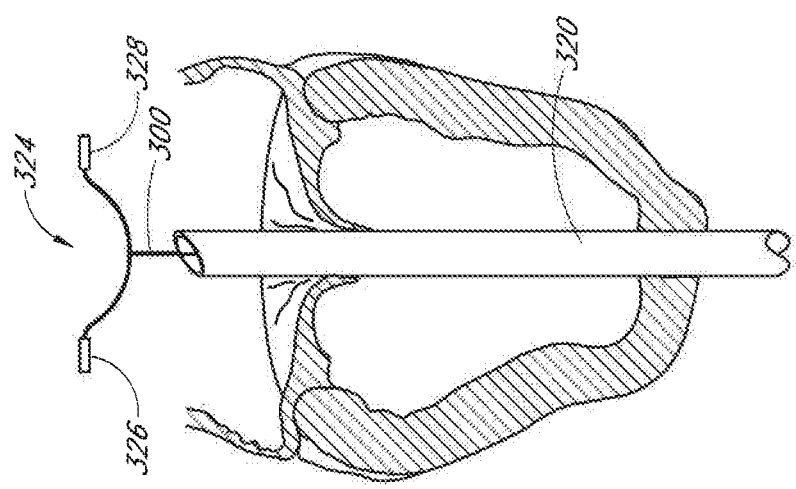
FIG. 49C
FIG. 49A

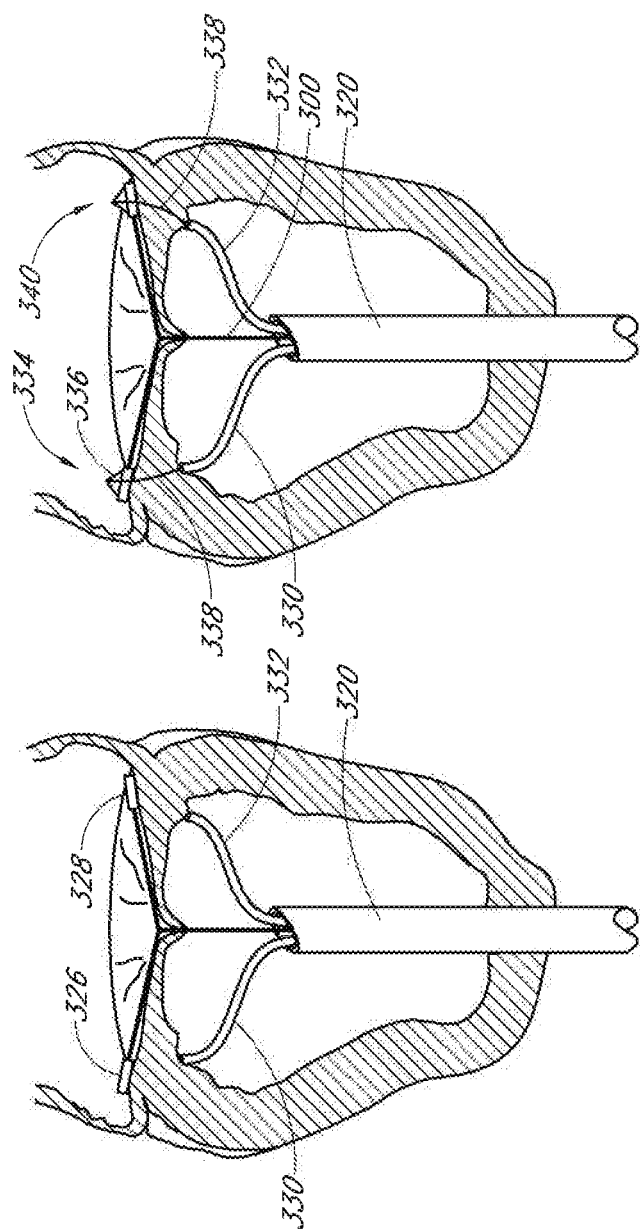

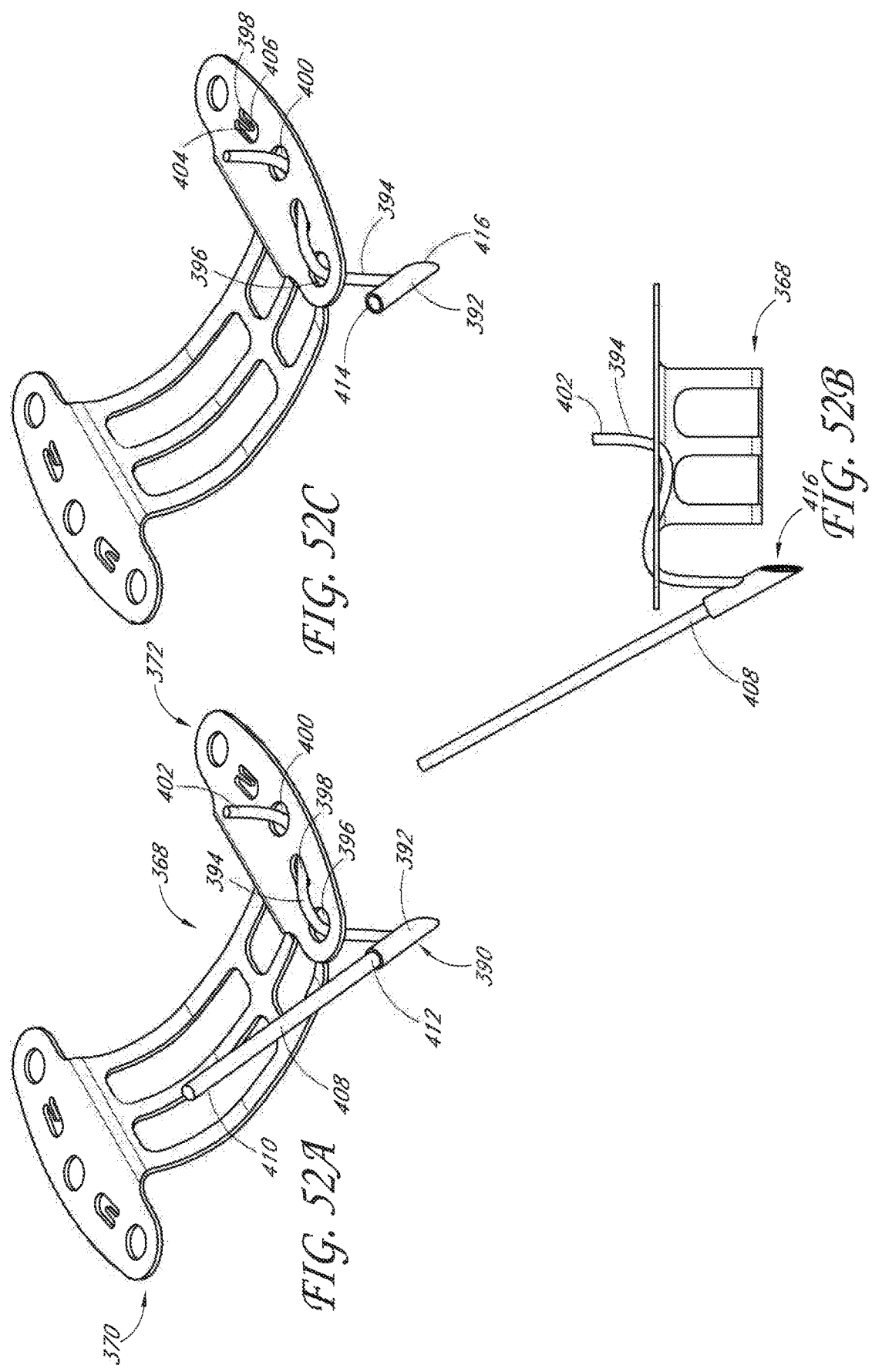

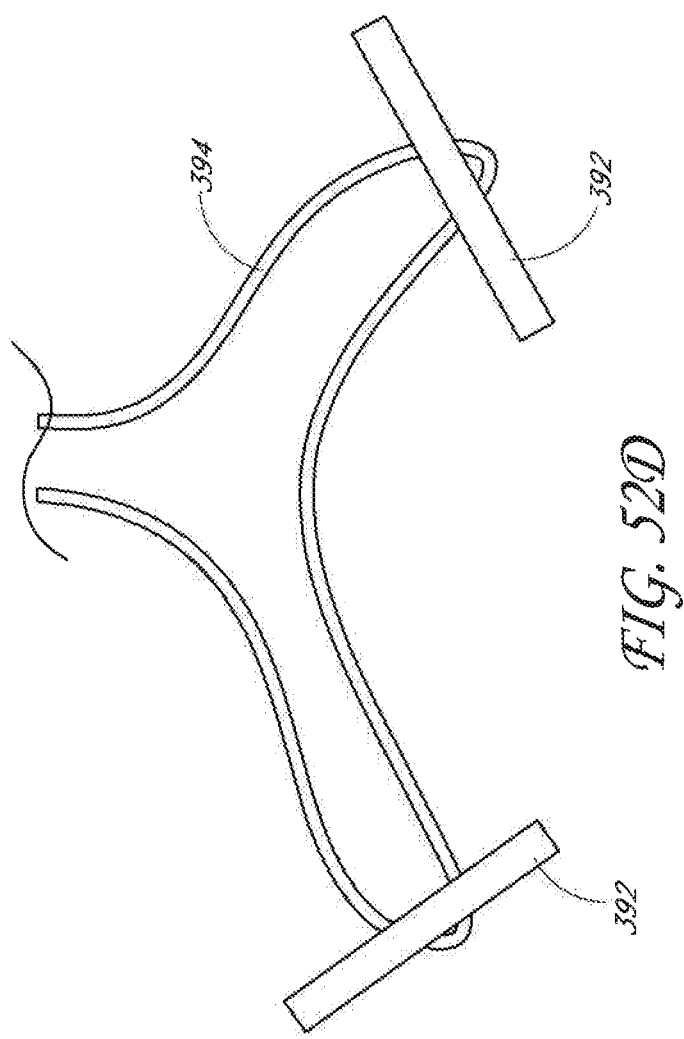

Left, Group mean data for systolic tension of the AMVL anterolateral (ACT) and posteromedial (PCT) strut chordae tendineae during control. Dashed lines indicate ±1 SEM; ED, end diastole (t=0). Right, Group mean data for tension of ACT and PCT with respect to LV pressure during systole.

TRANSVALVULAR INTRAANULAR BAND AND CHORDAE CUTTING FOR ISCHEMIC AND DILATED CARDIOMYOPATHY

CROSS-REFERENCE TO RELATED APPLICATIONS

This application is a continuation of U.S. patent application Ser. No. 15/482,650 filed on Apr. 7, 2017, which is a continuation of U.S. patent application Ser. No. 14/622,611 filed on Feb. 13, 2015, issued as U.S. Pat. No. 9,615,925 on Apr. 11, 2017, which is in turn a continuation of U.S. patent application Ser. No. 13/630,197, filed Sep. 28, 2012, issued as U.S. Pat. No. 8,956,406 on Feb. 17, 2015, which is a continuation of U.S. patent application Ser. No. 12/579,331 filed Oct. 14, 2009, now abandoned, which is a continuation-in-part of U.S. patent application Ser. No. 12/104,011 filed Apr. 16, 2008, issued as U.S. Pat. No. 8,262,725 on Sep. 11, 2012. The disclosure of each of these foregoing applications is incorporated by reference herein in their entireties.

BACKGROUND OF THE INVENTION

Field of the Invention

Embodiments of the present invention relate generally to treatment of mitral or tricuspid valve prolapse and mitral regurgitation, and more specifically, relate to the use of a transvalvular band to treat mitral valve prolapse and mitral regurgitation.

Description of the Related Art

The heart is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenated ("arterial") blood from the lungs through the pulmonary veins and pumps it into the aorta for distribution to the body.

The heart has four chambers, two on each side—the right and left atria, and the right and left ventricles. The atria are the blood-receiving chambers, which pump blood into the ventricles. A wall composed of membranous and muscular parts, called the interatrial septum, separates the right and left atria. The ventricles are the blood-discharging chambers. A wall composed of membranous and muscular parts, called the interventricular septum, separates the right and left ventricles.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

Various disease processes can impair the proper functioning of one or more of these valves. These include degenerative processes (e.g., Barlow's Disease, fibroelastic deficiency), inflammatory processes (e.g., Rheumatic Heart Disease) and infectious processes (e.g., endocarditis). In addition, damage to the ventricle from prior heart attacks (i.e., myocardial infarction secondary to coronary artery disease) or other heart diseases (e.g., cardiomyopathy) can distort the valve's geometry causing it to dysfunction.

The mitral valve is comprised of an anterior leaflet and a posterior leaflet. The bases of the leaflets are fixed to a circumferential partly fibrous structure, the annulus, preventing dehiscence of the valve. A subvalvular apparatus of chordae and papillary muscles prevents the valve from prolapsing into the left atrium. Mitral valve disease can be expressed as a complex variety of pathological lesions of either valve or subvalvular structures, but can also be related to the functional status of the valve. Functionally the mitral valve disease can be categorized into two anomalies, increased leaflet motion i.e. leaflet prolapse leading to regurgitation, or diminished leaflet motion i.e. restricted leaflet motion leading to obstruction and/or regurgitation of blood flow.

Leaflet prolapse is defined as when a portion of the leaflet overrides the plane of the orifice during ventricular contraction. The mitral regurgitation can also develop secondary to alteration in the annular ventricular apparatus and altered ventricular geometry, followed by incomplete leaflet coaptation. In ischemic heart failure this can be attributed to papillary or lateral wall muscle dysfunction, and in non-ischemic heart failure it can be ascribed to annular dilation and chordal tethering, all as a result of dysfunctional remodeling.

The predominant cause of dysfunction of the mitral valve is regurgitation which produces an ineffective cardiac pump function resulting in several deleterious conditions such as ventricular and atrial enlargement, pulmonary hypertension and heart-failure and ultimately death.

The main objective for the surgical correction is to restore normal function and not necessarily anatomical correction. This is accomplished by replacing the valve or by reconstructing the valve. Both of the procedures require the use of cardiopulmonary bypass and is a major surgical operation carrying a non-negligible early morbidity and mortality risk, and a postoperative rehabilitation for months with substantial postoperative pain. Historically, the surgical approach to patients with functional mitral regurgitation was mitral valve replacement, however with certain adverse consequences such as thromboembolic complications, the need for anti-coagulation, insufficient durability of the valve, loss of ventricular function and geometry.

Reconstruction of the mitral valve is therefore the preferred treatment for the correction of mitral valve regurgitation and typically consists of a quadrangular resection of the posterior valve (valvuloplasty) in combination with a reduction of the mitral valve annulus (annuloplasty) by the means of suturing a ring onto the annulus. These procedures are surgically demanding and require a bloodless and well-exposed operating field for an optimal surgical result. The technique has virtually not been changed for more than three decades.

More recently, prolapse of the valve has been repaired by anchoring the free edge of the prolapsing leaflet to the corresponding free edge of the opposing leaflet and thereby restoring apposition but not necessarily coaptation. In this procedure a ring annuloplasty is also required to attain complete coaptation.

This method commonly referred to as an edge-to-edge or "Alfieri" repair also has certain drawbacks such as the creation of a double orifice valve and thereby reducing the effective orifice area. Several less invasive approaches related to the edge-to-edge technique has been suggested, for repairing mitral valve regurgitation by placing a clip through a catheter to suture the valve edges. However, it still remains to conduct an annuloplasty procedure, which has not yet been resolved by a catheter technique and therefore is to be performed by conventional surgery, which makes the method impractical.

Notwithstanding the presence of a variety of presently available surgical techniques and promising catheter based procedures for the future, there remains a need for a simple but effective device and corresponding surgical, minimally invasive or transvascular procedure to reduce mitral valve regurgitation.

SUMMARY OF THE INVENTION

There is provided in accordance with one aspect of the present invention, a method of treating ischemic or dilated cardiomyopathy. The method comprises the steps of providing an intraannular transvalvular band, dimensioned for attachment within the plane of the mitral valve annulus. The band is attached within the plane of the annulus, such that a portion of the band extends into the ventricular side of the plane, to support the leaflets and elevate the position of the coaptive edges in the direction of the ventricle during valve closure. At least one marginal chordae is manipulated, to permit leaflet coaption.

Depending upon the desired clinical outcome, at least two or three or four or more marginal chordae are manipulated to permit leaflet coaption. Manipulation of the marginal chordae may comprise severing the chordae, such as by a mechanical cutting instrument, or any of a variety of tissue severing energy modalities including radio frequency, microwave, ultrasound, laser, cryoablation or other cutting modality known in the art.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 44A is a side elevational perspective view of an anchor deployment catheter in accordance with the present invention.

FIG. 44B is a cross sectional view taken along the line 44B-44B of FIG. 44A.

FIG. 44C is a cross sectional side view of the anchor deployment catheter of FIG. 44A.

FIG. 45A is a schematic plan view of a self-expandable transvalvular band in accordance with the present invention.

FIG. 45B is a side elevational view of the transvalvular band of FIG. 45A shown in a reduced crossing profile (folded) configuration, and attached to three control wires.

FIG. 47A is a side elevational view of the distal end of a deployment catheter, having an implant partially deployed therefrom.

FIG. 47B is a schematic view of the catheter and implant of FIG. 47A, during implantation at the mitral valve.

FIG. 47C is a schematic view as in FIG. 47B, with the tissue anchor deployment guides removed.

FIG. 47D is a schematic view as in FIG. 47C, with the implant configured to move coaption earlier in the cardiac cycle.

FIG. 47E is a schematic view of the implant of FIG. 47D, with the deployment catheter removed.

FIG. 48A is schematic cross sectional view of a transapical deployment device positioned across the mitral valve.

FIG. 48B is a schematic view of the device of FIG. 48A, with tissue anchors engaged at the mitral valve annulus.

FIGS. 49A through 49G illustrate an implantation sequence for a transvalvular band at the mitral valve, via a transapical access.

FIGS. 52A through 52C illustrate a transvalvular band, with a "t-tag" deployment system and suture tensioning feature.

FIG. 52D illustrates an embodiment of a plurality of tissue anchors looped together on a suture.

DETAILED DESCRIPTION OF THE PREFERRED EMBODIMENT

Figure 1:
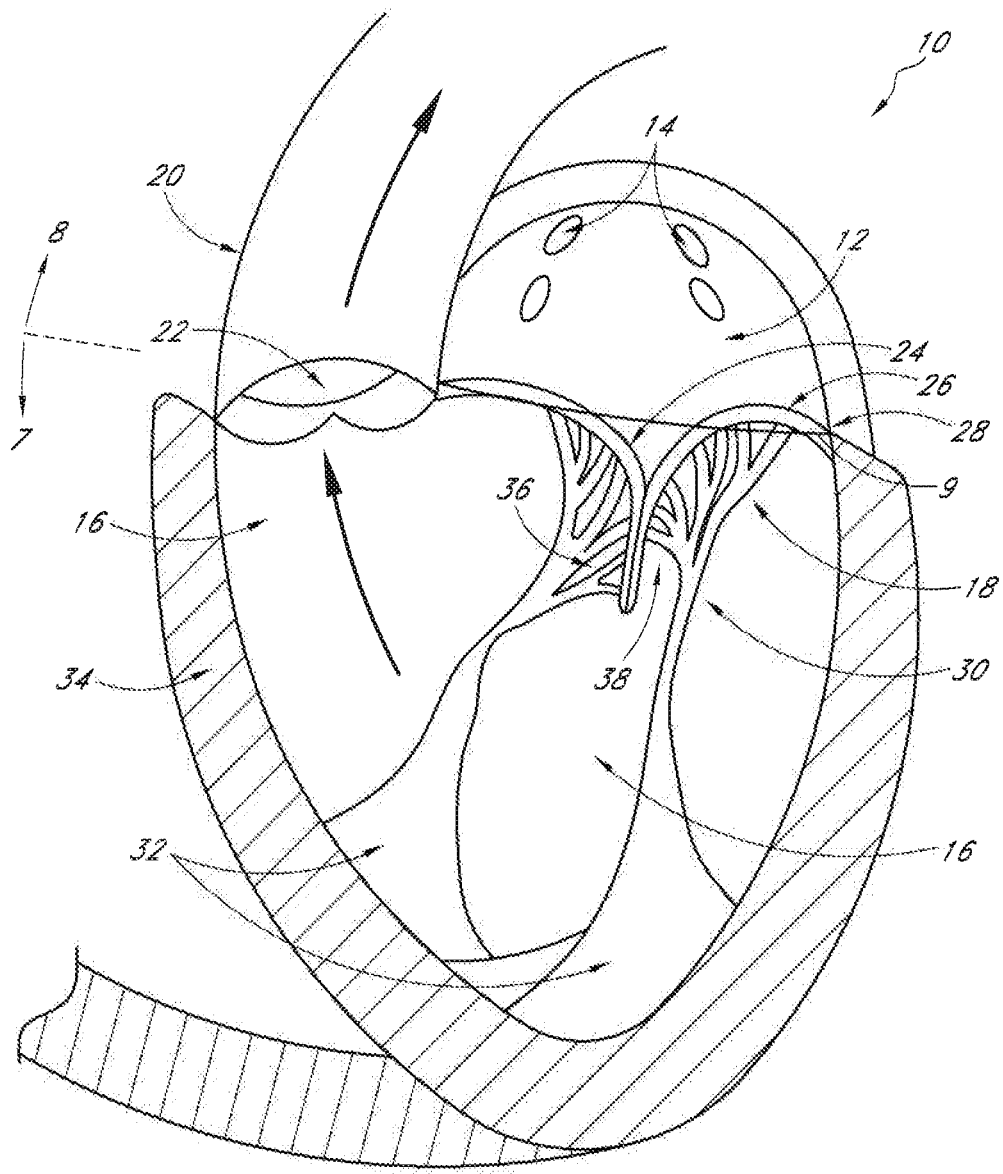
FIG. 1 is a simplified cross-sectional view of the heart with a normal mitral valve during systole. The intraaannular plane is illustrated relative to supraannular and infrannular.

FIG. 1 illustrates a cross-sectional view of the heart 10 with a normal mitral valve 18 in systole. As illustrated, the heart 10 comprises the left atrium 12 which receives oxygenated blood from the pulmonary veins 14 and the left ventricle 16 which receives blood from the left atrium 12. The mitral valve 18 is located between the left atrium 12 and left ventricle 16 and functions to regulate the flow of blood from the left atrium 12 to the left ventricle 16. During ventricular diastole, the mitral valve 18 is open which allows blood to fill the left ventricle 16. During ventricular systole, the left ventricle 16 contracts, which results in an increase in pressure inside the left ventricle 16. The mitral valve 18 closes when the pressure inside the left ventricle 16 increases above the pressure within the left atrium 12. The pressure within the left ventricle 16 continues increasing until the pressure within the left ventricle 16 exceeds the pressure within the aorta 20, which causes the aortic valve 22 to open and blood to be ejected from the left ventricle and into the aorta 20.

The mitral valve 18 comprises an anterior leaflet 24 and a posterior leaflet 26 that have base portions that are attached to a fibrous ring called the mitral valve annulus 28. Each of the leaflets 24 and 26 has respective free edges 36 and 38. Attached to the ventricular side of the leaflets 24 and 26 are relatively inelastic chordae tendineae 30. The chordae tendineae 30 are anchored to papillary muscles 32 that extend from the intraventricular septum 34. The chordae tendineae 30 and papillary muscle 32 function to prevent the leaflets 24 and 26 from prolapsing and enable proper coaptation of the leaflets 24 and 26 during mitral valve 18 closure. Also shown schematically is line 9 through the valve annulus 28 representing the intraannular plane. Arrow 8 points supraannularly, toward the left atrium 12, while arrow 7 points infraannularly, toward the left ventricle 16.

Figure 2:
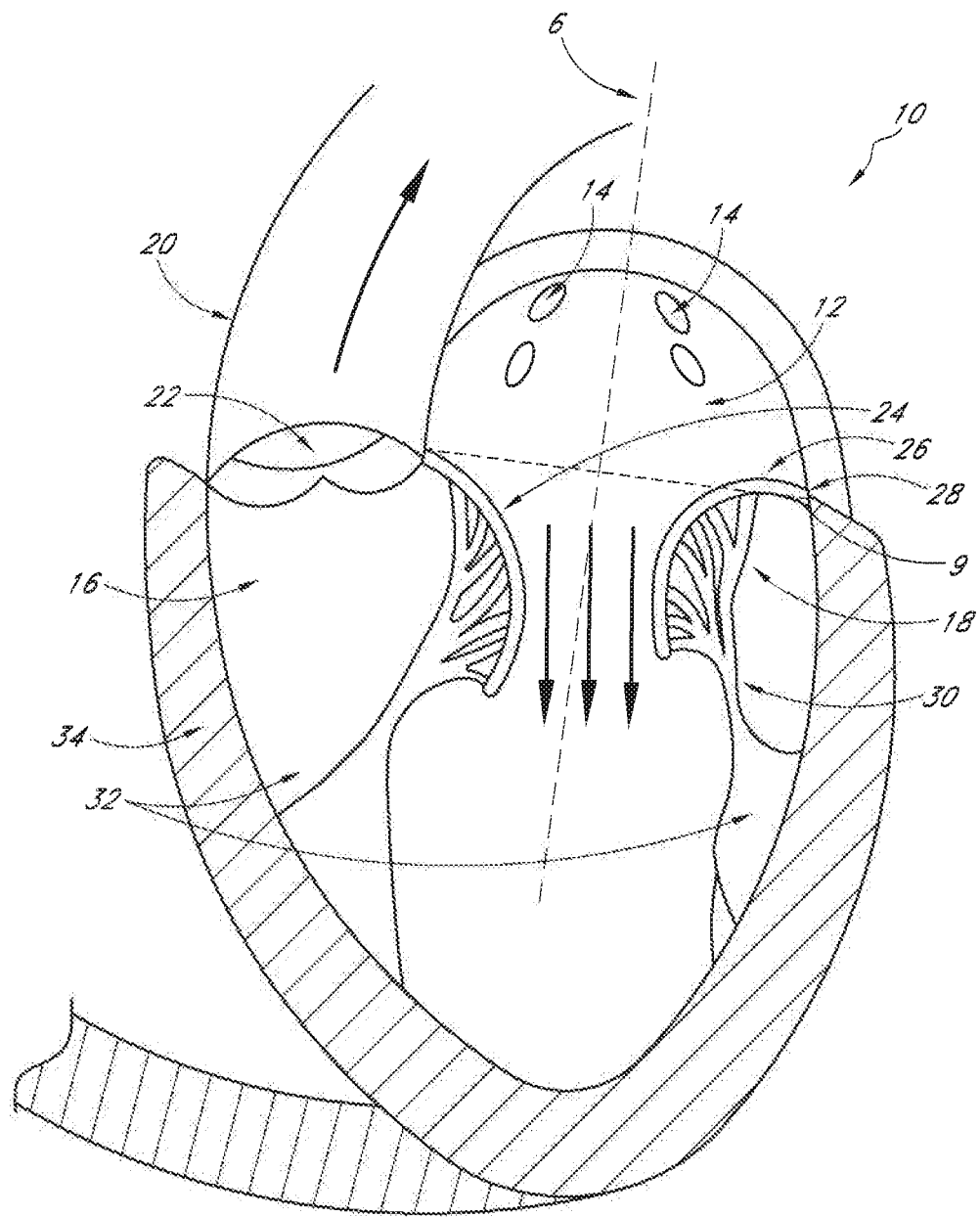
FIG. 2 is a cross-sectional view of the heart with a normal mitral valve during diastole. The axis of the mitral valve is illustrated, and shown piercing the intraannular plane.

FIG. 2 illustrates a cross-sectional view of the heart 10 with a normal mitral valve 18 in diastole. After the left ventricle 16 has ejected the blood into the aorta, the left ventricle relaxes, which results in a drop in pressure within the left ventricle 16. When the pressure in the left ventricle 16 drops below the pressure in the aorta 20, the aortic valve 22 closes. The pressure within the left ventricle 16 continues dropping until the pressure in the left ventricle 16 is less than the pressure in the left atrium 12, at which point the mitral valve 18 opens, as shown in FIG. 2. During the early filling phase, blood passively fills the left ventricle 16 and this accounts for most of the filling of the left ventricle 16 in an individual at rest. At the end of the filling phase, the left atrium 12 contracts and provides a final kick that ejects additional blood into the left ventricle. Also shown is intraannular plane 9 as described above, and line 6 representing the longitudinal axis 6 of the valve 18.

Figures 3, 4:
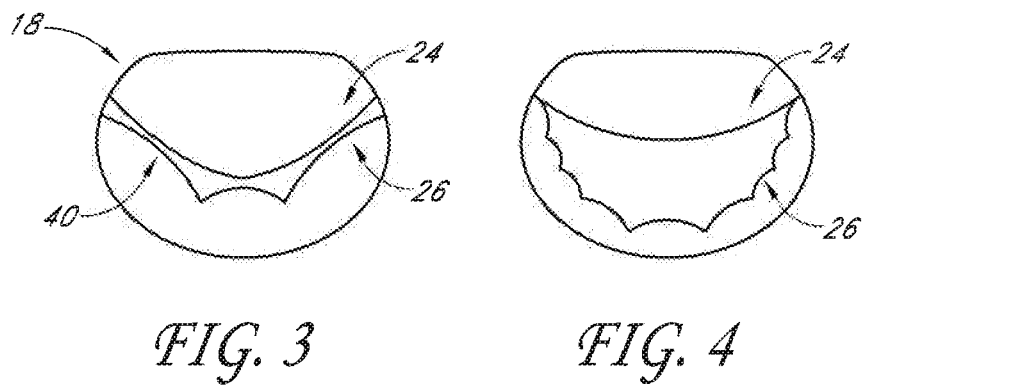
FIG. 3 is a bottom view of the normal mitral valve of FIG. 1 during systole looking from the left atrium to the left ventricle.
FIG. 4 is a bottom view of the normal mitral valve of FIG. 2 during diastole looking from the left atrium to the left ventricle.
Figures 5, 6:
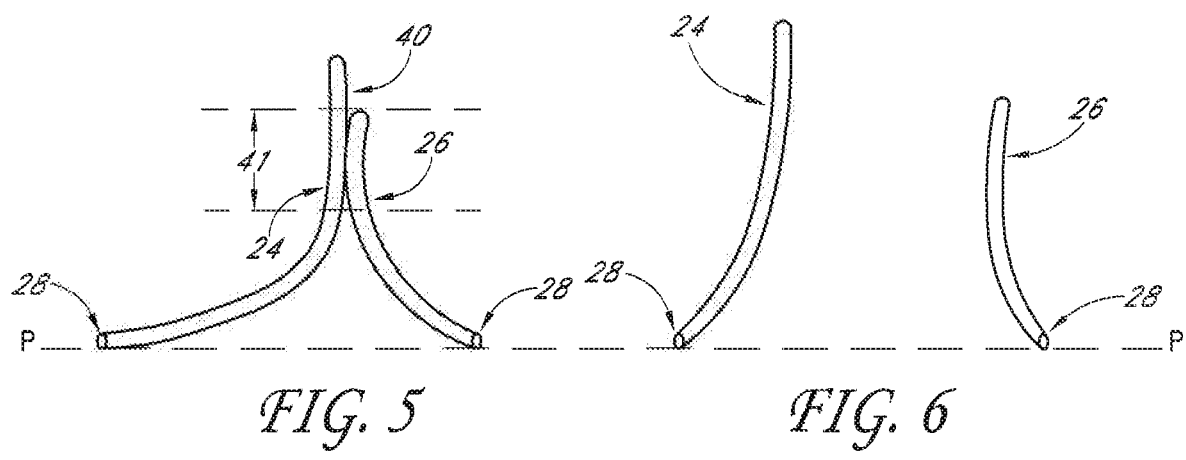
FIG. 5 is a cross-sectional schematic view of the normal mitral valve of FIG. 1 during systole, illustrating the depth of the coaption zone.
FIG. 6 is a cross-sectional schematic view of the normal mitral valve of FIG. 2 during diastole.

FIG. 3 illustrates a bottom view of normal mitral valve 18 in systole, looking from the left atrium and to the left ventricle. As shown, the anterior leaflet 24 and posterior leaflet 26 are properly coapted, thereby forming a coaptive edge 40 that forms a seal that prevents retrograde flow of blood through the mitral valve 18, which is known as mitral regurgitation. FIG. 4 illustrates a bottom view of normal mitral valve 18 in diastole. FIG. 5 provides a side cross-sectional view of a normal mitral valve 18 in systole. As shown in FIG. 5, the valve leaflets 24 and 26 do not normally cross the plane P defined by the annulus and the free edges 36 and 38 coapt together to form a coaptive edge 40.

FIG. 5 also illustrates a coaption zone 41. Preferably the depth of coaption (length of zone 41 in the direction of blood flow, in which the leaflets 24 and 26 are in contact) is at least about 2 mm or 5 mm, and is preferably within the range of from about 7 mm to about 10 mm for the mitral valve.

Thus, implantation of the devices in accordance with the present invention preferably achieves an increase in the depth of coaption. At increase of at least about 1 mm, preferably at least about 2 mm, and in some instances an increase of at least about 3 mm to 5 mm or more may be accomplished.

Figure 19A:
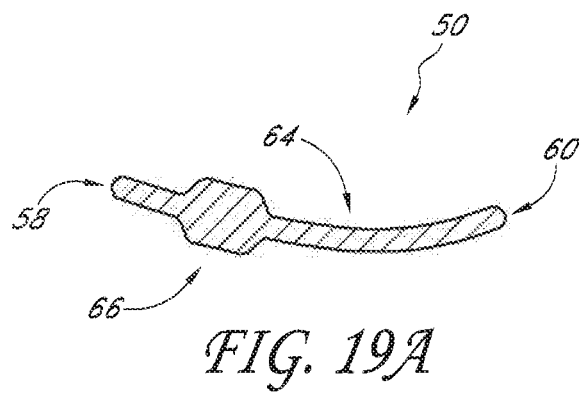
FIG. 19A shows a perspective view of yet another embodiment of a transvalvular band, with a widened coaptive edge support portion.
Figure 19B:
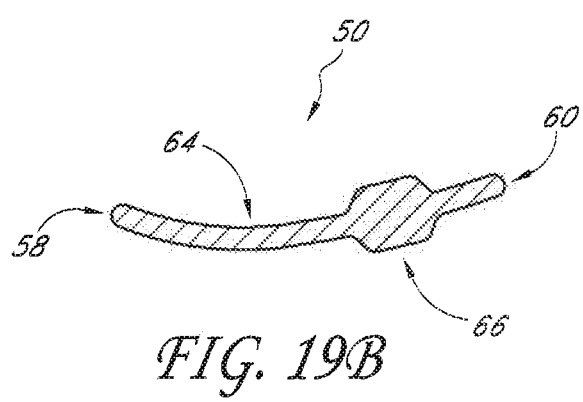
FIG. 19B shows a perspective view of yet another embodiment of a transvalvular band, with a widened coaptive edge support portion.

In addition to improving coaption depth, implantation of devices in accordance with the present invention preferably also increase the width of coaptation along the coaption plane. This may be accomplished, for example, by utilizing an implant having a widened portion for contacting the leaflets in the area of coaption such as is illustrated in connection with FIGS. 19A and 19B below. A further modification of the coaptive action of the leaflets which is accomplished in accordance with the present invention is to achieve early coaption. This is accomplished by the curvature or other elevation of the implant in the ventricle direction. This allows the present invention to achieve early coaption relative to the cardiac cycle, relative to the coaption point prior to implantation of devices in accordance with the present invention.

FIGS. 4 and 6 illustrate normal mitral valve 18 in diastole. As shown, the anterior leaflet 24 and posterior leaflet 26 are in a fully opened configuration which allows blood to flow from the left atrium to the left ventricle.

Figure 7:
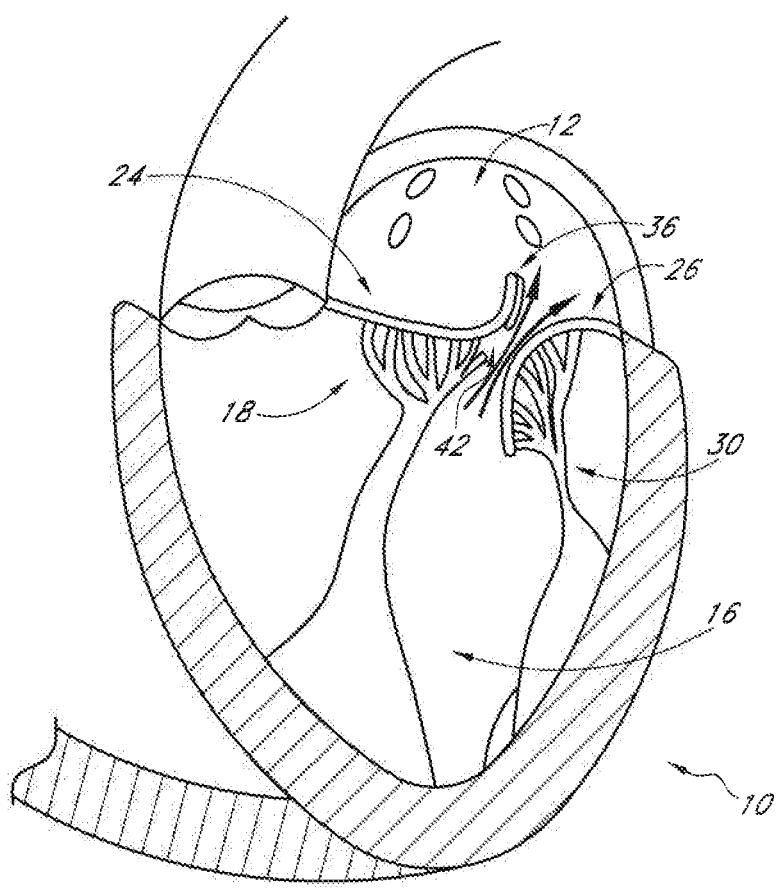
FIG. 7 is a cross-sectional view of the heart during systole showing a mitral valve with a prolapsed anterior leaflet caused by the rupture of the chordae tendineae attached to the anterior leaflet.
Figure 8:
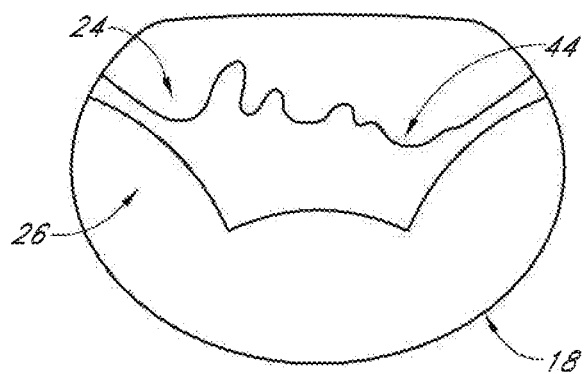
FIG. 8 is a bottom view of the mitral valve of FIG. 7 having a prolapsed anterior leaflet looking from the left atrium to the left ventricle.

FIGS. 7 and 8 illustrate a heart 10 in systole where the anterior leaflet 24 of the mitral valve 18 is in prolapse. Anterior leaflet 24 prolapse can be caused by a variety of mechanisms. For example, as illustrated in FIG. 7, rupture 42 of a portion of the chordae tendineae 30 attached to the anterior leaflet 24 can cause the free edge 36 of the anterior leaflet 24 to invert during mitral valve 18 closure. As shown in FIG. 8, inversion 44 of the anterior leaflet 24 can prevent the mitral valve leaflets 24 and 26 from properly coapting and forming a seal. This situation where the free edge 36 of the anterior leaflet 24 crosses into the left atrium 12 during mitral valve 18 closure can lead to mitral regurgitation.

Figure 9:
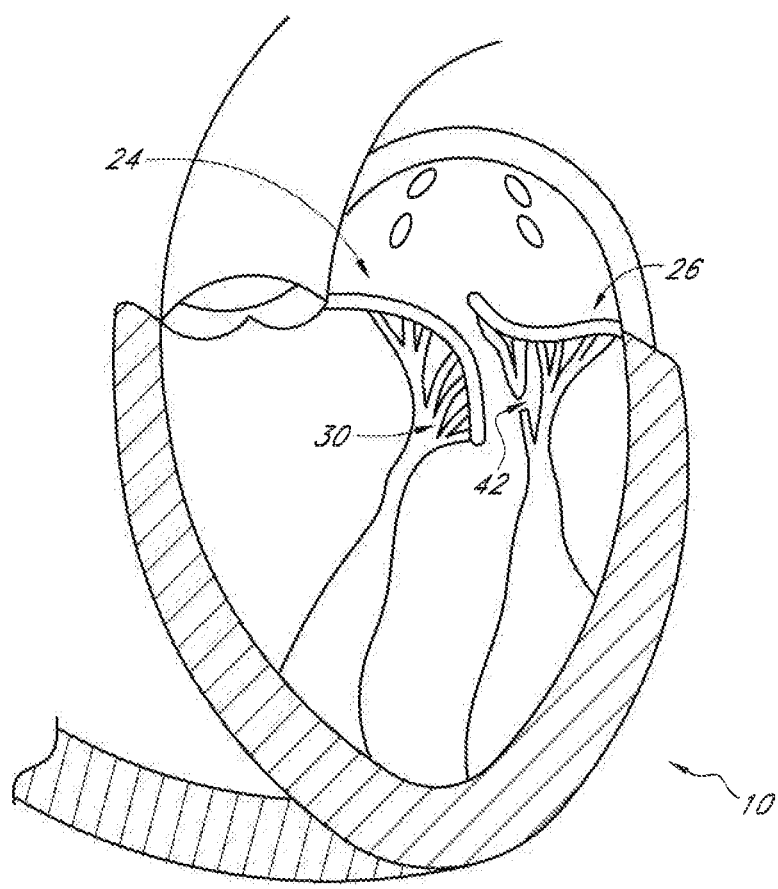
FIG. 9 is a cross-sectional view of the heart during systole showing a mitral valve with a prolapsed posterior leaflet caused by the rupture of the chordae tendineae attached to the posterior leaflet.
Figure 10:
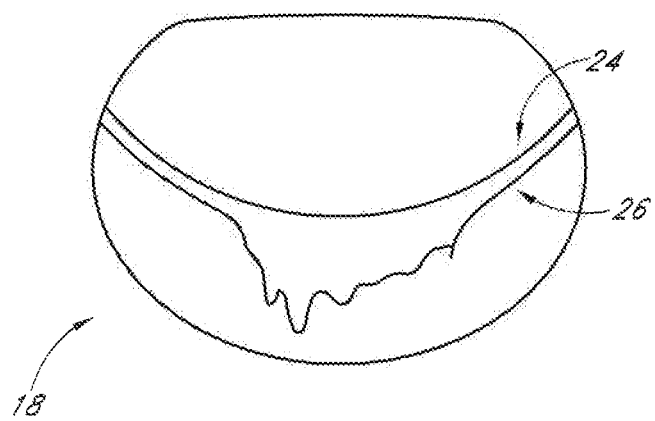
FIG. 10 is a bottom view of the mitral valve of FIG. 9 having a prolapsed posterior leaflet looking from the left atrium to the left ventricle.

Similarly, FIGS. 9 and 10 illustrate posterior leaflet 26 prolapse caused by a rupture of the chordae tendineae 30 attached to the posterior leaflet 26. In this case, the posterior leaflet 26 can invert and cross into the left atrium 12 during mitral valve 18 closure. The inversion of the posterior leaflet 26 prevents the mitral valve leaflets 24 and 26 from properly coapting and forming a seal, which can lead to mitral regurgitation.

Figure 11:
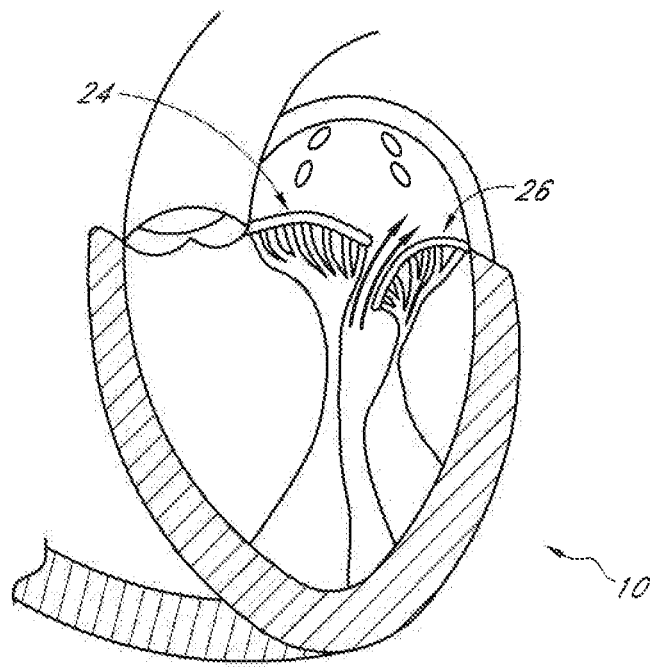
FIG. 11 is a cross-sectional view of the heart during systole showing a mitral valve with anterior leaflet prolapse.
Figure 11A:
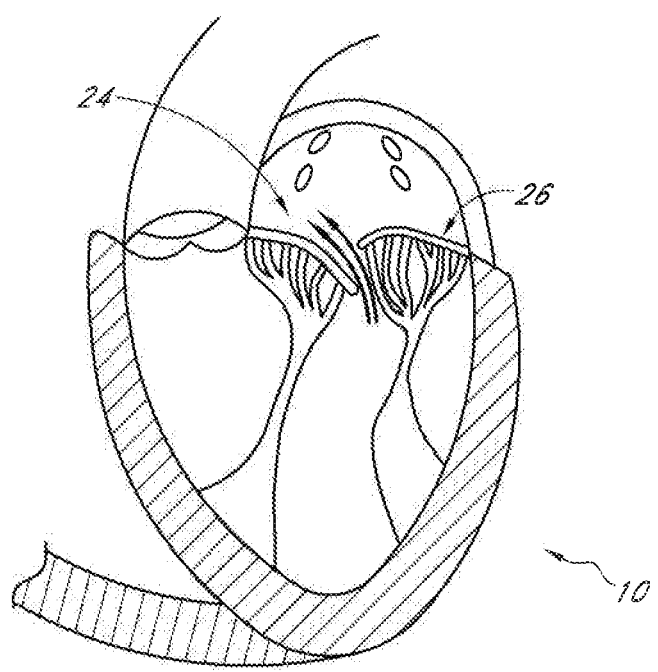
FIG. 11A is a cross sectional view as in FIG. 11, showing posterior leaflet prolapse.
Figure 11B:
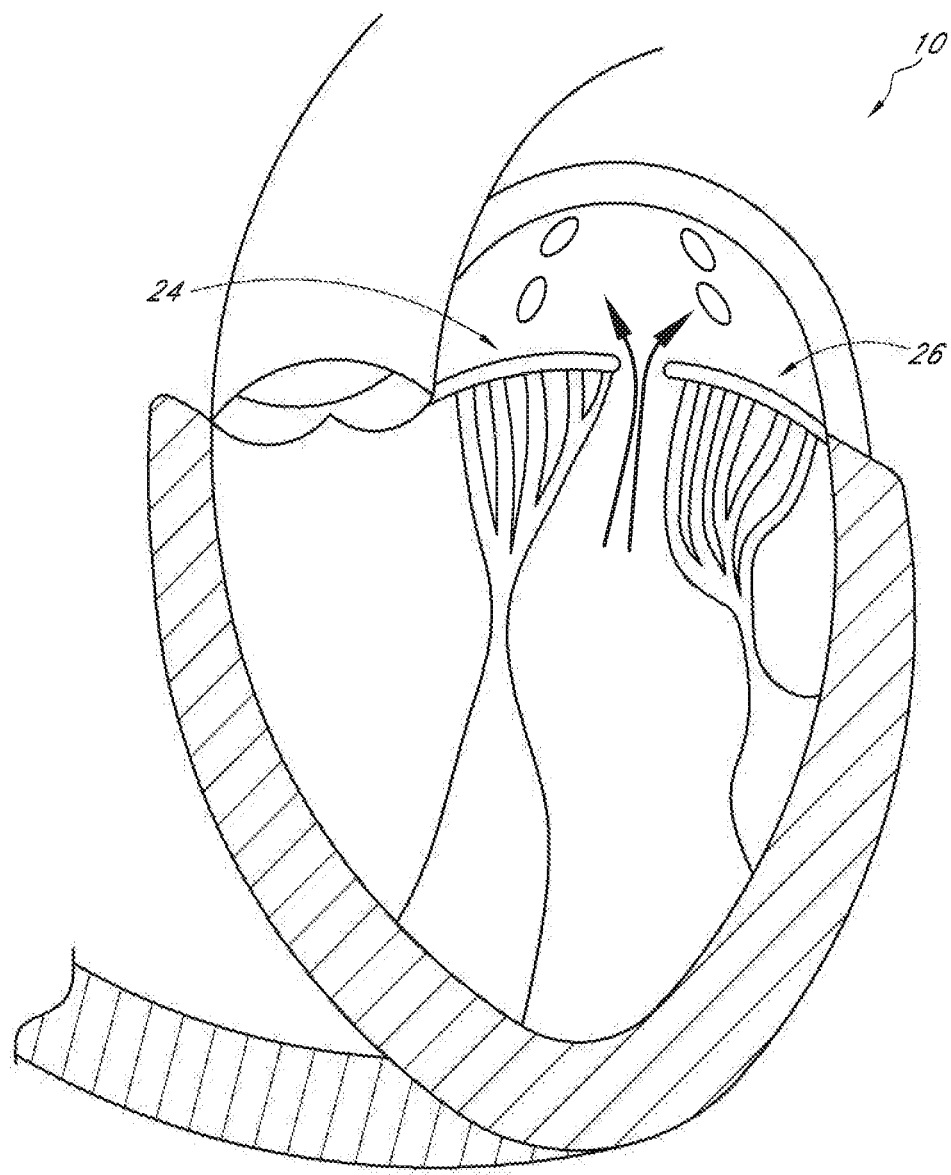
FIG. 11B is a cross sectional view as in FIG. 11, showing bileaflet prolapse with mitral regurgitation.
Figure 11C:
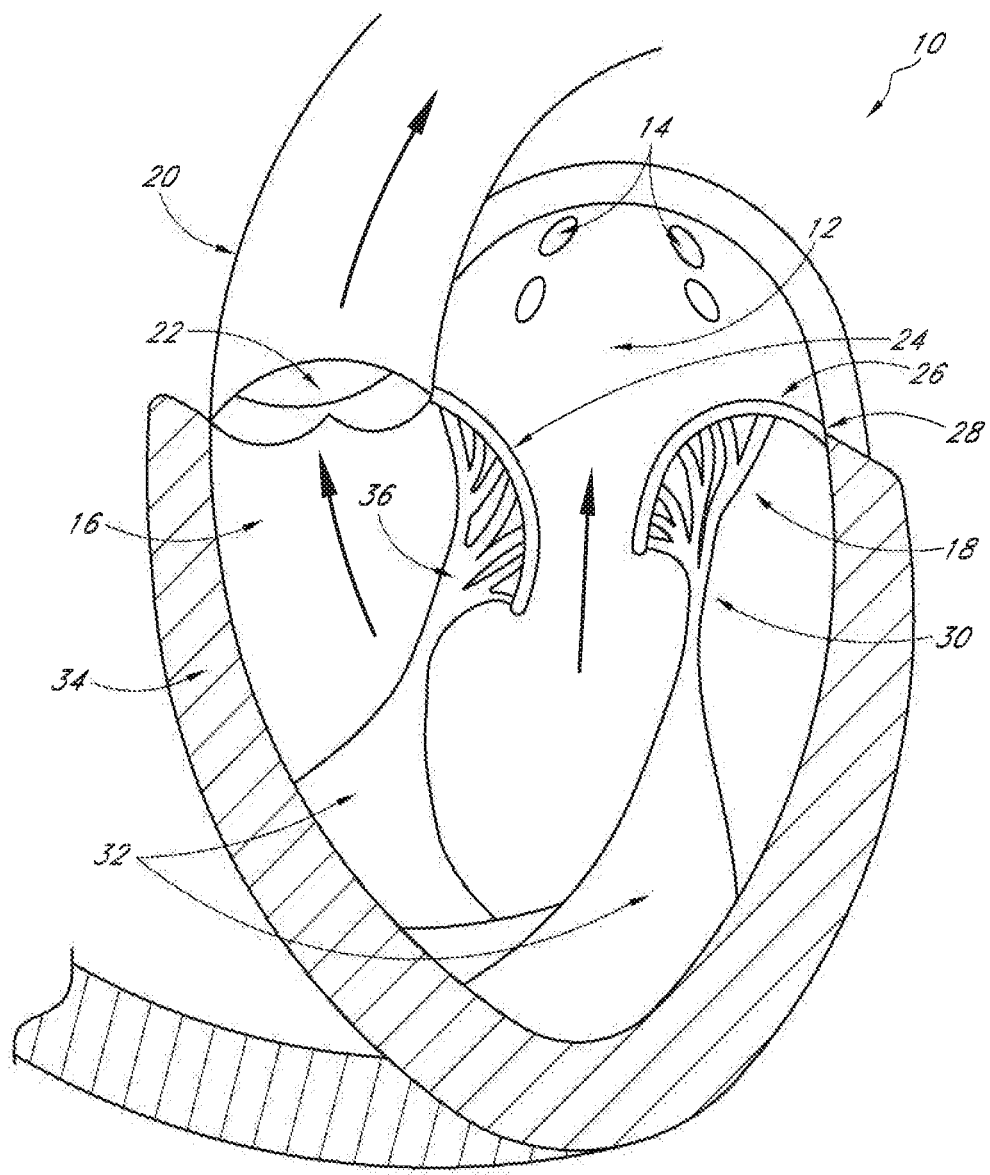
FIG. 11C illustrates a dilated mitral annulus with little or no coaption of both leaflets causing central mitral regurgitation in ischemic cardiomyopathy.

Mitral regurgitation can also be caused by an elongated valve leaflet 24 and 26. For example, an elongated anterior leaflet 24, as shown in FIG. 11, can prevent the valve leaflets 24 and 26 from properly coapting during mitral valve 18 closure. This can lead to excessive bulging of the anterior leaflet 24 into the left atrium 12 and misalignment of the free edges 36 and 38 during coaptation, which can lead to mitral regurgitation.

Figure 12:
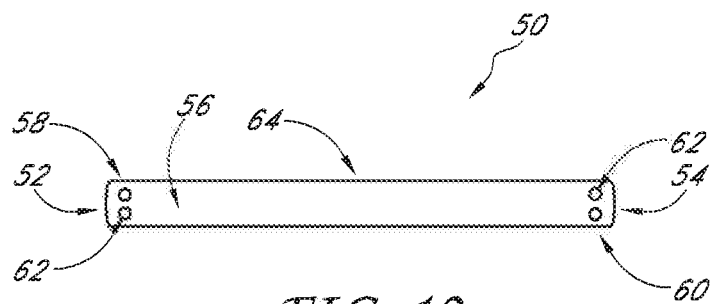
FIG. 12 is a top view of an embodiment of a transvalvular band.
Figure 13:
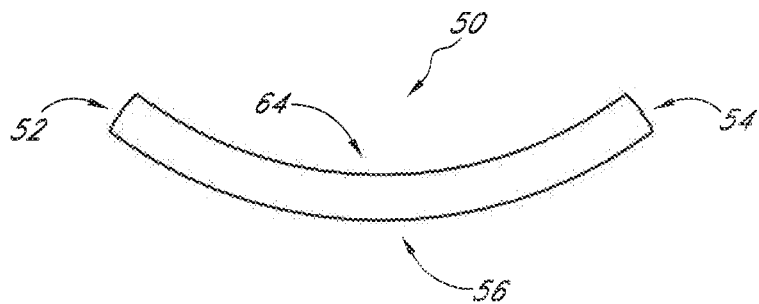
FIG. 13 is a side view of the transvalvular band of FIG. 12.

One embodiment of a transvalvular band 50 that would improve mitral valve leaflet 24 and 26 coaptation and prevent or reduce mitral regurgitation is illustrated in FIGS. 12 and 13. FIG. 12 provides a top view of the transvalvular band 50 while FIG. 13 provides a side view of the transvalvular band 50. In this embodiment, the transvalvular band 50 comprises an elongate and curved structure with a first end 52, a second end 54, a central portion 64 located between the two ends 52 and 54, and a length that is capable of extending across the annulus. The leaflet contact surface 56 is convex along the longitudinal axis, as best illustrated in FIG. 13. In other embodiments, the leaflet contact surface 56 can have a different shape and profile. For example, the contact surface 56 can be concave, straight, a combination of convex, concave and/or straight, or two concave or straight portions joined together at an apex. As illustrated in FIG. 12, the transvalvular band 50 can have a substantially constant width between the first end 52 and the second end 54. The first end 52 has a first anchoring portion 58 and the second end 54 has a second anchoring portion 60.

The anchoring portions 58 and 60 can have holes 62 for sutures that allow the transvalvular band 50 to be secured to the annulus. Alternatively, in other embodiments the anchoring portions 58 and 60 can have other means for securing the transvalvular band 50 to the annulus. For example, the anchoring portions 58 and 60 can be made of a membrane or other fabric-like material such as Dacron or ePTFE. Sutures can be threaded directly through the fabric without the need for distinct holes 62. The fabric can be attached to the other portions of the transvalvular band 50 by a variety of techniques. For example, the fabric can be attached to the other portions of the transvalvular band 50 with the use of an adhesive, by suturing, by tying, by clamping or by fusing the parts together. Another non-limiting technique of securing the transvalvular band to the annulus is to coat a malleable metal basis material, which creates structure for securing a skeleton of the transvalvular band, with a polymer such as silicone and bonding a material, such as PET (i.e., Dacron) velour for comprehensive tissue ingrowth when desired.

Figure 14:
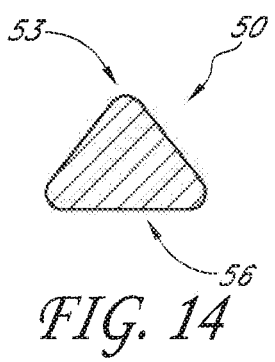
FIG. 14 is a cross-sectional view of a transvalvular band with a triangular cross-section.
Figure 15:
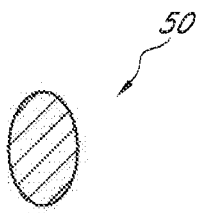
FIG. 15 is a cross-sectional view of a transvalvular band with an oblong cross-section.
Figure 16:
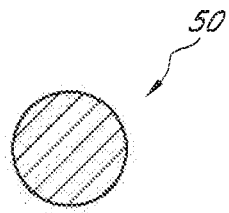
FIG. 16 is a cross-sectional view of a transvalvular band with a circular cross-section.
Figure 17:
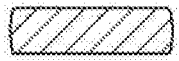
FIG. 17 is a cross-sectional view of a transvalvular band with a rectangular cross-section.

The central portion of the transvalvular band 50 can have a variety of cross-sectional shapes, as illustrated in FIGS. 14-17. For example, the cross sectional shape can be substantially rectangular, circular, oblong or triangular. The edges of the transvalvular band 50 can be rounded or otherwise configured so that the transvalvular band 50 presents an atraumatic surface 51 to the valve leaflets. In some embodiments, the cross-section can be oriented in a particular fashion to enhance performance of the transvalvular band 50. For example as shown in FIG. 14, a transvalvular band 50 with a triangular cross section can be designed so that a relatively larger surface 56 of the triangle contacts the valve leaflets while a lower profile leading edge 53 of the triangle opposite the surface 51 faces the left atrium. This configuration allows a larger surface area to make contact with and support the mitral valve leaflets, while also presenting a more streamlined shape that provides less resistance to blood flowing from the left atrium to the left ventricle. Decreasing the resistance to blood flow is desirable because it can reduce turbulence and reduce the impedance of the transvalvular band 50 on the filling of the left ventricle. Similarly, the transvalvular bands 50 with an oblong or rectangular cross-section can be oriented to either increase the surface area for contact with the valve leaflets, or be oriented to reduce the resistance to blood flow.

The dimensions of the transvalvular band 50 will vary, depending upon the specific configuration of the band 50 as well as the intended patient. In general, transvalvular band 50 will have an axial length from first end 52 to second end 54 within the range of from about 20 mm to about 32 mm. In one embodiment, intended for a typical male adult, the axial length of the transvalvular band 50 is about 24 mm to 26 mm. The width of the transvalvular band 50 in the central zone 64 may be varied depending upon the desired performance, as will be discussed herein. In general, the trailing surface 51 against which leaflets will seat is preferably large enough to minimize the risk of erosion resulting from repeated contact between the closed leaflets and the implant. The width of the leading edge 53 is preferably minimized, as discussed above, to minimize flow turbulence and flow obstruction. In general, widths of the surface 51 measured perpendicular to the flow of blood are presently contemplated to be less than about 5 mm, and often within the range of from about 5 mm to about 10 mm in the zone of coaptation.

Figure 18:
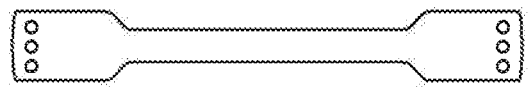
FIG. 18 is a top view of another embodiment of a transvalvular band.

In some embodiments as illustrated in FIG. 18, the central portion 64 of the transvalvular band 50 can be narrower in width, measured perpendicular to blood flow than the first and second anchoring portions 58 and 60. By narrowing the central portion 64, the resistance to blood flow can be reduced. However, narrowing the central portion 64 reduces the surface area of the leaflet contact surface 56 that supports the valve leaflets.

In the embodiment illustrated in FIG. 18, the narrowed central portion 64 is separated from the first anchoring portion 58 and second anchoring portion 60 by a first shoulder 57 and second shoulder 59. The length of the central portion 64, between first shoulder 57 and second shoulder 59 can be less than about 50% of the overall length of the device, or less than about 30% of the overall length of the device if it is desired to minimize the obstruction in the center of the flow path, while presenting a wider transverse surface for supporting the leaflets when the valve is closed. Alternatively, the length of the central zone 64 may be greater than 50%, and in some embodiments greater than 75% of the overall length of the implant.

In some embodiments as illustrated in FIGS. 19A, 19B, 21 and 23, a coaptive edge support portion 66 of the central portion 64 of the transvalvular band 50 can be wider than the adjacent portions of the transvalvular band 50, leading up to and potentially including the first and second anchoring portions 58 and 60. By increasing the width and surface area of the coaptive edge support portion 66, more support can be provided to the valve leaflets at the coaptive edge. This increased support can increase the width of leaflet coaption. The other portions of the central portion 64 can remain narrow to reduce the resistance to blood flow. The support portion 66 can be located at a fixed position or adjustable along the transvalvular band so that its position can be optimized by the surgeon and then secured at a fixed point such as by suturing, or removed if deemed unnecessary.

In one implementation of the invention, the transvalvular band comprises a first component for primary reduction and a second component for fine adjustment. For example, the device illustrated in FIG. 19A may be provided with an adjustable (e.g. slidable) support portion 66. The transvalvular band may be positioned across the annulus as has been described herein, and hemodynamic function of the valve may be evaluated. The support portion 66 may thereafter be adjusted along the length of the transvalvular band to treat residual leakage or otherwise optimize the functionality of the implant such as by increasing the zone of coaptation. The second component (e.g. support portion 66) may thereafter be fixed with respect to the transvalvular band such as by sutures, clips, adhesives, or other techniques known in the art. Alternatively, the second portion may be separate from and connectable to the transvalvular band such as stitching, clips, suturing or other technique known in the art.

In addition, the coaptive edge support portion 66 can be offset from the center of the transvalvular band 50, to reflect the asymmetry between the anterior leaflet and the posterior leaflet. For example, the coaptive edge support portion 66 can be positioned closer to the first anchoring portion 58 than to the second anchoring portion 60. In certain embodiments, the edge support portion 66 will be centered about a point which is within the range of from about 20% to about 45% of the overall length of the implant from the closest end.

Figure 20:
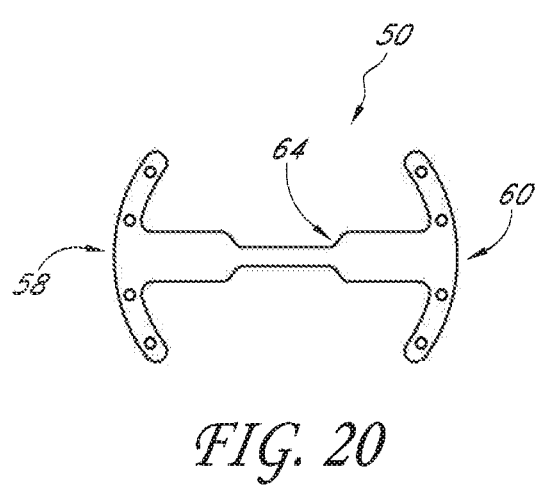
FIGS. 20-23 are top views of other embodiments of a transvalvular band.

FIG. 20 illustrates another embodiment of a transvalvular band 50 that is a modification of the transvalvular band 50 shown in FIG. 18. As illustrated in FIG. 20, the transvalvular band 50 has a narrow central portion 64 that provides relatively low resistance to blood flow. However, the first and second anchoring portions 58 and 60 extend further in a lateral direction, and can be arcuate to conform to the mitral valve annulus. These laterally extended anchoring portions 58 and 60 provide additional anchoring of the transvalvular band 50 and can help improve the stability of the device after implantation. The laterally extending anchoring portion 58 and 60 may be provided with any of a variety of structures for facilitating anchoring to the valve annulus. For example, they may be provided with a plurality of apertures 61, for conventional stitching or to receive any of a variety of clips or tissue anchors. The anchoring portions may alternatively be provided with any of a variety of barbs or hooks, or may be provided with a fabric covering such as a Dacron sleeve to facilitate sewing. Further, in some embodiments, this sewing ring may have an elastomeric core upon which the Dacron is secured to provide a more compliant structure to hold the implant. Measured in the circumferential direction (transverse to the longitudinal axis of the implant 50) the laterally extending anchoring portions will have an arc length of greater than about 5 mm, and, in some embodiments, greater than about 1 cm. Arc lengths of at least about 2 cm, and, in some embodiments, at least about 3 cm may be utilized, depending upon the desired clinical performance.

Figure 21:
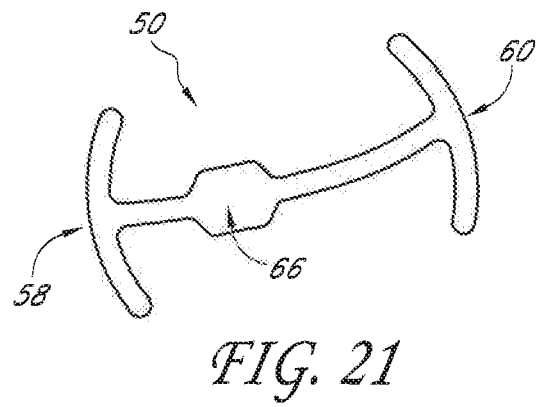

FIG. 21 illustrates another embodiment of a transvalvular band 50 with the extended anchoring portions 58 and 60 and a wider, offset coaptive edge support portion 66. This embodiment has the benefit of additional stability provided by the extended anchoring portions 58 and 60 and enhanced support of the coaptive edge.

Figure 22:
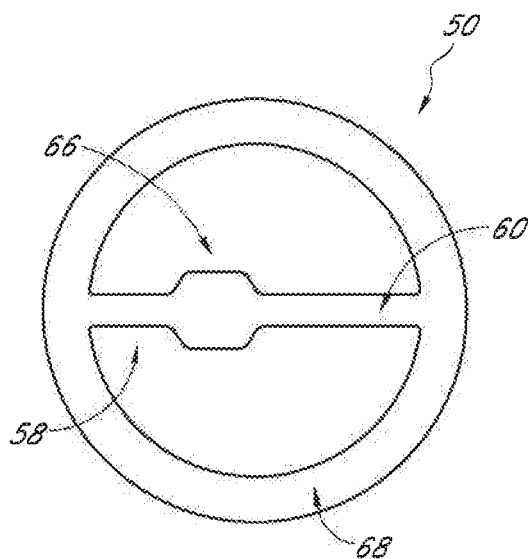
Figure 23:
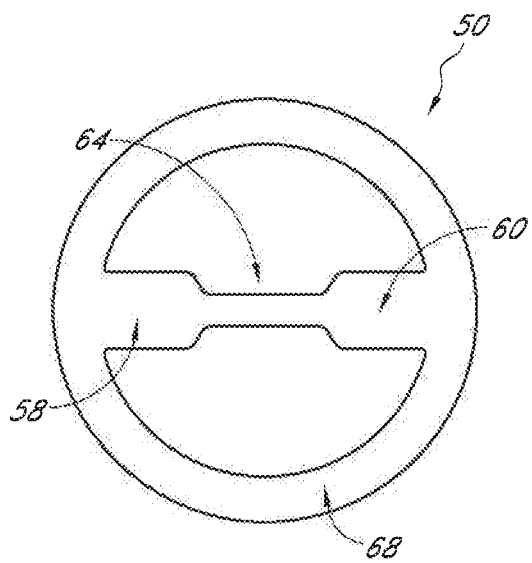

FIGS. 22 and 23 illustrate another embodiment of a transvalvular band 50 which is combined with an annular ring 68. The annular ring 68 can be used as both a support for the transvalvular band 50 and, if desired, also to help stabilize the size and shape of the mitral valve annulus itself. In some embodiments, the annular ring 68 can be used to reduce the size of the mitral valve annulus and to bring the mitral valve leaflets closer together. This can be accomplished by, for example, suturing the mitral valve annulus to an annular ring 68 of smaller diameter. In addition, the annular ring 68 provides additional support and stability to the transvalvular band 50. The anchoring portions 58 and 60 of the transvalvular band 50 can be formed integrally with the annular ring 68, or the anchoring portions 58 and 60 can be attached to the annular ring by a variety of means, such as suturing, bonding, adhesives, stapling and fusing. FIG. 22 discloses an embodiment with a narrow central portion 64 while FIG. 23 discloses an embodiment with a wider, offset coaptive edge support portion 66.

Figure 23A:
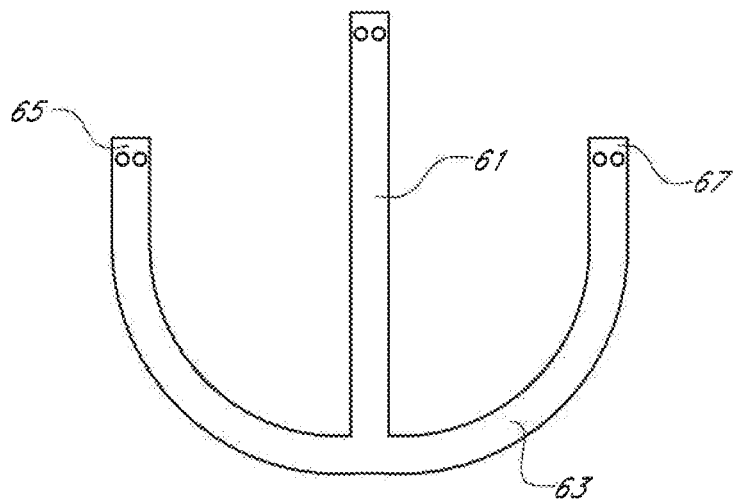
FIG. 23A shows a central mitral transvalvular band with posterior annuloplasty ring.

FIG. 23A illustrates a further implementation of the invention, adapted to treat ischemic mitral regurgitation with posterior annuloplasty. A transvalvular band 61 is provided for spanning the leaflet coaption plane as has been described herein. Any of the features described in connection with other transvalvular bands disclosed herein may be incorporated into the transvalvular band 61.

An arcuate posterior annuloplasty support 63 is connected to the transvalvular band 61, and adapted to extend for an arc length along the native annulus. In the illustrated embodiment, the support 63 extends through an arc of approximately 180°, extending from a first trigone attachment zone 65 to a second trigone attachment zone 67. The attachment zones may be provided with sewing apertures, a fabric covering, or other structure for facilitating attachment to tissue. In general, the transvalvular band 61 will have dimensions similar to those described elsewhere herein. The transverse dimension from first trigone zone 65 to second trigone zone 67 may be varied depending upon the size of the native annulus, but will generally be within the range of from about 35 mm to about 45 mm.

Figure 23B:
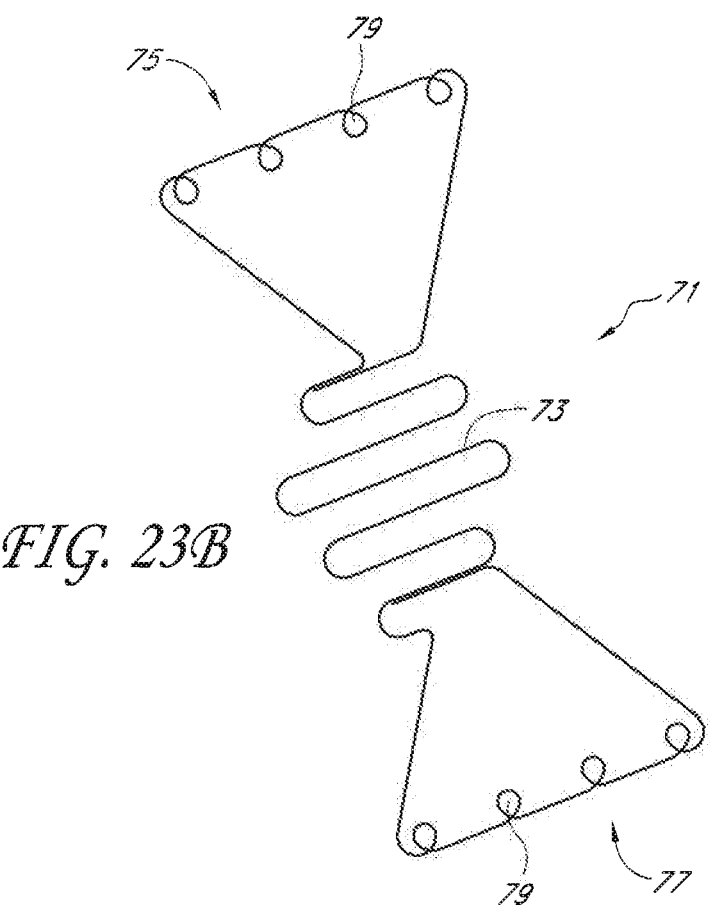
FIG. 23B shows an intraannular band formed from a length of wire.

Referring to FIG. 23B, there is illustrated a transvalvular band in accordance with the present invention, formed from a single length or several lengths of flexible wire. The bend angles and orientation of the struts in the illustrated embodiment may be readily altered, to accommodate the desired axes of compression which may be desirable for a particular deployment procedure.

In general, the transvalvular band 71 comprises an elongate flexible wire 73 formed into a serpentine pattern, for providing a support for the valve leaflets as has been discussed herein. Although not illustrated in FIG. 23B, the wire 73 may be formed such that it bows or inclines in the direction of the ventricle to achieve early closure as is discussed elsewhere herein. The wire 73 may extend into a first connection section 75 and a second connection section 77. Each of the connection sections 75 and 77 may be provided with a plurality of eyelets 79, to receive sutures for attaching the implant to the valve annulus. The implant may be formed from any of a variety of flexible materials, including various polymers described elsewhere herein as well as titanium, titanium alloy, Nitinol, stainless steel, elgiloy, MP35N, or other metals known in the art. This design has an advantage of providing a relatively large support footprint against the valve leaflets, while at the same time optimizing the area of open space to permit maximum blood flow therethrough. The design may be treated or coated with silicone or other suitable material to eliminate untoward effects such as thrombosis or corrosion. Treatments may be sequential and include more than one listed but not limited to electropolishing, harperization, tumbling, pickling, plating, encapsulation or physical vapor deposition of appropriate materials.

FIGS. 24-27 illustrate side views of transvalvular bands 50 with different inclinations. One of the objectives of the present invention is to not merely provide support to the leaflets during systole, but to elevate the plane of coaption in the direction of the ventricle, to cause early coaption (closure) relative to the cardiac cycle, as is discussed elsewhere herein. The variation in conditions, and other patient to patient variations may warrant production of the transvalvular band of the present invention in an array of sizes and/or configurations, so that clinical judgment may be exercised to select the appropriate implant for a given case. Alternatively, the transvalvular band may be provided in an adjustable form or a modular form so that an implant of the desired configuration can be constructed or modified intra-operatively at the clinical site. In a three segment embodiment, such as that illustrated in FIGS. 24 through 27, a central segment may be provided for positioning within the center of the flow path, or centered on the coaptive edges of the leaflets. First and second end portions may be connected to the central portion, for supporting the central portion relative to the tissue anchors. First and second end portions may be provided in a variety of lengths and curvatures, enabling construction of a relatively customized modular implant as may be desired for a particular patient.

Figure 24:
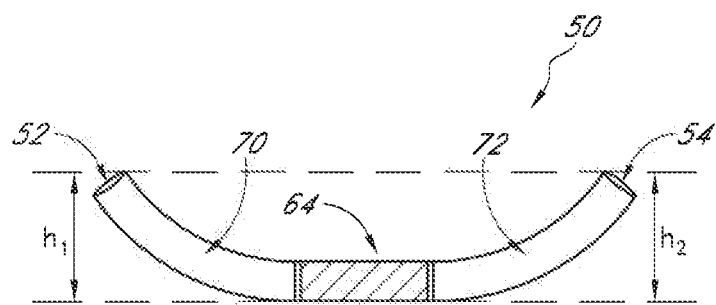
FIGS. 24-27 are side views of other embodiments of a transvalvular band.

For example, FIG. 24 illustrates a transvalvular band 50 with a central portion 64 and two gently angled arm portions 70 and 72. The first and second ends 52 and 54 are displaced from the central portion 64 by a height, h1 and h2, respectively. In FIG. 24, h1 and h2 are about equal and can range from about 0 mm to about 10 mm. Preferably h1 and h2 will be at least about 2 mm and will often be at least about 4 mm or 6 mm or more, but generally no more than about 10 mm or 12 mm.

Figure 25:
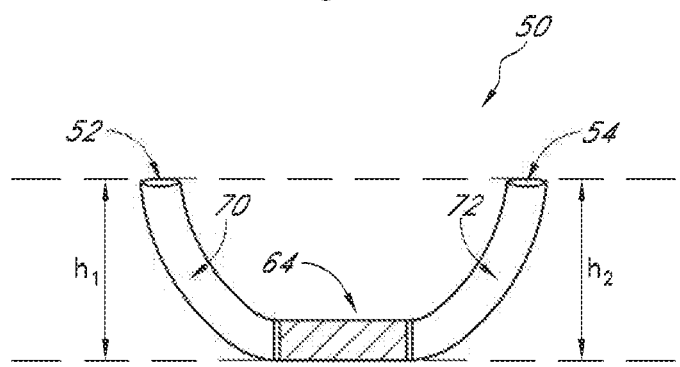
Figure 26:
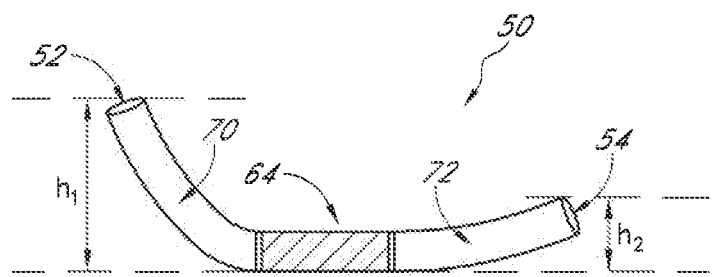
Figure 27:
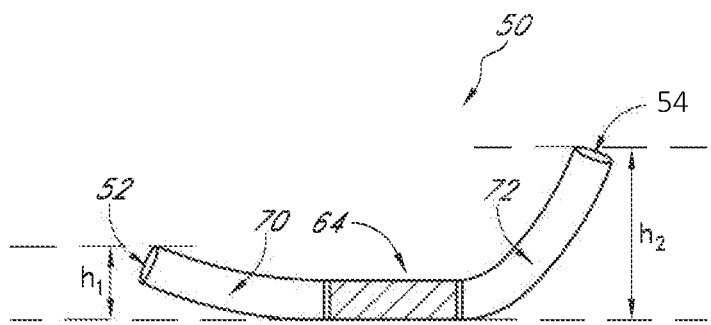

FIG. 25 illustrates a transvalvular band 50 with a central portion 64 and two sharply angled arm portions 70 and 72. The first and second ends 52 and 54 are displaced from the central portion 64 by a height, h1 and h2, respectively. In FIG. 25, h1 and h2 are about equal and can range from about 8 mm to about 12 mm. FIG. 26 illustrates a transvalvular band 50 with a central portion 64, a highly angled first arm 70 and a gently angled second arm 72. The first and second ends 52 and 54 are displaced from the central portion 64 by a height, h1 and h2, respectively. In FIG. 26, h1 is greater than h2. The h1 ranges from about 6 mm to about 10 mm, while h2 ranges from about 2 mm to about 6 mm. FIG. 27 illustrates a transvalvular band 50 with a central portion 64, a gently angled first arm 70 and a highly angled second arm 72. The first and second ends 52 and 54 are displaced from the central portion 64 by a height, h1 and h2, respectively. FIG. 27, may be a mirror image of FIG. 26.

The transvalvular band 50 can be made of any of a variety of materials that are compatible with implantation within a patient's body and which has the requisite structural integrity to support the mitral valve leaflets. For example, suitable materials include titanium, titanium alloys, stainless steel, stainless steel alloys, nitinol, elgiloy, MP35N, other metals and alloys, ceramics, and polymers such as PTFE, polycarbonate, polypropylene, UHMWPE, HDPE, PEEK, PEBAX and the like.

In order to reduce the thrombogenicity of the transvalvular band 50, the transvalvular band 50 can be provided with a smooth surface or appropriately micro-texture the surface in some embodiments, such as via a porous or microporous structure. Other factors such as surface chemistry, energy, morphology, macrofeatures, and general material properties matching the in situ needs can also be considered in tailoring the surface of the band. In addition, the transvalvular band 50 can be coated with a variety of substances to reduce thrombogenicity. For example, the transvalvular band 50 can be coated with a antithrombogenic agent such as heparin, a polymer such as PTFE, or a polymer conjugated with heparin or another antithrombogenic agent. Heparin coatings can be achieved in a variety of methods, one of which may be to coat or drip the prosthesis in TDMAC-heparin (Tridodecylmethylammonium heparinate).

As illustrated in FIGS. 28-31, the transvalvular band 50 is implanted in the plane of the mitral valve annulus 28 in a patient suffering from anterior leaflet 26 prolapse caused by the rupture 42 of the chordae tendineae 30 attached to the anterior leaflet 26. Although a prolapsed anterior leaflet 26 is illustrated, it should be understood that the method described herein is also applicable for treating other types of prolapse, such as posterior leaflet prolapse and prolapse caused by elongated leaflets 24 and 26. The transvalvular band 50 can be attached to the annulus 28 by a variety of techniques, such as sutures, anchors, barbs, stapes, self-expanding stents, or other techniques that are known or are apparent to those of skill in the art.

Figure 29:
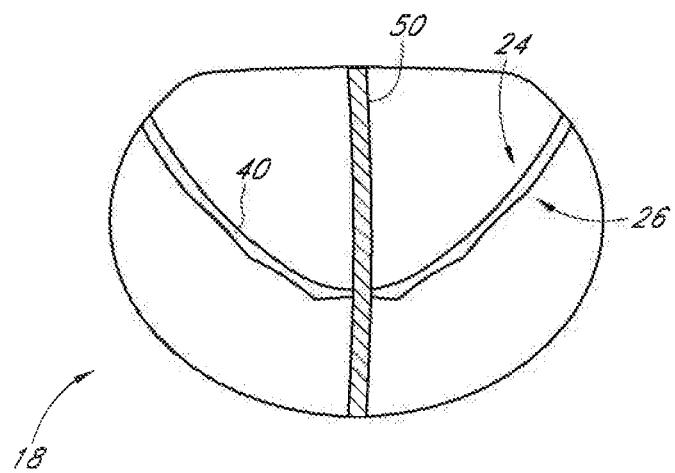
FIG. 29 is a bottom view of the mitral valve of FIG. 28 during systole with a transvalvular band implanted in the mitral annulus looking from the left atrium to the left ventricle.
Figure 31:
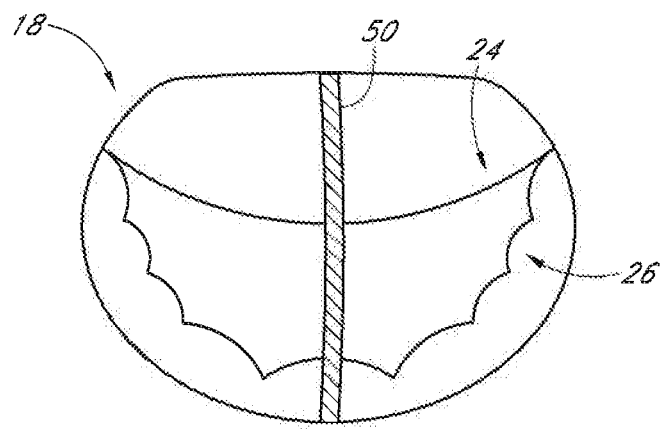
FIG. 31 is a bottom view of the mitral valve of FIG. 30 during diastole with a transvalvular band implanted in the mitral annulus looking from the left atrium to the left ventricle.

As best illustrated in FIGS. 29 and 31, the transvalvular band 50 is oriented in the annulus 28 so that the transvalvular band 50 is positioned approximately transversely to the coaptive edge 42 formed by the closure of the mitral valve leaflets 24 and 26. The transvalvular band 50 can also be positioned over the prolapsed portion of the anterior leaflet 26 so that the transvalvular band 50 can directly support the prolapsed portion of the anterior leaflet 24 and keep the anterior leaflet 24 inferior to the plane of the mitral valve annulus 28, i.e., elevated in the direction of the ventricle or of antegrade flow, thereby preventing or reducing prolapse and mitral regurgitation.

Figure 28:
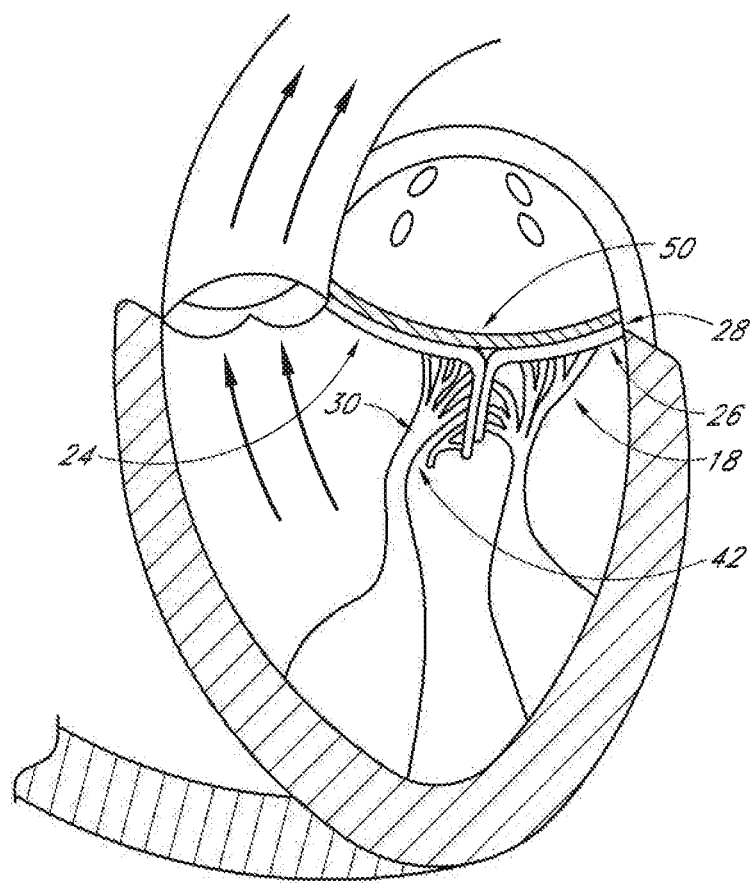
FIG. 28 is a cross-sectional view of a heart during systole with a transvalvular band implanted in the mitral annulus.

FIGS. 28 and 29 illustrate the effect of the transvalvular band 50 on the mitral valve 18 during systole. As shown, both the anterior leaflet 24 and the posterior leaflet 26 are supported by the transvalvular band during closure of the mitral valve 18. The arcuate transvalvular band 50 functions to keep both leaflets 24 and 26 inferior to the plane of the annulus 28 and enables the leaflets 24 and 26 to form a coaptive edge 40. Although a single transvalvular band 50 has been illustrated, in some embodiments, multiple transvalvular bands 50 such as two or three or more can be implanted across the annulus 28 to provide additional support to the mitral valve leaflets 24 and 26.

Figure 30:
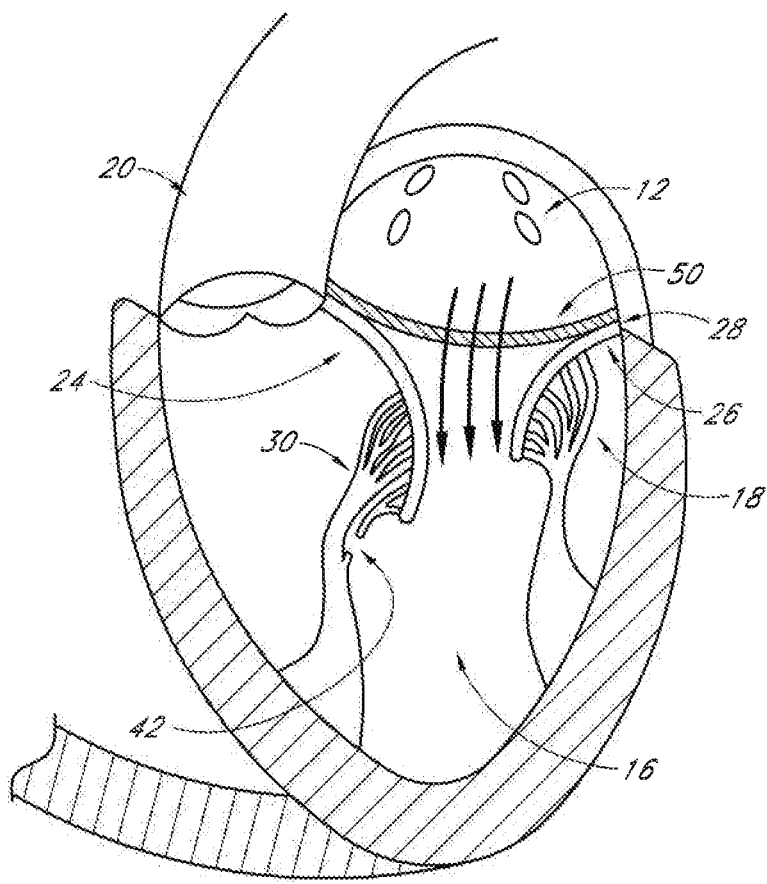
FIG. 30 is a cross-sectional view of a heart during diastole with mitral valve and a transvalvular band implanted in the mitral annulus.

FIGS. 30 and 31 illustrate the effect of the transvalvular band 50 on the mitral valve 18 during diastole. During diastole, the mitral valve 18 opens so that blood can fill the left ventricle 16 from the left atrium 12. As best illustrated in FIG. 31, the transvalvular band 50 obstructs only a small portion of the mitral valve 18 opening, and therefore, does not cause excessive resistance to blood flow.

Figures 32, 33:
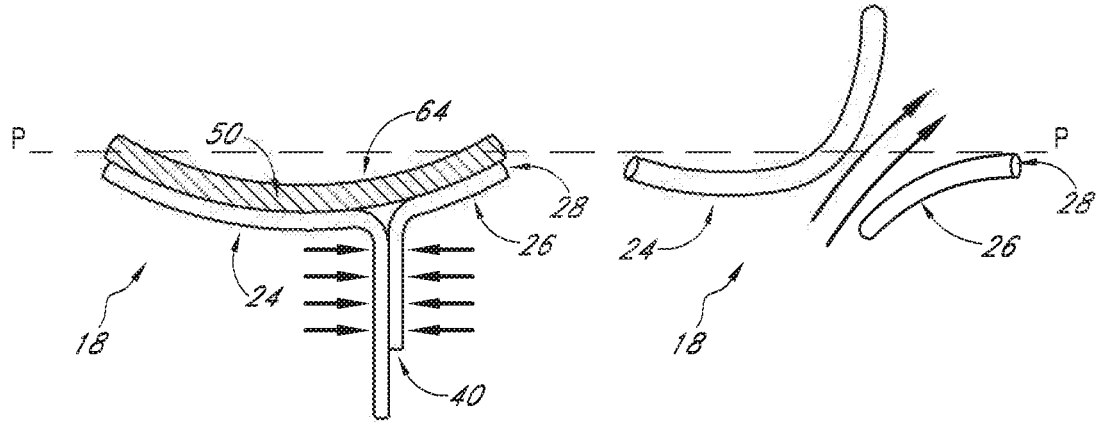
FIG. 32 is a cross-sectional schematic view of the mitral valve of FIG. 28 during systole with a transvalvular band implanted in the mitral annulus.
FIG. 33 is a cross-sectional schematic view of the mitral valve of FIG. 32 during systole without the transvalvular band implanted in the mitral annulus.
Figures 34, 35:
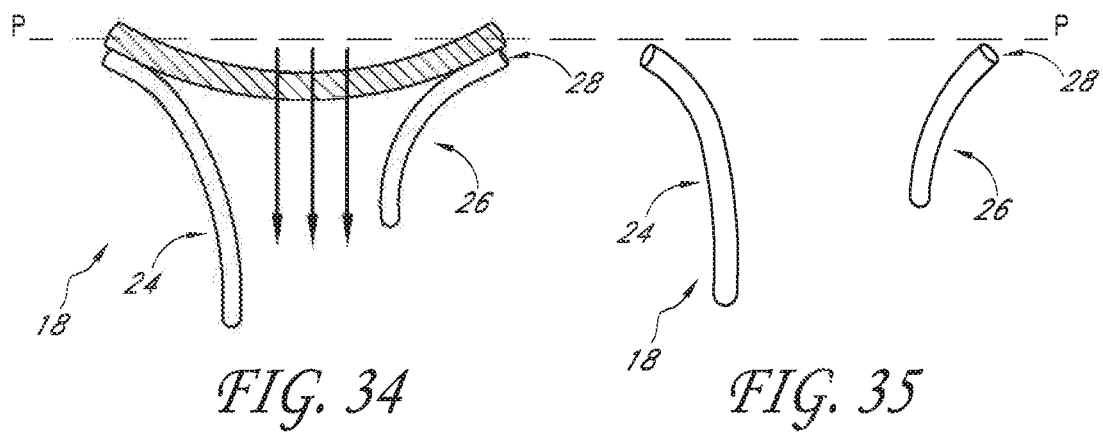
FIG. 34 is a cross-sectional schematic view of the mitral valve of FIG. 30 during diastole with the transvalvular band implanted in the mitral annulus.
FIG. 35 is a cross-sectional schematic view of the mitral valve of FIG. 34 during diastole without the transvalvular band implanted in the mitral annulus.

FIGS. 32-35 are cross-sectional side views of the mitral valve 18 with and without the support of the transvalvular band 50. During systole, the mitral valve 18 closes. Without the transvalvular band 50, the anterior leaflet 24 crosses the plane P defined by the mitral valve annulus 28 and prolapse, which leads to mitral regurgitation, as shown in FIG. 33. However, by implanting the transvalvular band 50 in the annulus 28 such that the arcuate transvalvular band 50 arches towards the left ventricle and the central portion 64 is displaced from the plane P, the anterior leaflet 24 is prevented from prolapsing above the plane P thus eliminating or reducing retrograde flow (shown in FIG. 33). The leaflets 24 and 26 rest upon the transvalvular band 50 and the pressure exerted by the blood upon the distal portion of the leaflets 24 and 26 form the coaptive edge 40. As illustrated in FIGS. 34 and 35, the performance of the mitral valve 18 during diastole is not substantially affected by the transvalvular band 50.

Figure 36:
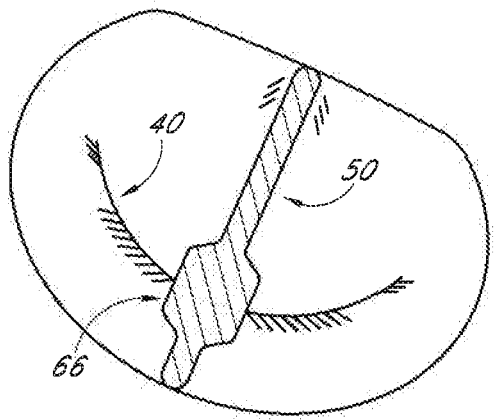
FIG. 36 is a bottom view of the mitral valve during systole with another embodiment of the transvalvular band implanted in the mitral annulus looking from the left atrium to the left ventricle.
Figure 38:
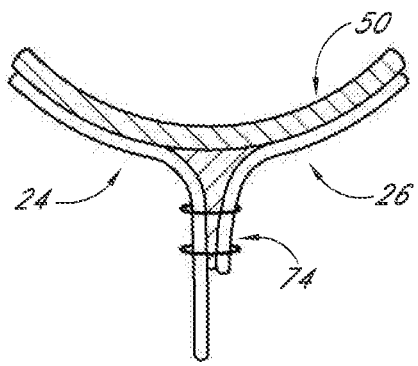
FIG. 38 is a cross-sectional schematic view of the mitral valve treated with the transvalvular band of FIG. 37 and an Alfieri type procedure.

Although the method of implanting and positioning the transvalvular band 50 has been illustrated with one embodiment of the transvalvular band 50, other embodiments as described above can also be used. For example, FIG. 36 illustrates a transvalvular band 50 with a wider, offset coaptive edge support portion 66 that has been implanted in the mitral valve annulus. As shown, the coaptive edge support 66 is offset so that it positioned to support the coaptive edge of the mitral valve 18. In addition, the transvalvular band 50 can be used in conjunction with other devices and procedures, such as a separate or integrally attached annular or annuloplasty ring described above. In addition, the transvalvular band 50 can be used in conjunction with the Alfieri procedure, where the tips of the mitral valve leaflets 24 and 26 are sutured 74 together, as shown in FIG. 38.

Figure 37:
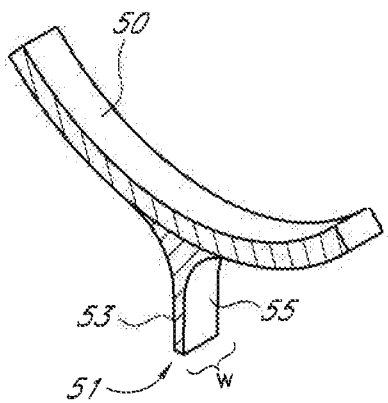
FIG. 37 is a cross-sectional view of a transvalvular band with a transverse leaflet support.

Referring to FIG. 37, there is illustrated a perspective view of a transvalvular band 50 having a transverse projection or support 51 extending in the direction of the ventricle or in the direction of diastolic blood flow, which could be considered antegrade. The support 51 has a width W, which may be at least about 3 mm, and in some embodiments, at least about 5 mm, and in other embodiments at least about 1.0 cm. The projection 51 may be utilized without an Alfieri stitch, so that the leaflets of the mitral valve close against opposing side walls 53 and 55 of the projection 51. The projection 51 thus helps center the closure of the leaflets, as well as controlling the width of coaption. In addition, the band 50 is illustrated as convex in the direction of the ventricle, to accomplish early closure as has been discussed herein.

The transvalvular band in accordance with the present invention can be implanted via an open surgical procedure, via thoracotomy (e.g. transapically) or alternatively, via a percutaneous procedure using a translumenally implantable embodiment. In the translumenally implantable embodiment, one or more transvalvular bands can be attached to a self-expandable support structure, such as a self-expandable ring or self-expandable stent having a relatively short axial length relative to its expanded diameter. The transvalvular band and the compressed self-expandable support structure are loaded into a catheter with a retractable outer sheath which is inserted percutaneously and advanced translumenally into or across the mitral valve. The retractable outer sheath can be retracted to allow the self-expandable support structure to expand adjacent or against the annulus, thereby positioning the one or more transvalvular bands in about the plane of the mitral annulus. Each transvalvular band can be characterized by a longitudinal axis, and the transvalvular band is oriented in the mitral valve such that the longitudinal axis of the transvalvular band in oriented substantially transversely to the coaptive edge of the mitral valve.

By "percutaneous" it is meant that a location of the vasculature remote from the heart is accessed through the skin, such as using needle access through, for example, the Seldinger technique. However, it may also include using a surgical cut down procedure or a minimally invasive procedure. The ability to percutaneously access the remote vasculature is well-known and described in the patent and medical literature.

Depending on the point of vascular access, the approach to the mitral valve may be antegrade and require entry into the left atrium via the pulmonary vein or by crossing the interatrial septum. Alternatively, approach to the mitral valve can be retrograde where the left ventricle is entered through the aortic valve. Once percutaneous access is achieved, the interventional tools and supporting catheter(s) will be advanced to the heart intravascularly where they may be positioned adjacent the target cardiac valve in a variety of manners, as described elsewhere herein. While the methods will preferably be percutaneous and intravascular, many of the implants and catheters described herein will, of course, also be useful for performing open surgical techniques where the heart is beating or stopped and the heart valve accessed through the myocardial tissue. Many of the devices will also find use in minimally invasive procedures where access is achieved thorascopically and where the heart will usually be stopped but in some instances could remain beating.

Figure 39:
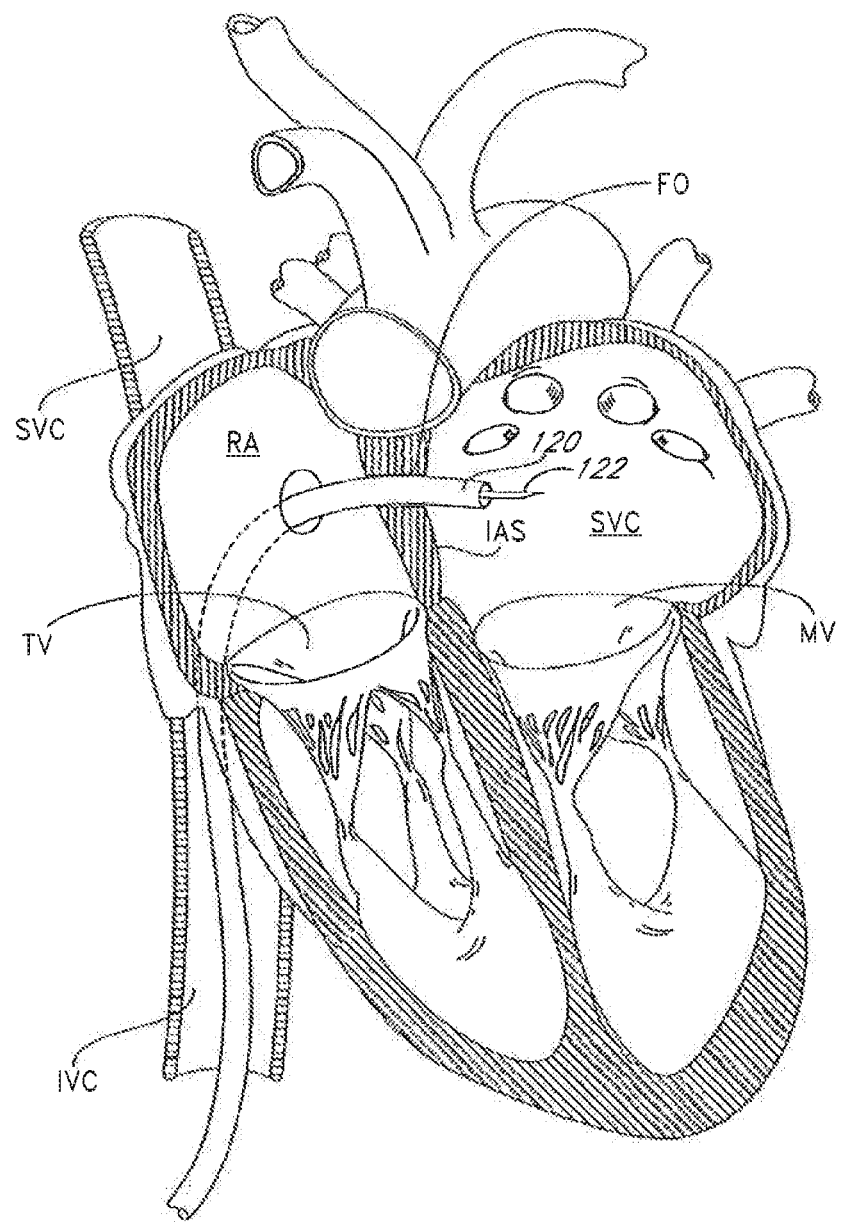
FIG. 39 is a schematic cross-sectional view of the heart, showing a typical antegrade approach to the mitral valve by way of a transseptal crossing.

A typical antegrade approach to the mitral valve is depicted in FIG. 39. The mitral valve MV may be accessed by a standard approach from the inferior vena cava IVC or superior vena cava SVC, through the right atrium RA, across the interatrial septum IAS and into the left atrium LA above the mitral valve MV. As shown, a catheter 120 having a needle 122 may be advanced from the inferior vena cava IVC into the right atrium RA. Once the catheter 120 reaches the interatrial septum IAS, the needle 122 may be advanced so that it penetrates through the septum at the fossa ovalis FO or the foramen ovale into the left atrium LA. At this point, a guidewire may be advanced out of the needle 122 and the catheter 120 withdrawn.

Figure 40:
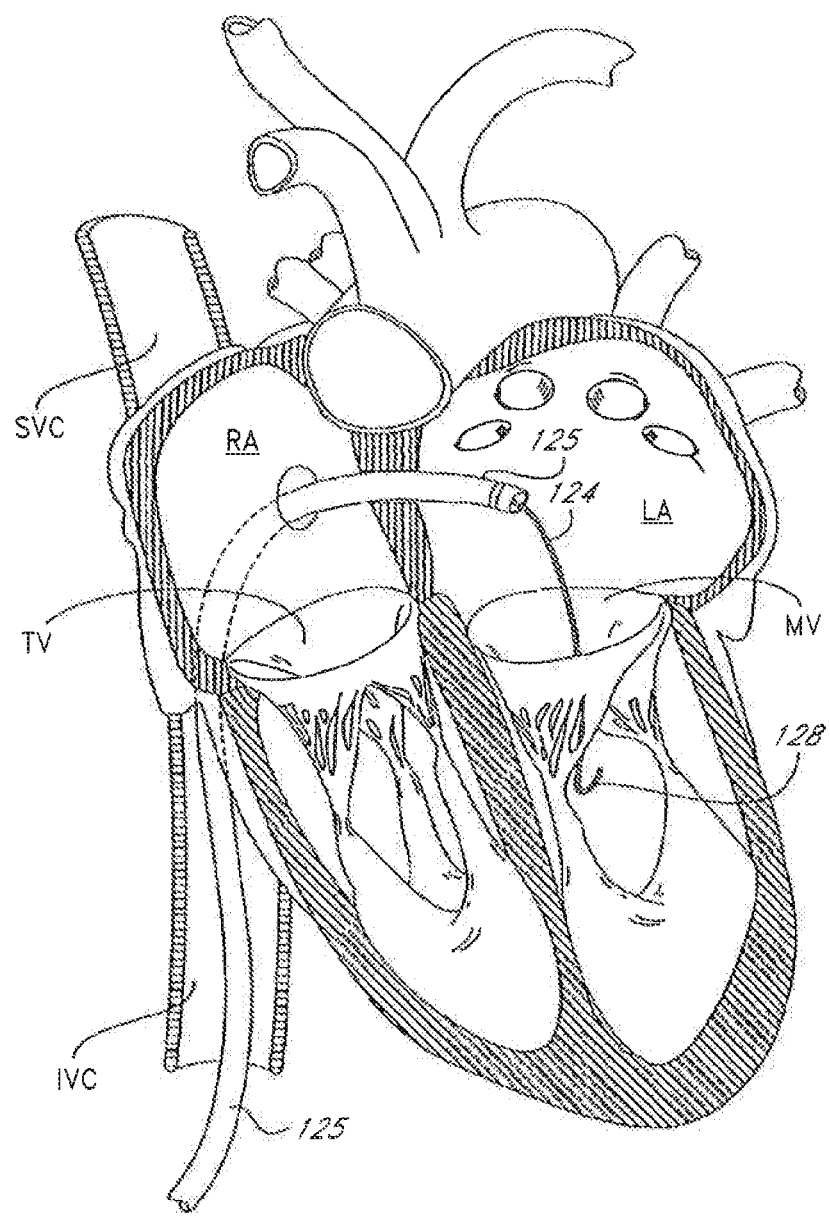
FIG. 40 is a cross sectional view as in FIG. 39, showing placement of a guidewire through the mitral valve.

As shown in FIG. 40, access through the interatrial septum IAS will usually be maintained by the placement of a guide catheter 125, typically over a guidewire 124 which has been placed as described above. The guide catheter 125 affords subsequent access to permit introduction of the tool(s) which will be used for performing the valve or tissue modification, as described in more detail below.

Figure 41:
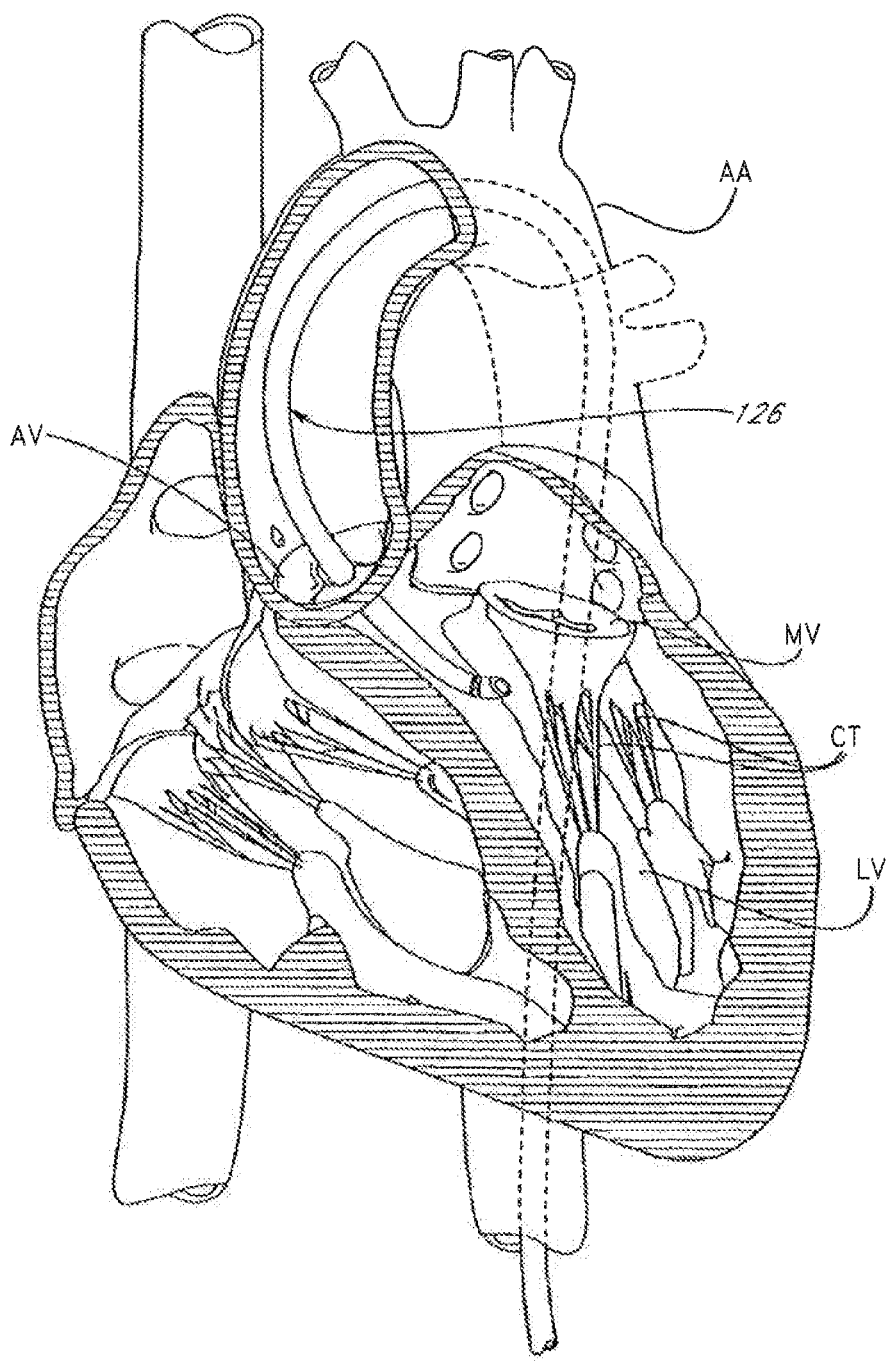
FIG. 41 is a cross sectional view of the heart showing a typical retrograde approach to the mitral valve by way of a femoral artery access.
Figure 42:
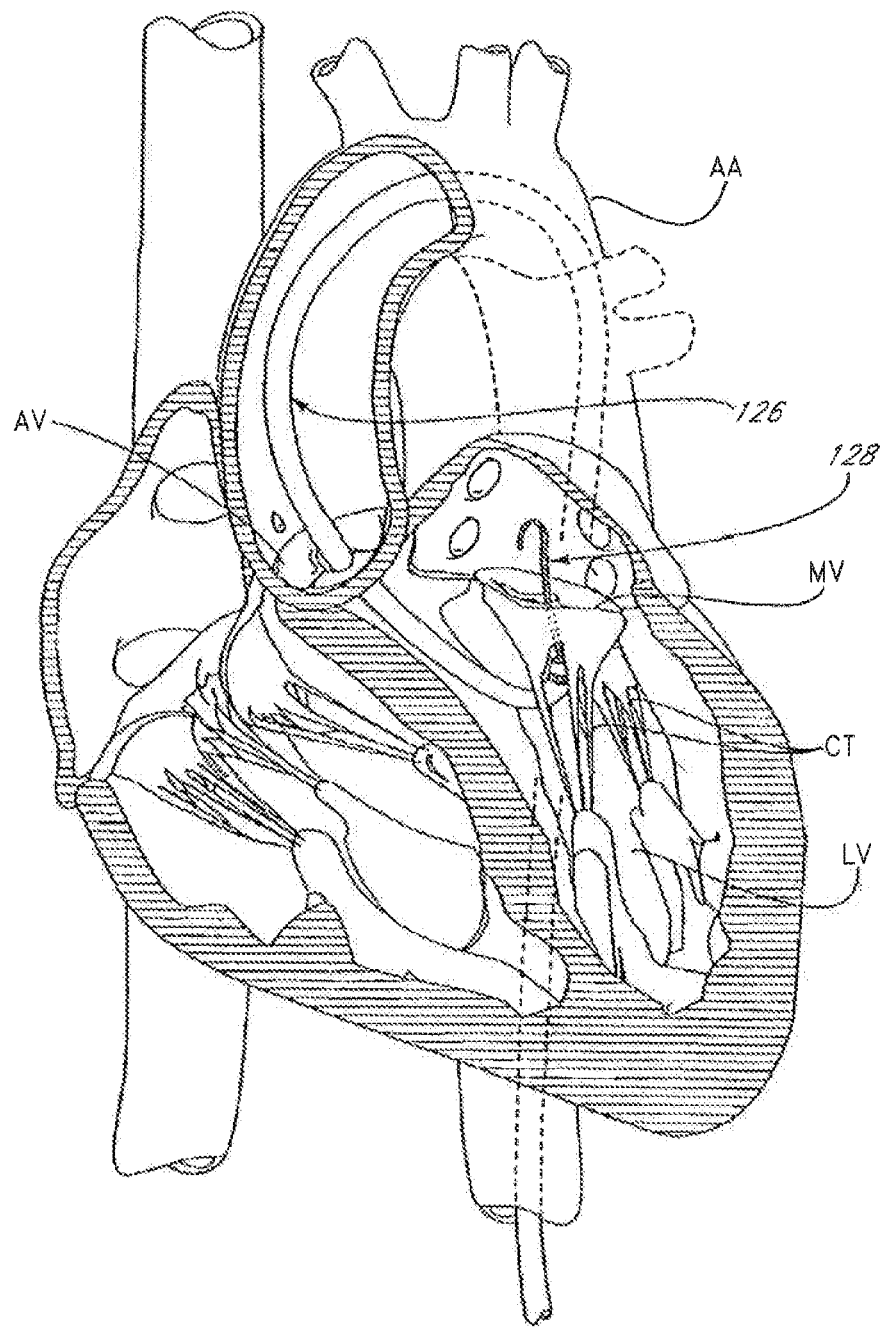
FIG. 42 shows a retrograde approach as in FIG. 41, with a guidewire placed across the mitral valve.

A typical retrograde approach to the mitral valve is depicted in FIG. 41. Here the mitral valve MV may be accessed by an approach from the aortic arch AA, across the aortic valve AV, and into the left ventricle below the mitral valve MV. The aortic arch AA may be accessed through a conventional femoral artery access route, as well as through more direct approaches via the brachial artery, axillary artery, or a radial or carotid artery. As shown in FIG. 42, such access may be achieved with the use of a guidewire 128. Once in place, a guide catheter 126 may be tracked over the guidewire 128. The guide catheter 126 affords subsequent access to permit introduction of the tool(s) which will be used for performing the valve modification, as described in more detail below.

In some cases, access routes to the mitral valve may be established in both antegrade and retrograde approach directions. This may be useful when, for instance, grasping is performed with the use of specific devices introduced through one route and fixation is achieved with the use of separate devices introduced through another route. In one possible situation, the transvalvular band may be introduced via a retrograde approach. While the transvalvular band is held in place, a fixation tool may be introduced via an antegrade approach to fix the transvalvular band in place. The access pathways for the transvalvular band and fixation tool may alternatively be reversed. Thus, a variety of access routes may be used individually or in combination with the methods and devices of the present invention.

Figures 43A, 43B, 43C:
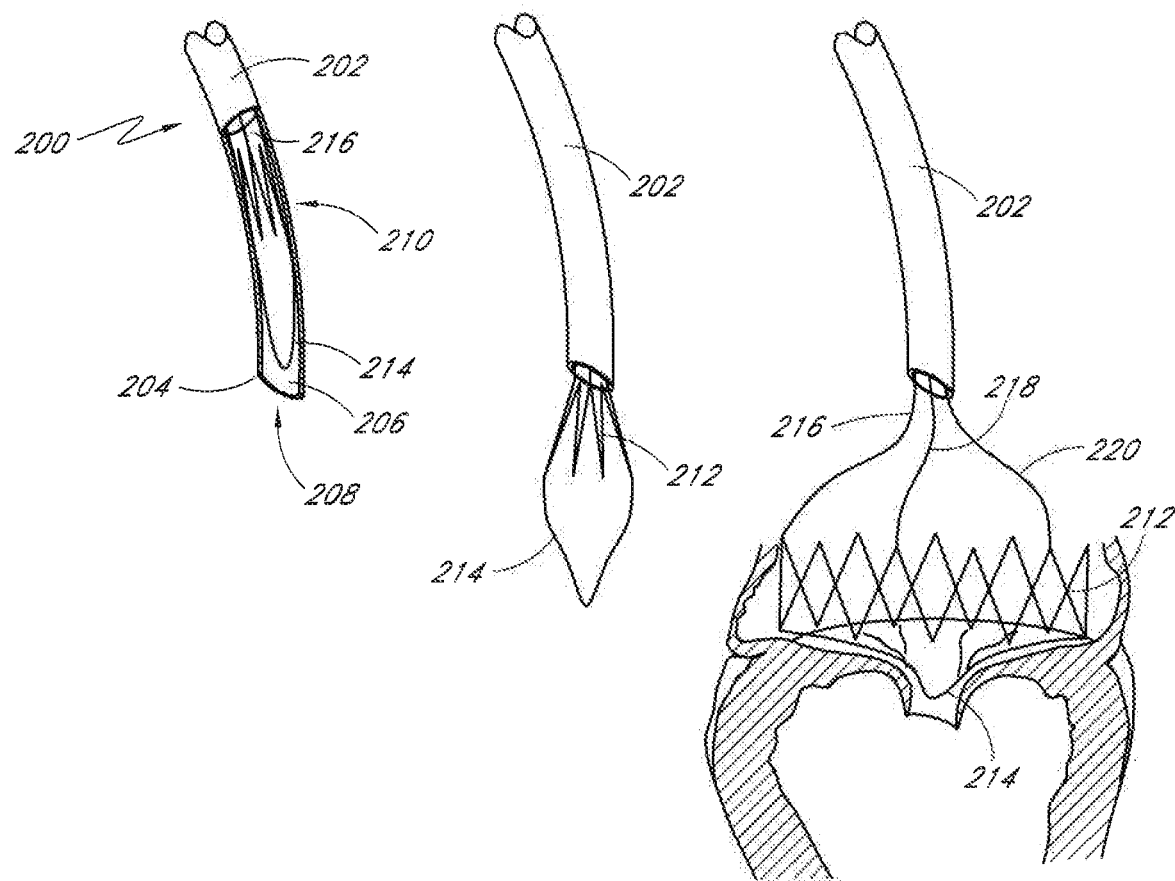
FIG. 43A is a schematic view of the distal end of a percutaneous deployment catheter having a self-expandable implant positioned therein.
FIG. 43B is a schematic view as in FIG. 43A, with the implant partially deployed from the catheter.
FIG. 43C is a schematic view of the deployment catheter showing the implant fully expanded at the deployment site, but still tethered to the deployment catheter.

Referring to FIG. 43A, there is illustrated a schematic view of a percutaneously deliverable implant in accordance with one aspect of the present invention. The deployment system includes a deployment catheter 200, only a distal end of which is illustrated herein. Deployment catheter 200 is configured in accordance with known technology for accessing the mitral valve, utilizing conventional dimensions and the materials known to those of skill in the art. In general, the deployment catheter 200 comprises an elongate flexible tubular body 202 extending between a proximal end (not illustrated) and a distal end 204. The proximal end is provided with a proximal manifold, including access portals such as luer connectors in communication with each functional lumen in the catheter 200.

The distal end 204 is provided with a distally facing opening 208, which is in communication with the proximal end via a central lumen 206.

Positioned within the central lumen 206 is a collapsed implant 210. Implant 210 is transformable between a first, radially reduced configuration such as for positioning within the deployment catheter 200 and a second, radially enlarged configuration (see FIG. 43C) for positioning at the treatment site. Transformation of the implant from the first configuration to the second configuration may be accomplished under positive force, such as via balloon dilatation. Alternatively, as illustrated herein, transformation is accomplished by self-expansion of the implant 210 in response to removal of the constraint provided by the tubular body 202.

In general, the implant 210 comprises a frame or anchor component 212 and a leaflet support component 214. Leaflet support component 214 may comprise any of a variety of structures similar to those described previously herein as the annular band, configured or reconfigured such that the annular band may be radially reduced for positioning within a deployment catheter and subsequently radially enlarged for spanning the mitral valve. The implant 210 additionally comprises an anchor component, for anchoring the leaflet support 214 at the treatment site. In the illustrated embodiment, anchor 212 is schematically illustrated as a zigzag wire or filament structure, which is radially expansible following removal of the constraint. However, any of a variety of configurations may be utilized for the anchor 212.

Referring to FIG. 43B, the outer tubular flexible body 202 is shown partially retracted from the implant, permitting the implant to begin to radially expand. FIG. 43C illustrates further retraction of the tubular body 202, to fully release the anchor 212 at the deployment site. As illustrated, anchor 212 radially expands within the left atrium. The leaflet support 214 extends approximately transversely to the coaptive edge of the mitral valve leaflets, and is convex or inclined in the direction of the mitral valve to advance the coaptation of the mitral valve leaflets in the direction of the ventricle as has been described elsewhere herein.

As seen in FIG. 43A, the implant 210 is controlled by at least one control line 216. Control line 216 extends throughout the length of the deployment catheter 200, and to at least one control on or near the proximal manifold. This enables proximal retraction of the flexible body 202 with respect to the implant 210, and control of implant 210 prior to final detachment from the deployment system.

Referring to FIG. 43C, at least a first control wire 216, a second control wire 218, and a third control wire 220 are illustrated connected to the anchor 212. Control wires 216, 218 and 220 enable manipulation of the implant into its final desired position, and, if necessary, proximal retraction of the implant back within the deployment catheter should the decision be made to remove the implant prior to final detachment.

Prior to final detachment of the implant 210, additional anchoring structures may be engaged to retain the implant at its desired implanted location. For example, anchor 212 may be provided with any of a variety of tissue anchors or barbs, for engaging the mitral valve annulus or the base of the leaflets or other adjacent anatomical structures. Alternatively, separate tissue anchors may be advanced through the deployment catheter 200, and utilized to secure the anchor 212 to the adjacent tissue. Suitable anchors are preferably enlargeable from a first, reduced cross sectional configuration for traveling through the deployment catheter 200 and piercing tissue, to a second, enlarged configuration for resisting removal from the tissue. In the embodiment illustrated in FIG. 43C, no secondary anchoring structures are illustrated for simplicity.

Once the position of the implant 210 has been verified and found acceptable, and the determination of whether to introduce secondary anchoring structures has been made, the control wires 216, 218 and 220 are detached from the anchor 212, and the deployment catheter 200 is removed from the patient. Detachment of the control wires from the implant 210 may be accomplished in any of a variety of ways, such as by electrolytic detachment, detachment by thermal elevation of a softenable or meltable link, mechanical detachment such as by rotating the control wire such that a threaded end of the control wire is threadably disengaged from the anchor 212, or other detachment techniques depending upon the desired functionality and profile of the system.

Figure 43D:
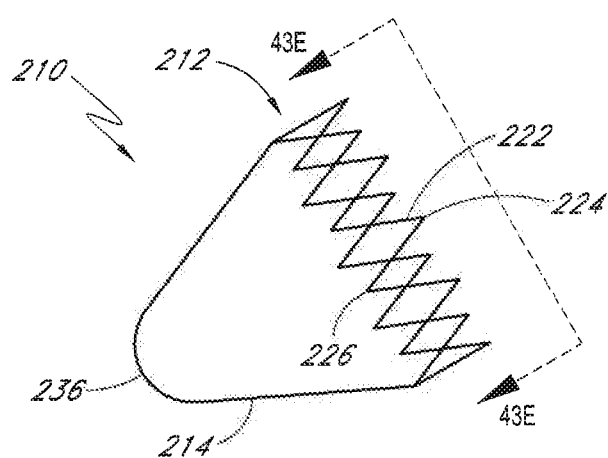
FIG. 43D is a side elevational view of the implant of FIG. 43C.

Referring to FIG. 43D, there is illustrated a side elevational view of the implant 210 in an unconstrained (e.g., bench top) expanded configuration. The anchor 210 comprises a plurality of struts 222, which are joined at a first end by a plurality of apices 224 and a second end by a plurality of apices 226 to produce a zigzag structure sometimes referred to as a "Z stent" configuration. This configuration is convenient and well understood in the intravascular implant arts, although any wide variety of structures may be utilized. For example, zigzag wire patterns, woven wire patterns, or sinusoidal wire patterns may be utilized. Laser cut wall patterns such as from tubing stock may also be utilized, and may be provided with any of a wide variety of complex wall patterns. In general, nickel titanium alloys such as any of a variety of nitinol alloys are preferred. However, depending upon the wall pattern, stainless steel, elgiloy, certain polymers or other materials may also be utilized. Heat treatment may be required to anneal and shape set an alloy such as Nitinol. Other alloys may require only annealing to relieve stresses incurred during prior processing.

Figure 43E:
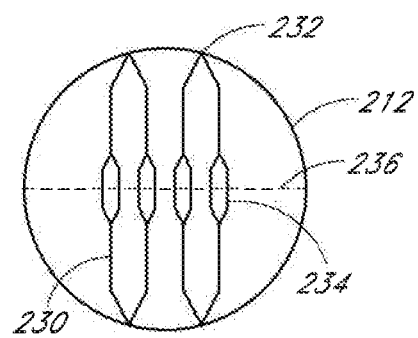
FIG. 43E is an end view taken along the line 43E-43E of FIG. 43D.

Referring to FIG. 43E, there is illustrated an end view of the implant shown in FIG. 43D to show the transverse configuration of the transvalvular band portion of the implant. In this illustration, the transvalvular band comprises a plurality of struts 230 which are connected to the anchor 212 at junctions 232. Struts 230 may in turn be divided into a bifurcated section 234 or other configuration to increase the effective footprint of the transvalvular band measured along the coaptive edge of the valve, while minimizing obstruction to blood flow therethrough. The coaptive edge of the valve, as implanted, will preferably be approximately aligned with the transverse axis 236 illustrated in FIG. 43E of the band, as implanted. The axis of coaption of the mitral valve is preferably parallel to axis 236 in the implanted configuration, but may be within about 45°, preferably within about 20°, and most preferably within about 10° of the axis 236.

Referring to FIGS. 44A and 44B, there is illustrated an anchor deployment catheter which may be utilized to provide either primary or secondary anchoring of the anchor structure 212 to adjacent tissue. Anchor deployment catheter 250 comprises an elongate flexible tubular body 252, configured to access the vicinity of the mitral valve. Tubular body 252 extends between a proximal end 254 and a distal end 256. Distal end 256 is provided with a distal opening 258, enabling access to a central lumen 260. An elongate flexible core wire 262 extends from the proximal end 254 throughout most of the length of the lumen 260 to a distal surface 264. See FIG. 44C. The proximal end of the core wire 262 is provided with a control 266 that enables axial reciprocal movement of the core wire 262 within the central lumen 260.

A tissue anchor 268 may be positioned within the distal end of the delivery catheter 250. In use, manipulation of the control 266, such as by distal axial advance relative to the tubular body 252, distally, axially advances the core wire 262 to expel the anchor 268 through the distal opening 258. Distal opening 258 is preferably provided with a bevel or angled cut to provide a sharpened distal tip 270. This enables distal axial advance of the distal tip 270 into tissue at a desired site, so that the control 266 may be manipulated to deploy all or a portion of the anchor 268 into the target tissue.

Any of a variety of tissue anchors 268 may be utilized, depending upon the desired configuration of the implant and the implant anchor interface. In the illustrated embodiment, the anchor 268 is configured as a double "t-tag" anchor. A first tissue engaging element 272 is connected to a second implant engaging element 274 by a filament 276. In use, the distal tip 270 is positioned within the tissue of the mitral valve annulus. Control 266 is manipulated to deploy the first element 272 beneath the surface of the tissue. The tubular body 252 is thereafter proximally retracted, enabling the second element 274 to engage the implant and retain it against the adjacent tissue.

The anchor delivery catheter 250 may be advanced through the deployment catheter 200, and/or along a guide such as a guidewire or support wire. In the illustrated embodiment, the anchor deployment catheter 250 is provided with a guide lumen 278 allowing the anchor delivery catheter to track along a guidewire. Guide lumen 278 is defined by a tubular wall 280. Tubular wall 280 may extend the entire length of the anchor delivery catheter 250, such as by forming the catheter body as a dual lumen extrusion. Alternatively, tubular wall 280 may be provided with an axial length that is short relative to the overall length of the catheter, such as no more than about 3 cm and preferably no more than about 2 cm in length. This allows the anchor delivery catheter to ride along a guidewire in a monorail or rapid exchange manner as will be illustrated below.

Referring to FIGS. 45A and 45B, there is illustrated an implant configured for use with the anchor delivery catheter described above. In general, the implant comprises a first leaflet support 292 and a second leaflet support 294, separated by a flexible connection 296. Flexible connection 296 permits the implant 290 to be folded within a deployment catheter, and later expanded in a manner that permits the implant 290 to function as a transvalvular band as described. The implant 290 may be manufactured in any of a variety of ways, such as using a wire frame or by laser cutting from sheet stock as will be appreciated by those of skill in the art.

In the illustrated embodiment, a first and second flexible connection 296 reside in a plane configured to be substantially parallel to the axis of coaption the as implanted orientation. The lateral edges of the each of the first leaflet support 292 and second leaflet support 294 are provided with at least one and preferably two or three eyes 298, fabric patches, or other anchor attachment structure, for receiving a tissue anchor.

Referring to FIG. 45B, the implant of FIG. 45A is illustrated in a partially collapsed configuration, flexed about the flexible connection 296. In addition, control wires 300, 302 and 304 are illustrated releasably connected to the implant 290. Control wires 300, 302 and 304 may be utilized to advance the implant 290 from the deployment catheter such as catheter 200 described above, and manipulate the implant until the anchors have been fully deployed. Thereafter, control wires 300, 302 and 304 may be removed such as by electrolytic detachment, melting a polymeric link, unscrewing a threaded connection, or other detachment mechanism depending upon the desired functionality of the device.

Referring to FIGS. 46A through 46E, there is illustrated a sequence of deploying an implant at the mitral valve from an antegrade direction. The implant 290 may be similar to that illustrated in FIGS. 45A and 45B, or have wall patterns or characteristics of other implants disclosed elsewhere herein. In general, the implant 290 is deployed from the catheter 200 in the sequence illustrated in FIGS. 46A through 46C. The surrounding anatomy has been eliminated for simplicity.

Figure 46A:
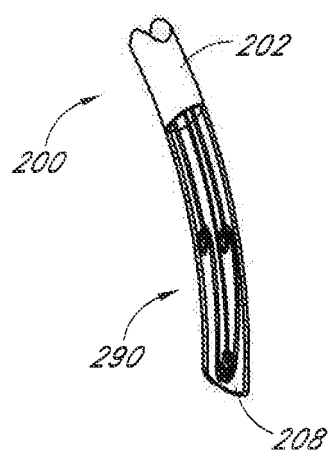
FIG. 46A is a cut-away perspective view of the distal end of a deployment catheter having a self-expandable implant contained therein.
Figure 46B:
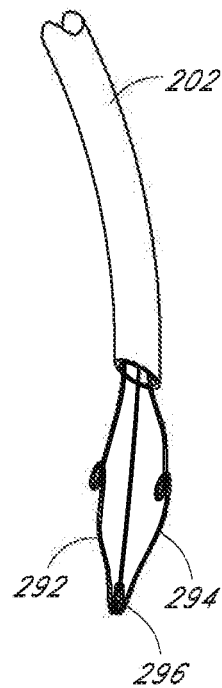
FIG. 46B is a deployment catheter as in FIG. 46A, with the implant partially deployed.
Figure 46C:
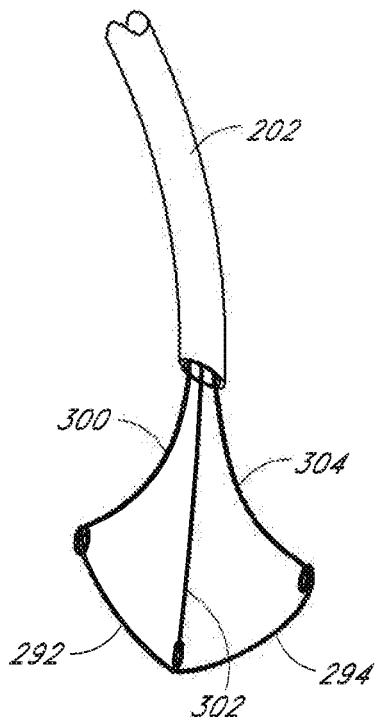
FIG. 46C is a view as in FIG. 46B, showing the implant released from the deployment catheter, but connected to three control wires.
Figure 46D:
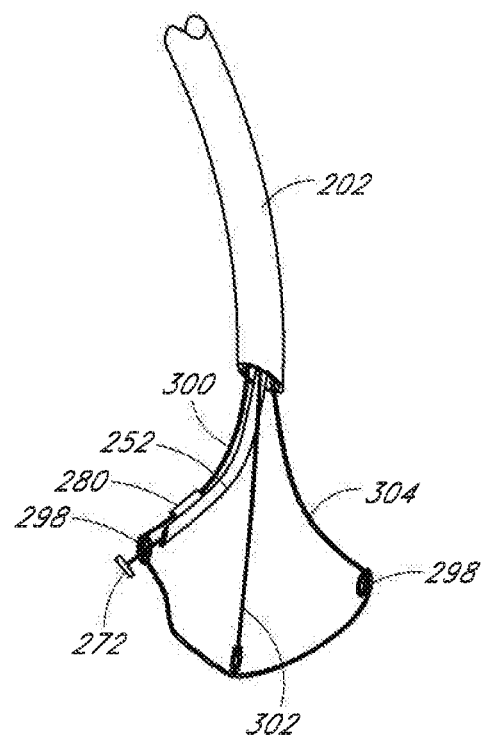
FIG. 46D is a view as in FIG. 46C with a tissue anchor deployment catheter.

Referring to FIG. 46D, the anchor delivery catheter 250 is advanced onto the proximal end of one of the control wires 300, such that the control wire 300 is axially moveably positioned within guide lumen 278. This enables the anchor delivery catheter 250 to be advanced along the control wire 300 in a monorail or rapid exchange configuration as is understood in the catheter arts. Anchor delivery catheter 250 is advanced along the control wire 300 until the distal tip 270 advances through the eye 298 or fabric tab or other attachment structure, and into the adjacent tissue of the base of the mitral valve leaflet or mitral valve annulus. The control 266 is manipulated such as by distal advance to advance the first anchor element 272 out of the distal opening 258 and into the tissue as illustrated in FIG. 46D.

The anchor delivery catheter 250 is thereafter proximally withdrawn to position the distal opening 258 on the device proximal side of the eye 298, and the core wire 262 is further distally advanced to deploy the second anchor element 274 from the distal opening 258 of the anchor delivery catheter 250. Anchor delivery catheter 250 may thereafter be proximally withdrawn from the patient. Either the same or a different anchor delivery catheter 250 may thereafter be advanced along the third control wire 304, enabling deployment of another tissue anchor as is illustrated in FIG. 46E.

Figure 46E:
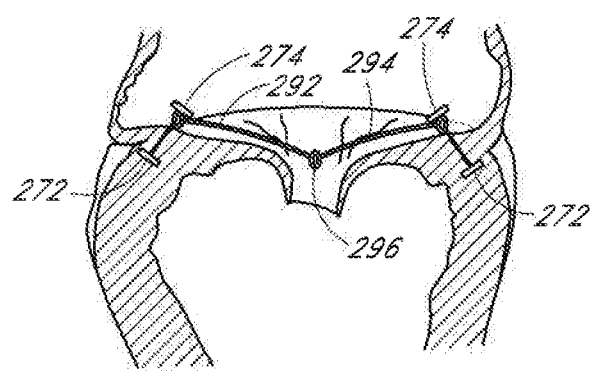
FIG. 46E is a cross sectional view of a mitral valve, having an implant anchored in place and the deployment catheter removed.

The implant 290 is illustrated in FIG. 46E as having a central portion inclined in the direction of the ventricle to support the leaflets as has been discussed elsewhere herein. This configuration may be retained by the inherent bias built into the structure and materials of the implant 290. Alternatively, the configuration of inclining in the direction of the ventricle may be retained by active intervention such as by providing a mechanical interlock, in situ heat weld with capacitive discharge/electrolytic weld, application of a clip or other locking structure by way of control wire 302 or simply by the mechanical forces attributable to the mitral valve annulus, which prohibit lateral expansion of the device sufficient for the flexible connection 296 to invert in the direction of the atrium. Alternatively, an implantable control wire (not illustrated) may be introduced, to connect the implant 290 such as in the vicinity of the flexible connection 296 to the opposing wall of the ventricle, as will be described in connection with a transapical implementation of the invention described below.

A further implementation of the invention is illustrated in connection with FIGS. 47A through 47E. Referring to FIG. 47A, the first control line 300 and third control line 304 have been replaced by a first guide tube 310 and a second guide tube 312. First guide tube 310 and second guide tube 312 each has the double function of controlling deployment of the implant, as well as enabling introduction of a tissue anchor therethrough. This avoids the use of a separate tissue anchor deployment catheter such as that described above.

As illustrated in FIG. 47B, once the implant is provisionally positioned in the vicinity of the mitral valve, a first tissue anchor 314 is deployed through the first guide tube 310. A second tissue anchor 316 is deployed through the second guide tube 312. The tissue anchors may comprise "T" tag type constructions, pigtail or corkscrew constructions, or any of a variety of other soft tissue anchors known in the art. In general, tissue anchors utilized for the present purpose are preferably transformable from a first, reduced cross-sectional configuration to a second, radially enlarged cross-sectional configuration to enable deployment through a small needle or tube and then provide a relatively higher resistance to pull out. Radial enlargement may be accomplished by angular movement of a portion of the anchor, or by physical expansion in a radial direction.

Referring to FIG. 47C, the first guide tube 310 and second guide tube 312 have been removed following deployment of the tissue anchors. The guide tubes may be removed using any of a variety of detachment techniques disclosed elsewhere herein. Either before or after removal of the guide tubes, distal pressure on either the tubular body 202 or the control wire 302 inverts the implant from the configuration shown in FIG. 47C to the final configuration shown in FIGS. 47D and E. The inverted configuration of FIGS. 47D and E may be retained by the mechanical bias imparted through the anchoring to the mitral valve annulus, or using techniques described elsewhere herein. The control wire 300 is thereafter detached from the implant, as illustrated in FIG. 47E.

Any of a variety of the implants of the present invention may alternatively be introduced across the ventricle, such as in a transapical approach. The retrograde approach to the mitral valve will necessitate certain modifications to both the implant and the deployment system, as will be appreciated by those of skill in the art in view of the disclosure herein.

For example, a transventricle approach is illustrated in FIGS. 48A through 48D. A deployment catheter 320 is introduced into the ventricle, and retrograde through the mitral valve to position the distal opening 208 within the atrium. An implant is carried within the deployment catheter 320, as has been described elsewhere herein. In general, the implant comprises a first leaflet support 292 and a second leaflet support 294 separated by a flexible zone or pivot point.

In the retrograde implementation of the invention, the first and second leaflet supports are flexible or pivotable with respect to the longitudinal axis of the control wire 300, such that they may be moved between a first configuration in which there are substantially parallel with the axis of the control wire 300, and a second position, as illustrated in FIGS. 48A through 48D, in which they are inclined radially outwardly from the longitudinal axis of the control wire 300 in the device proximal direction. The implant may thus reside within the deployment catheter 320 when the first leaflet support 292 and second leaflet support 294 are in the first, reduced crossing profile configuration, with each of the tissue anchors 314 and 316 pointing in a device proximal direction. In this embodiment, the tissue anchor 314 may be permanently affixed to or integral with the first leaflet support 292 and the second anchor 316 may be similarly carried by the second leaflet support 294.

Once the distal end of the deployment catheter 320 has been positioned within the atrium, the control wire 300 may be distally advanced to advance the anchors 314 and 316 beyond the distal opening 208. This releases the implant and allows the angle between the first and second leaflet supports to be increased, so that the tissue anchors 314 and 316 may be aimed at the desired tissue anchor target sites. Proximal retraction on the control wire 300 may be utilized to seat the tissue anchors within the target tissue, as illustrated in FIG. 48B.

Figure 48D:
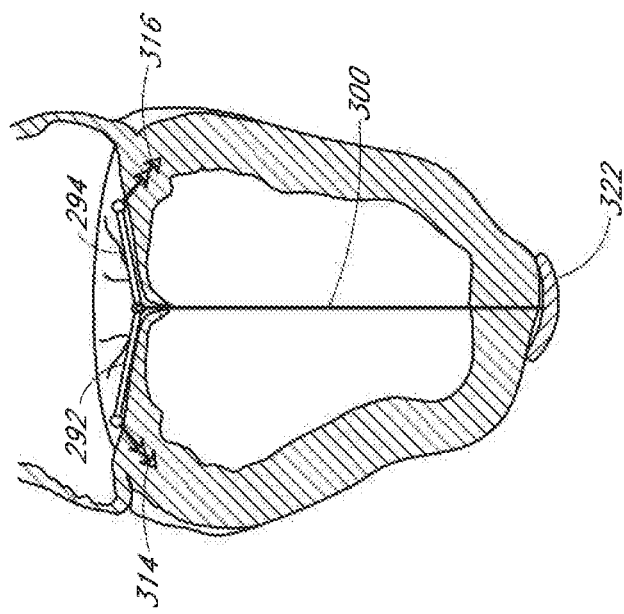
FIG. 48D is a schematic view as in FIG. 48C, in an embodiment having a transventricular support.
Figure 48C:
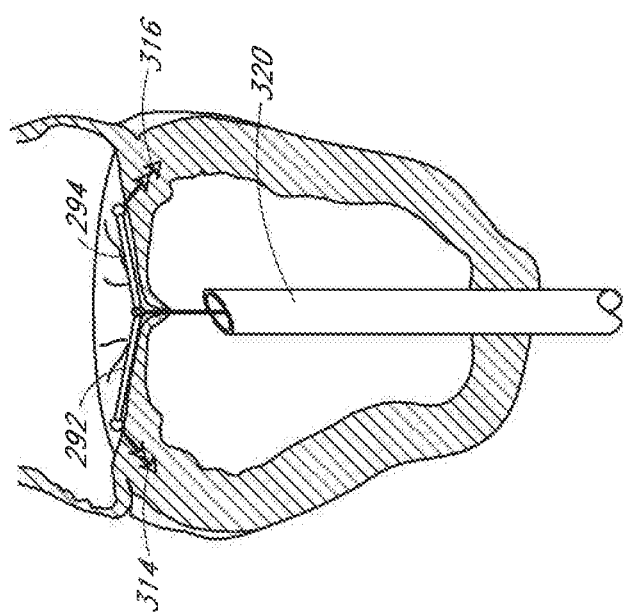
FIG. 48C is a schematic view as in FIG. 48B, with the deployment catheter withdrawn through the mitral valve.

Further proximal traction on the control wire 300 may be utilized to invert the implant into the configuration illustrated in FIG. 48C. At that point, the control wire 300 may be severed from the implant as has been discussed elsewhere herein. Alternatively, the deployment catheter 320 may be proximally retracted leaving the control wire 300 secured to the implant, and a second portion of the control wire may be secured to a tissue anchor 322 within or on the epicardial surface of the ventricle. Anchor 322 may comprise any of a variety of structures, such as a pledget, button, or other structure that provides a footprint against the epicardial surface to resist retraction of the control wire 300 into the ventricle. The control wire 300 may thereafter be severed proximally of its securement to the anchor 322, leaving the control wire 300 and anchor 322 in position to span the ventricle and retain the configuration of the implant as illustrated in FIG. 48D.

In all the foregoing embodiments, the final configuration of the implant within the mitral valve is illustrated in a highly schematic form, and the angle and degree of inclination into the direction of the ventricle may be significantly greater than that illustrated herein depending upon the desired clinical performance. The transvalvular band inclination can be highly advantageous in some embodiments in providing clinical benefit as it facilitates "physiologic coaptation" in a preferred manner as its surface mimics the three dimensional feature created by the leaflets as they would have coapted in a healthy native valve.

Figure 49H:
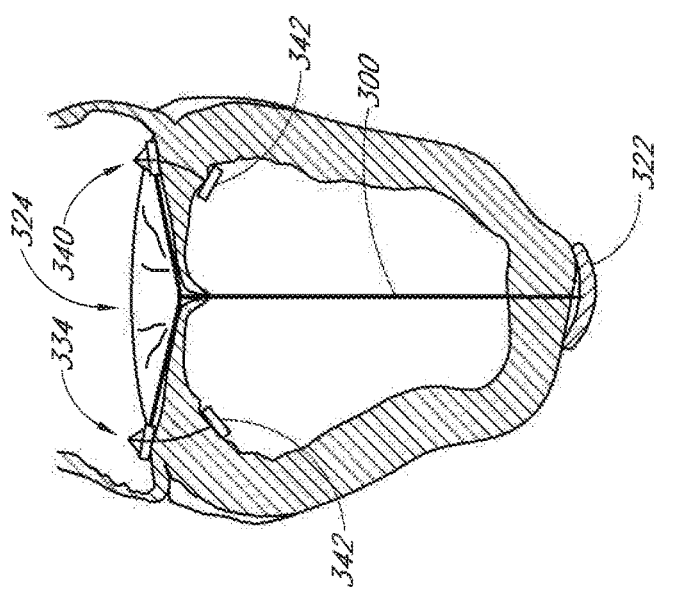
FIG. 49H shows an alternate end point, in which the transvalvular band is additionally provided with a transventricular truss and an epicardial anchor.

Referring to FIGS. 49A through 49H, there is illustrated a transapical approach to the mitral valve, and deployment of a transvalvular band in accordance with the present invention. As illustrated in FIG. 49A, a deployment catheter 320 has been introduced such as via thoracotomy, and advanced retrograde through the mitral valve. A transvalvular band 324 has been deployed distally from the catheter 320, and is illustrated in FIG. 49A in an expanded configuration within the left atrium. Expansion of the transvalvular band 324 from a reduced cross-sectional profile for positioning within the catheter 320 to the enlarged cross-sectional profile illustrated in FIG. 49A may be accomplished either under mechanical force, such as by dilatation of an inflatable balloon or other mechanical mechanism. Preferably, however, transvalvular band 324 is self-expandable so that it converts from the reduced profile to the enlarged profile automatically upon deployment from the distal end of the catheter 320.

In the illustrated embodiment, the transvalvular band 324 comprises an arcuate central portion 325, which is convex in the direction of the ventricle. See FIGS. 49A and 49B. The transvalvular band 324 is provided with a first attachment structure 326 and a second attachment structure 328. Attachment structures 326 and 328 may comprise any of a variety of structures disclosed herein, such as tissue anchors, including hooks or barbs. In one implementation of the invention, the first attachment structure 326, and second attachment structure 328 each comprise a target for receiving an anchor as will be disclosed below. Suitable targets for the present purpose include woven or non-woven fabrics, polymers, or other materials or constructions which permit a needle or sharpened anchor to penetrate therethrough, as will be discussed. In one implementation of the invention, each of the attachment structures comprises a Dacron mesh, having a frame for supporting the mesh and securing the mesh to the transvalvular band 324.

Referring to FIG. 49B, there is illustrated a perspective view of the transvalvular band 324 illustrated in FIG. 49A. The transvalvular band 324 comprises a central section 325, convex in the direction of the ventricle for affecting leaflet closure as has been described herein. Central section 325 is formed by a frame 327, which comprises at least one strut 329 extending between the first attachment structure 326 and second attachment structure 328. In the illustrated embodiment, three struts extend generally parallel to each other, defining at least two elongate openings therebetween. One or two or four or more transverse elements 331 may be provided, such as to enhance structural integrity of the construct. At least a first control wire 300 and, optionally a second or third or fourth control wire 300 is releasably attached to the transvalvular band 324, to enable manipulation of the band into position as shown in FIG. 49C. Control wire 300 is releasably connected to the transvalvular band 324 at a connection point 301. The connection at point 301 may be established by threadable engagement, an electrolytically detachable link or weld, or other detachment mechanism. Electrolytically detachable deployment systems are know, among other places, in the neurovascular embolic coil and stent arts, and suitable systems are disclosed in U.S. Pat. No. 5,976,131 to Guglielmi, et al.; U.S. Pat. No. 6,168,618 to Frantzen; and U.S. Pat. No. 6,468,266 to Bashiri, et al., the disclosures of which are hereby incorporated in their entireties herein by reference The first attachment structure 326 comprises a support 333 carried by the frame 327. In the illustrated embodiment, support 333 comprises an enclosed loop, having a central opening filled or covered by a mesh 337. The support 333 may alternatively comprise any of a variety of structures, such as a single linear element, sinusoidal or zigzag pattern, depending upon the desired performance. In the illustrated embodiment, the support 333 is conveniently provided in the form of a loop, to facilitate holding mesh 337 in a generally planar configuration, and support the mesh so that it may be punctured by an anchor, suture or other retention structure. A second support 335 is similarly provided with a mesh 337, to facilitate attachment. The mesh 337 may conveniently be a layer or pad of Dacron or other material, such as an integration of a silicone core with a Dacron jacket, which facilitates both piercing by an attachment structure, as well as tissue in-growth for long term retention. The first support 333 and second support 335 may comprise a radio opaque material, or be provided with radio opaque markers to enable aiming the anchor deployment system into the mesh 337 under fluoroscopic visualization.

Once the transvalvular band 324 has been brought into the position illustrated in FIG. 49C, the first attachment structure 326 and second attachment structure 328 may be secured to the adjacent tissue using any of a variety of clips, staples, barbs, sutures, or other structure which may be conveniently pierced through the mesh 337 and/or looped around the first and second supports 333, 335. The retention element may be approached from either the side of the left atrium, the ventricle, or epicardially, such as by way of a minimally invasive puncture on the chest wall. In the implementation of the method described below, the example of advancing the retention elements from the left ventricle will be described.

Referring to FIG. 49C, proximal traction on the catheter 320 and on the control wire 300, pulls the transvalvular band 324 snuggly against the left atrial side of the mitral valve, such that the first attachment structure 326 and second attachment structure 328 are seated against the valve annulus.

Referring to FIG. 49D, a first anchor guide 330 and a second anchor guide 332 have been distally advanced from the distal end of the catheter 320. Anchor guides 330 and 332 may be alternatively associated with or carried by the catheter 320 in a variety of ways. For example, the first and second anchor guides 330 and 332, may be pivotably carried by the catheter 320, such that they may be inclined radially outwardly from the longitudinal axis of the catheter in the distal direction.

In the illustrated embodiment, the first and second anchor guides comprise a wire or tube for directing an anchor as will be discussed. The wire or tube of the anchor guide may comprise any of a variety of materials, such as nickel titanium alloys (e.g. nitinol) which may be preset to assume a position similar to that illustrated in FIG. 49D upon distal advance from the catheter 320. The first and second anchor guides may be provided with radio-opaque markers, or may be constructed from a radio-opaque material, to permit fluoroscopic guidance. In the illustrated embodiment, the first and second anchor guides are in the form of tubes, for axially slidably receiving a tissue anchor and tissue anchor deployment structures therein.

Referring to FIG. 49E, a retention element in the form of a first anchor 334 is illustrated as having been distally advanced from the first anchor guide 330, through the tissue in the vicinity of the mitral valve annulus, and through the first attachment structure 326. Penetration of the first anchor 334 through the first attachment structure 326 may be accomplished while providing proximal traction on the control wire 300.

The first anchor 334 is provided with at least one and preferably two or four or more transverse elements 336 to resist proximal retraction of the first anchor 334 back through the opening formed in the first attachment structure 326. The transverse element or surface 336 may be provided on any of a variety of structures, such as an umbrella-type structure, t-tag, barbs, or other anchoring configuration which can pass in a first direction through an opening formed in the first attachment structure 326, but resist retraction in a second, opposite direction, back through the first attachment structure 326.

The transverse element 336 is carried by a filament 338, which extends through the adjacent myocardial tissue. Filament 338 may comprise any of a variety of materials, such as a monofilament or multi-filament structure made from polypropylene, any of a variety of other known suture materials such as polyethylene, or metals such as stainless steel, nitinol, and others known in the art. The filament 338 may be a mono-filament structure or a multi-filament structure which may be braided or woven, depending upon the desired clinical performance. At least a second, similar anchor 340 is introduced on the opposing side of the mitral valve.

Figure 49G:
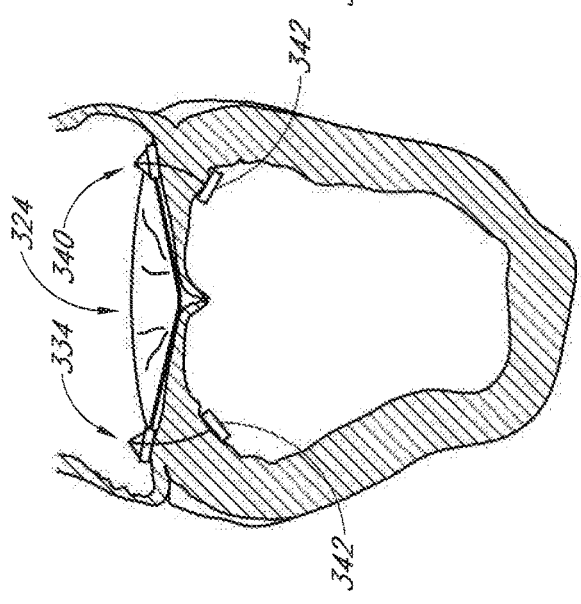
Figure 49F:
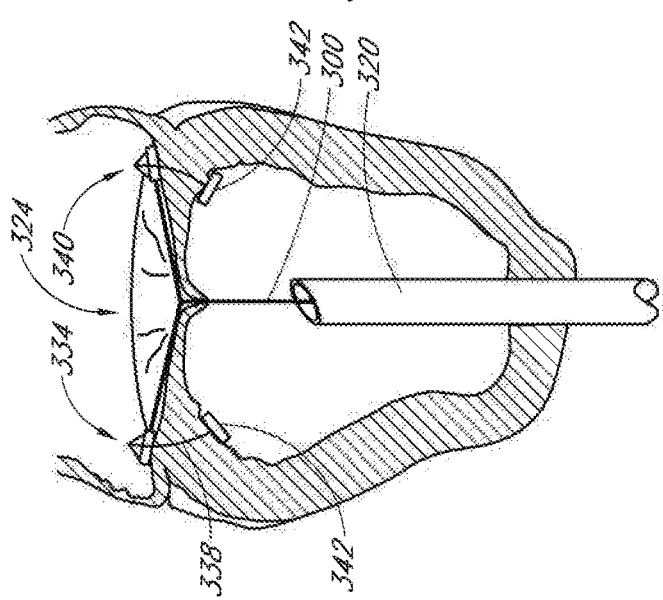

Referring to FIG. 49F, a second transverse element 342 is shown secured to or carried by the ventricular end of the filament 338, to provide a secure anchoring through the tissue wall for the transvalvular band. A similar structure is provided on the opposing side of the mitral valve. Although only a first and second anchoring systems has been described above, additional anchoring systems, such as a total of four or six or eight or more, typically in even numbers to produce bilateral symmetry, may be used. The number and configuration of tissue anchors will depend upon the configuration of the transvalvular band, as will be apparent to those of skill in the art in view of the disclosure herein.

As shown in FIG. 49F, the anchors have been fully deployed and the first anchor guide 330 and second anchor guide 332 have been proximally retracted into the catheter 320.

Referring to FIG. 49G, the control wire 300 may thereafter be detached from the transvalvular band and removed. Detachment of control wire 300 may be accomplished in any of a variety of ways, as has been described elsewhere herein.

Alternatively, the control wire 300 may be left in place as is illustrated in FIG. 49H. Control wire 300 is secured to an epicardial anchor 322, to provide a transventricular truss, as has been described.

Figure 50A:
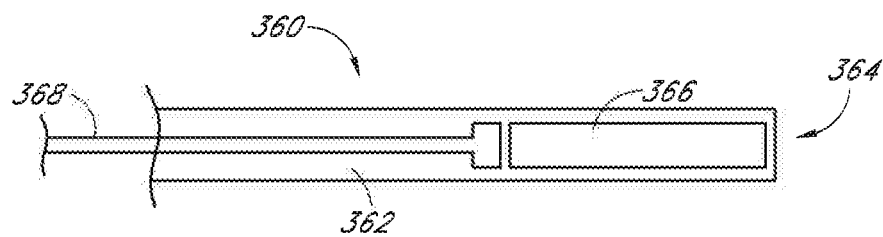
FIG. 50A is a side elevational schematic view of the distal end of a deployment catheter, having a rolled up transvalvular band therein.
Figure 50B:
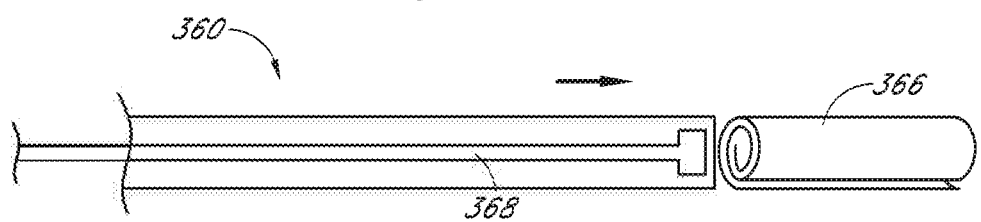
FIG. 50B is an illustration as in FIG. 50A, following distal deployment of the transvalvular band.

Referring to FIGS. 50A and 50B, there is illustrated a side elevational schematic view of the distal end of a deployment catheter 360 which may be adapted for use in either the transapical delivery of FIGS. 49A-49H, or any other delivery mode described herein. In the illustrated embodiment, the deployment catheter 360 includes an elongate tubular body having a central lumen 362, opening at a distal end 364. Carried within the central lumen 362 is a transvalvular band 366, in a rolled-up configuration. Transvalvular band 366 is maintained in a rolled-up configuration by the constraint imposed by the deployment catheter 360. However, upon distal advance of the push element 368 to deploy the transvalvular band 366 beyond the distal end 364, as illustrated in FIG. 50B, the transvalvular band 366 unrolls under its natural bias into a predetermined configuration for implantation across the mitral valve.

Figure 51A:
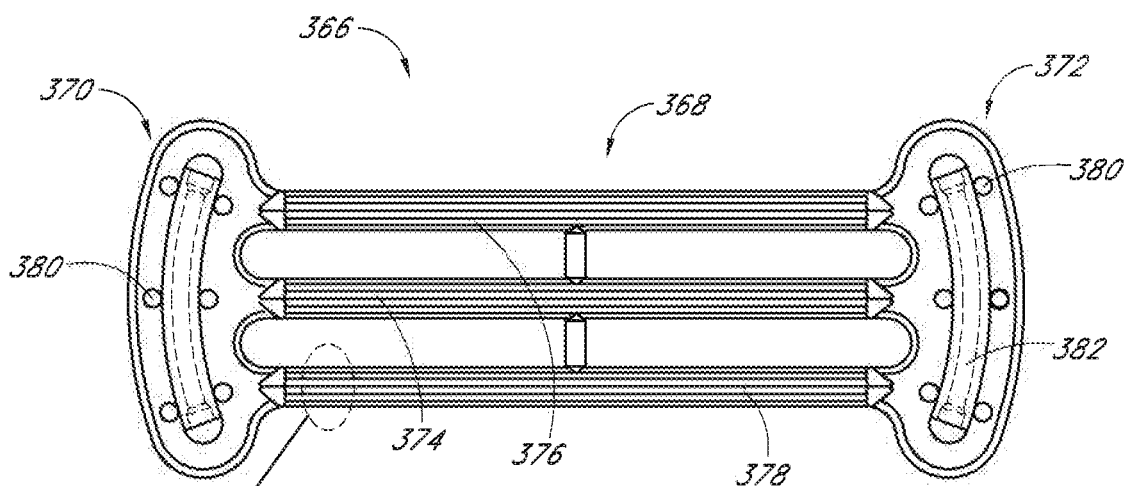
FIGS. 51A and 51B illustrate top plan views and side views of a transvalvular band in accordance with the present invention.

One configuration for the transvalvular band is shown rolled out in plan view in FIG. 51A. However, any of a variety of alternative transvalvular band configurations disclosed herein can be utilized with the catheter of FIGS. 50A and 50B.

Referring to FIG. 51A, there is illustrated a transvalvular band 366 having a central portion 368 for spanning the coaptive edges of the mitral valve. A first attachment zone 370 and a second attachment zone 372 are provided on opposing ends of the central portion 368.

The central portion comprises at least a first strut 374 for spanning the mitral valve as has been discussed. In the illustrated embodiment, a second strut 376 and a third strut 378 are provided, spaced apart to increase the width of the contact footprint with the valve leaflet but permit blood flow therethrough. A first end of each of the struts 374, 376, and 378 are connected at the first attachment zone 370, and the second ends of the three struts are connected at the second attachment zone 372.

The first and second attachment zones may be provided with a reinforcing element 382, to facilitate long term attachment. Apertures 380 are illustrated, which may be provided to allow manual suturing when the transvalvular band 366 is intended for use in an open surgical procedure. Alternatively, apertures 380 may be configured for attachment using an anchor deployment catheter when intended for use in a translumenal or transapical deployment. Each of the first, second and third ribs may be provided with a central core, such as a nitinol or stainless steel wire or ribbon, and an outer coating such as a polycarbonate urethane with or without copolymers like silicone, silicone coating, or a fabric such as PET, ePTFE, polyethylene, or a hybrid of, for example, the aforementioned materials impregnated silicone coating, to reduce the risk of abrasion of the mitral valve leaflets A close-up view of circled zone 51D of FIG. 51A is illustrated in FIG. 51D.

Figure 51B:
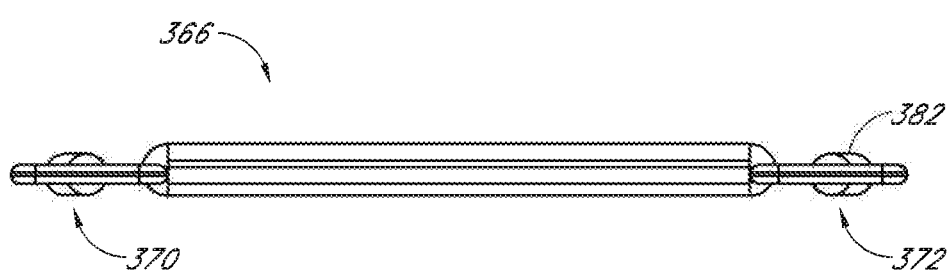
Figure 51C:
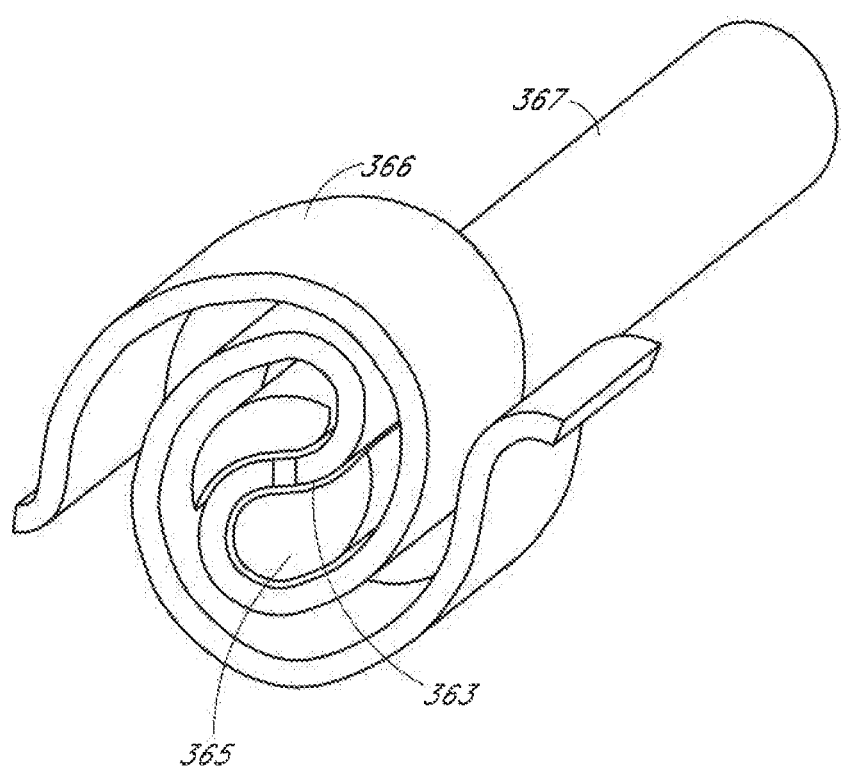
FIG. 51C illustrates a perspective view of one embodiment of a transvalvular band in a rolled-up configuration and mounted on a delivery mandrel.
Figure 51D:
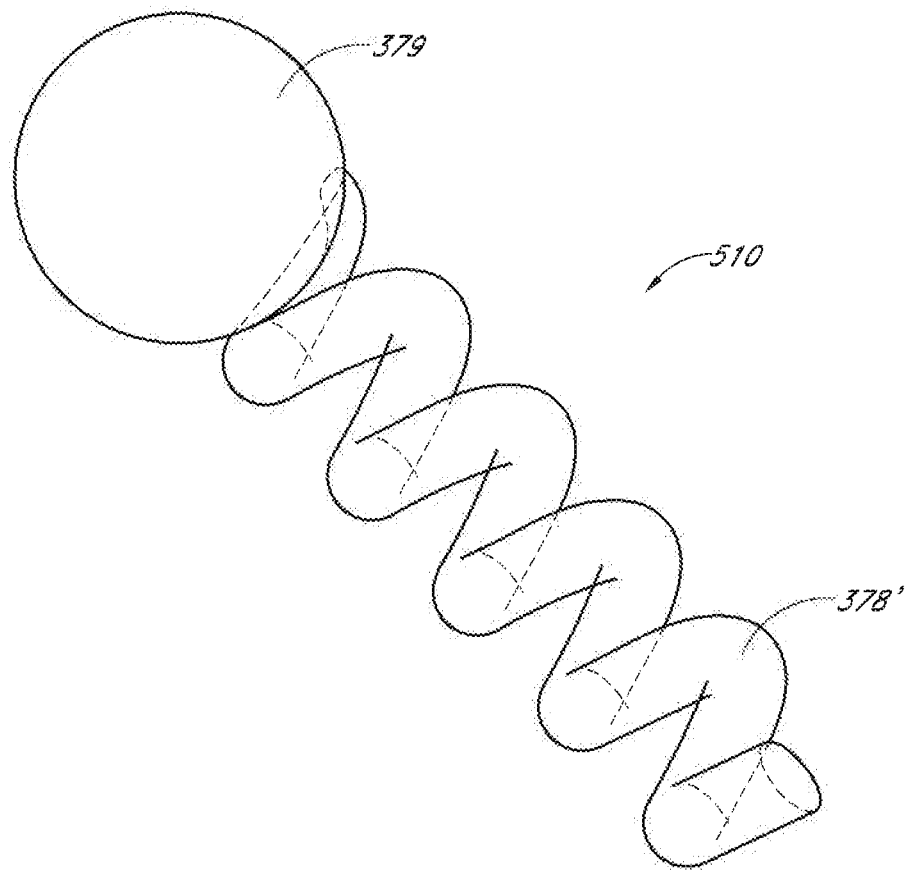
FIG. 51D illustrates a view of at least a non-linear portion of a strut of FIG. 51B.

FIG. 51D illustrates one embodiment of a fatigue-resistant terminal portion of a proximal and/or distal end of one, two, or more of the struts 374, 376, 378 illustrated in FIG. 51D. The terminal portion 51D may have a non-linear portion 378' and a head portion 379. The non-linear portion could be a coil with a helical, zig-zag, or any other generally non-linear shape to advantageously provide increased fatigue resistance for the struts. In some embodiments, at least a portion of the terminal portion 51D is embedded in an elastomer such as silicone, polycarbonate, urethane, or the like to further improve fatigue tolerance. In some embodiments, the terminal portion 51D may have a straight-line length that is less than 20%, 15%, 10%, 5%, or less of the strut. In some embodiments, the terminal portion 51D may have a straight-line length that is at least about 5%, 10%, 15%, 20%, 25%, or more of the length of the strut, or could even cover the entire length of one, two, or more struts 374, 376, 378 from first attachment zone 370 to second attachment zone 372 (e.g., a strut without a linear portion). Head portion 379 is operably connected to non-linear portion 378' and the portions may be integrally formed. The head portion 379 could be spherical, ovoid, square, rectangular, triangular, or a variety of other shapes. Head portion 379 is in turn operably connected to first attachment zone 370 and/or second attachment zone 372. In some embodiments, the head portion 379 is not attached to an attachment zone but rather terminates as a free end of one or more of the struts 374, 376, 378.

FIG. 51B is a side elevational view of the transvalvular band 366 of FIG. 51A, shown in a flat configuration. However, as has been discussed elsewhere herein, the transvalvular band will typically be provided with a curvature such that it advances the mitral valve leaflets in the direction of the ventricle and provides for physiologic coaptation.

FIG. 51C illustrates a perspective view of a transvalvular band 366 in a rolled-up configuration for delivery, similar to that illustrated in FIG. 50B. The band can be rolled in a variety of ways, such as capturing the band 366 at or near the center (near 363) and rolling it such that both ends are drawn inward as shown. In some embodiments, the band could be rolled up like a scroll, or folded into a "V", "W", or a variety of other shapes. In some embodiments, at least a portion of the band 366 resides within one or more slots 363 or movable jaw-like elements on the distal end 363 of a mandrel 367 or other elongate body within a delivery catheter. Actuation of the jaw-like elements to release the band 366, distal movement of a pusher tube, retraction of the mandrel 367' relative to another catheter, or other mechanism can be employed to deploy the band 366. In some embodiments, turning the mandrel a desired distance, such as about 90 degrees, can help facilitate unfurling of the band 366 for deployment.

Referring to FIGS. 52A-52C, there is illustrated a transvalvular band in accordance with the present invention having a tissue attachment system which may be adapted for either percutaneous or open surgical use. The transvalvular band comprises a central zone 368 carrying a first attachment zone 370 and a second attachment zone 372 as has been described.

A tissue anchor 390, such as a "t-tag" anchor includes a transverse element 392 and an elongate flexible suture 394. As used herein, the term "suture" is not limited to its normal definition, but also includes any of a wide variety of elongate flexible filaments, including polymeric, metal, combinations of both as well as monofilament and multifilament structures. Multifilament structures may be braided, woven, or otherwise configured, depending upon the desired performance.

The suture 394 is illustrated to extend through a first guide 396 in the second attachment zone 372. For simplicity, only a single anchoring system will be disclosed herein. However, it should be appreciated that the anchoring system may be utilized on both ends of the central zone 368, and more than one, such as two or three or more, anchors 390 may be utilized on each attachment zone.

The suture 394 is illustrated as extending through first guide 396, and then through a lock 398 which will be described below. The free end 402 of the suture 394 is further advanced through a second guide 400. Depending upon the intended use of the system, the free end 402 may extend proximally throughout the length of the deployment catheter, where it may be manipulated such as by proximal traction in order to tighten the second attachment zone 372 with respect to the transverse element 392. Thereafter, the free end 402 may be severed in the vicinity of the second attachment zone 372 or elsewhere.

Referring to FIG. 52C, details of the lock 398 may be seen. In general, the lock 398 includes an aperture 404 through which the suture 394 may extend. An engaging element 406 is exposed to the interior of the aperture, for permitting the suture to advance in a first direction through the aperture 404 but resist movement of the suture 394 in an opposite direction through the aperture 404. In the illustrated embodiment, the engaging element 406 is a sharpened point or spike configured to mechanically pierce or engage the suture 394.

The foregoing structure permits the free end 402 to be proximally withdrawn away from the second attachment zone 372 in a manner that draws the transverse element 392 closer to the second attachment zone 372. However, traction on the transverse element 392 causes the suture 394 to engage the engaging element 406, and prevents the transverse element 392 from pulling away from the second attachment zone 372.

Referring to FIG. 52D, illustrated is a suture 394 which can be looped through one, two, or more transverse elements 392 of anchors. The suture 394 looped through the anchor can function as a pulley, where appropriate traction on the suture 394 can tighten the anchors into place. Having a plurality of anchors as shown connected on one loop, such as, for example, 2, 3, 4, 5, or more anchors, can advantageously allow one cinching maneuver to tighten all of the anchors at once.

Referring back to FIG. 52A, an anchor deployment tool 408 is illustrated. Deployment tool 408 may comprise an elongate flexible wire having a proximal end 410 and a distal end 412. The deployment tool 408 may extend throughout the length of a percutaneous translumenal catheter, with the proximal end 410 exposed or attached to a control to allow axial reciprocal movement of the deployment tool 408. The distal end 412 is releasably positioned within an aperture 414 on a first end of the transverse element 392. A second end of the transverse element 392 is provided with a sharpened point 416.

In use, distal axial advance of the deployment tool 408 is utilized to drive the transverse element 392 into a target tissue, to a desired depth. Once the desired depth has been achieved, proximal retraction on the deployment tool 408 proximally retracts the distal end 412 out of the aperture 414, allowing removal of the deployment tool 408 but leaving the transverse element 392 behind within the target tissue. Proximal traction on the free end 402 of the suture 394 enables tightening of the transvalvular band with respect to the transverse element 392. Once a desired level of tightening has been achieved, releasing the free end 402 allows engaging element 406 to lock the suture 394 against further release, thereby holding the transvalvular band into position.

Figure 53:
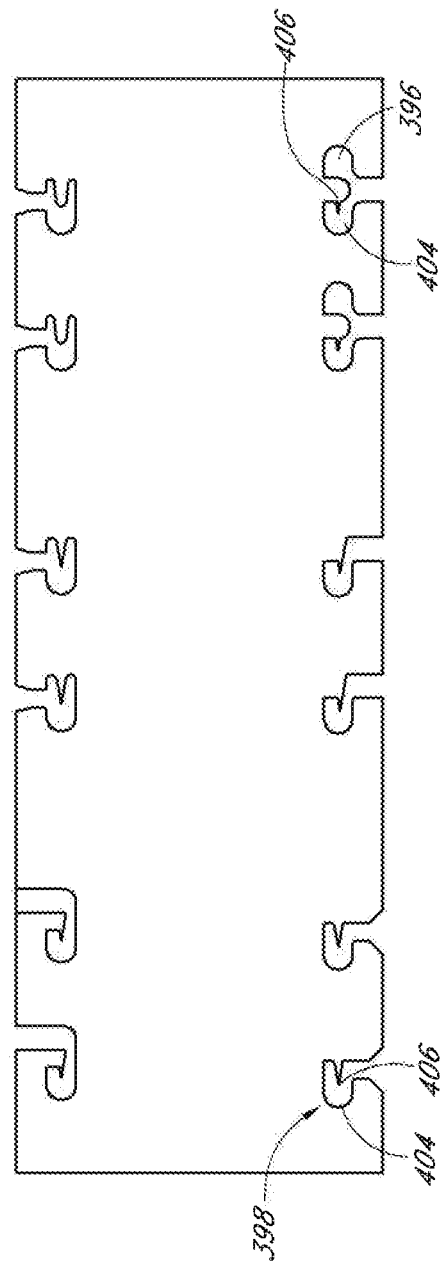
FIG. 53 is a side elevational perspective view of a transvalvular band in accordance with the present invention.

Although the lock 398 is illustrated as an enclosed aperture, alternative lock embodiments may involve access from a lateral edge of the implant. This permits side-loading of the suture into the lock, which may in some instances be desired over an enclosed aperture which requires end loading of the suture through the aperture. A variety of alternative side-loading lock configurations is illustrated in FIG. 53.

Figure 54:
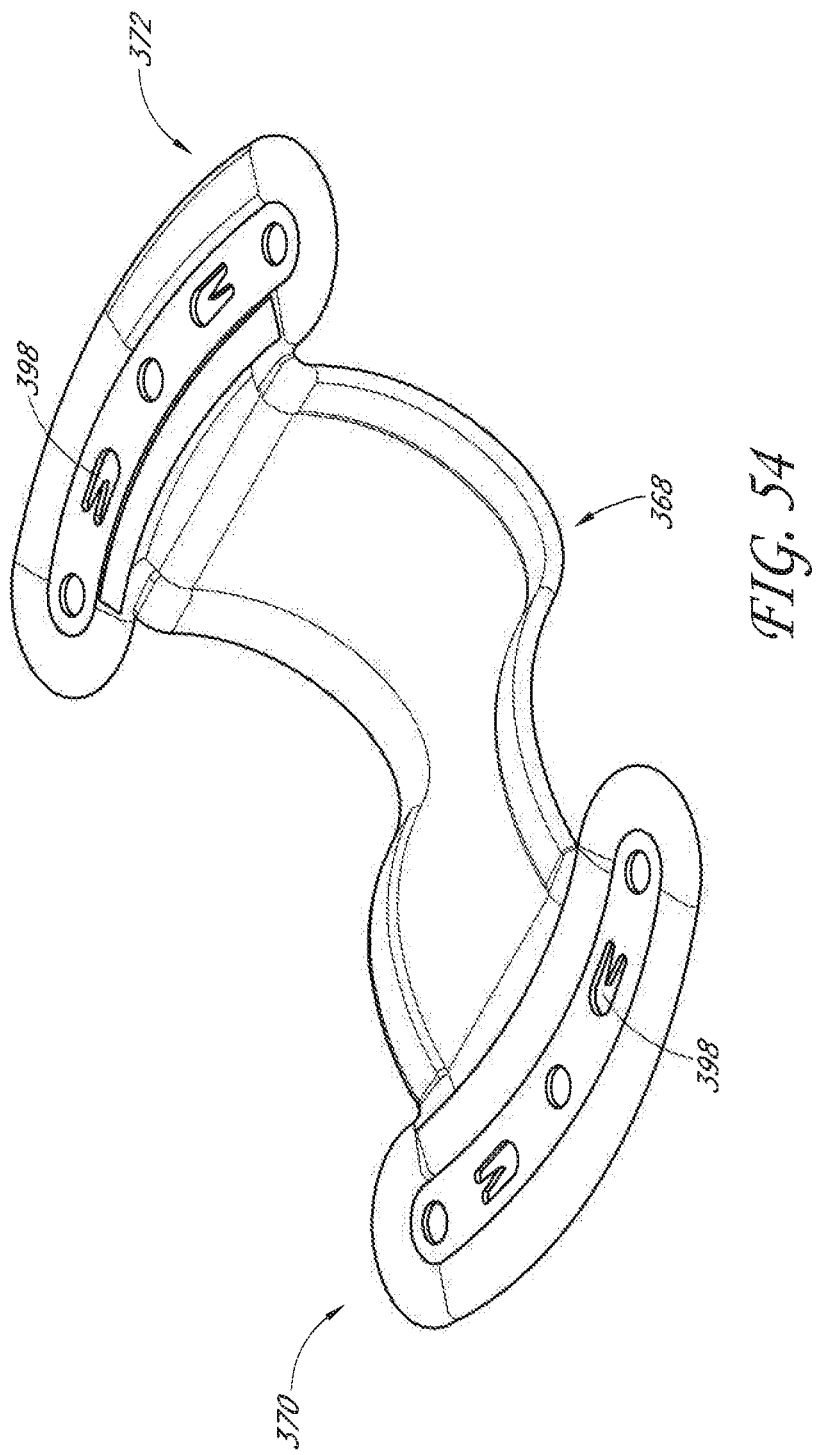
FIG. 54 is a schematic illustration of various suture lock configurations for use on transvalvular bands of the present invention.

Referring to FIG. 54, there is illustrated a perspective view of an alternate transvalvular band in accordance with the present invention. In this embodiment, the central section 368 is provided with an asymmetrical curvature, to provide asymmetrical support to the mitral valve leaflets. Along the width or central portion of the transvalvular band, this provides a contour mimicking the three-dimensional shape of the coapted mitral valve in a healthy native valve, and provides a physiologic analog thereby promoting correct anatomy during coaptation.

Figure 55:
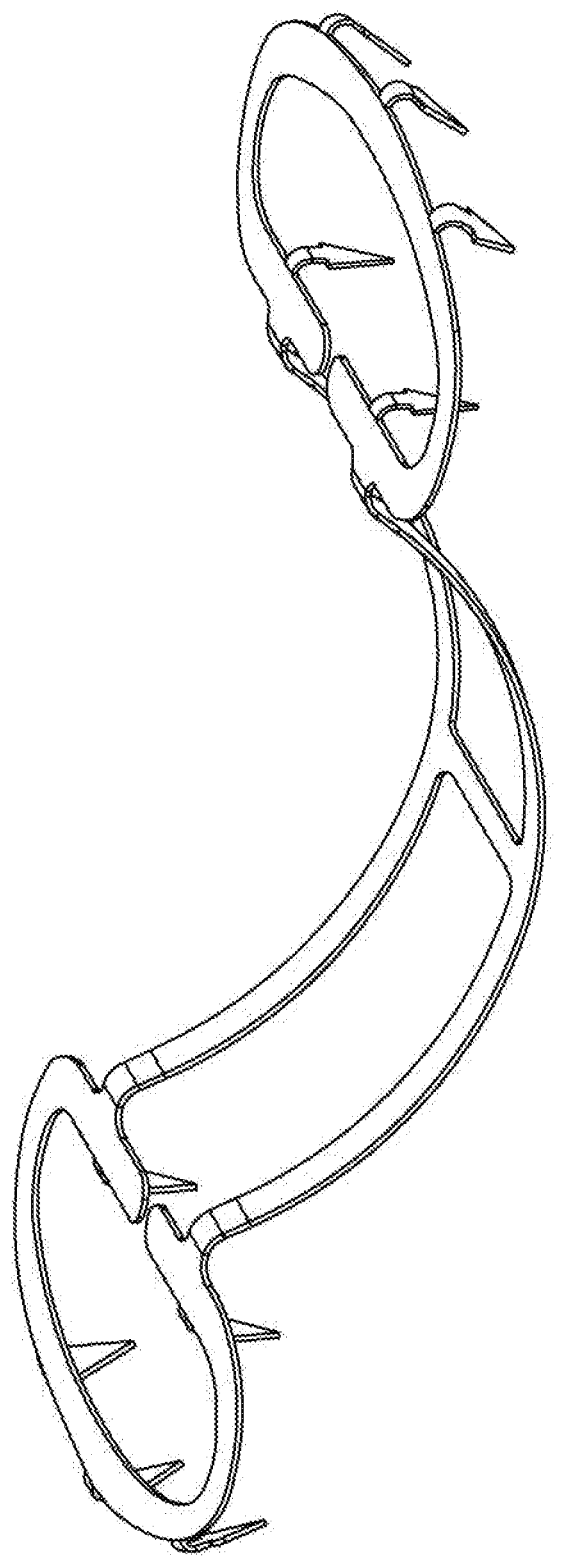
FIG. 55 is a side elevational perspective view of a transvalvular band, having barbed tissue anchors thereon.
Figure 56:
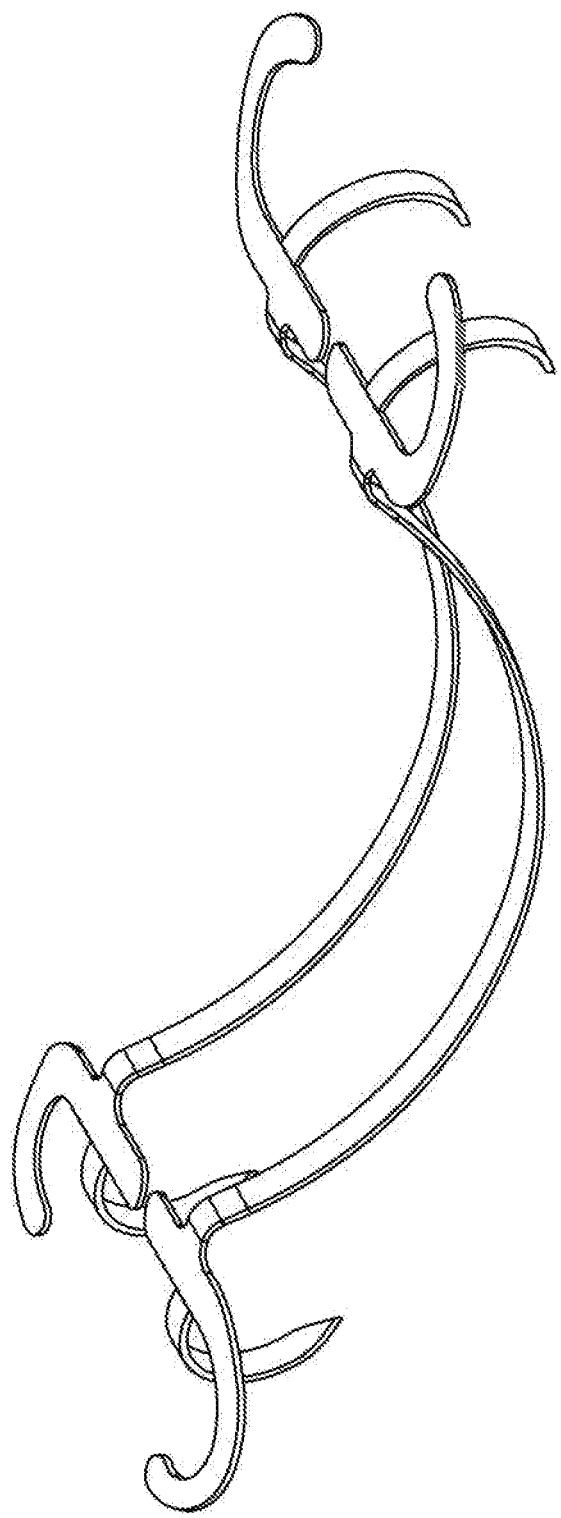
FIG. 56 is a side elevational perspective view of a transvalvular band in accordance with the present invention, having arcuate tissue anchors thereon.

FIGS. 55 and 56 illustrate alternative transvalvular bands in accordance with the present invention. In these embodiments, the attachment zones are provided with tissue anchors configured to pierce the tissue of the valve annulus. In general, the tissue anchors each comprise a pointed end, for penetrating tissue and a retention structure for resisting removal of the tissue anchor from the tissue. The retention element in FIG. 55 is in the form of a first or second barb or shoulder, as will be understood by those skilled in the art. The retention feature of the transvalvular band illustrated in FIG. 56 comprises an arcuate configuration for the tissue-piercing structure. Compression from the closure of the valve leaflets against the convex side of the central zone will tend to impart a circumferential force on the tissue anchors, advancing the distal point further in the direction of its own arcuate path. This construction tends to allow the natural forces of closure of the mitral valve to increase the retention of the tissue anchor within the adjacent tissue. In some embodiments, the barbs can be used as a primary anchor that can be crimped or otherwise secured in place. In other embodiment, the barbs could act as positioning features, to temporarily hold the band in place while verifying the position. The band could then be anchored in a secondary step, such as using a crimp, staple, suture, or other anchor as described herein. In some embodiments, the barbs can be self-locking upon penetration through tissue.

Figure 56A:
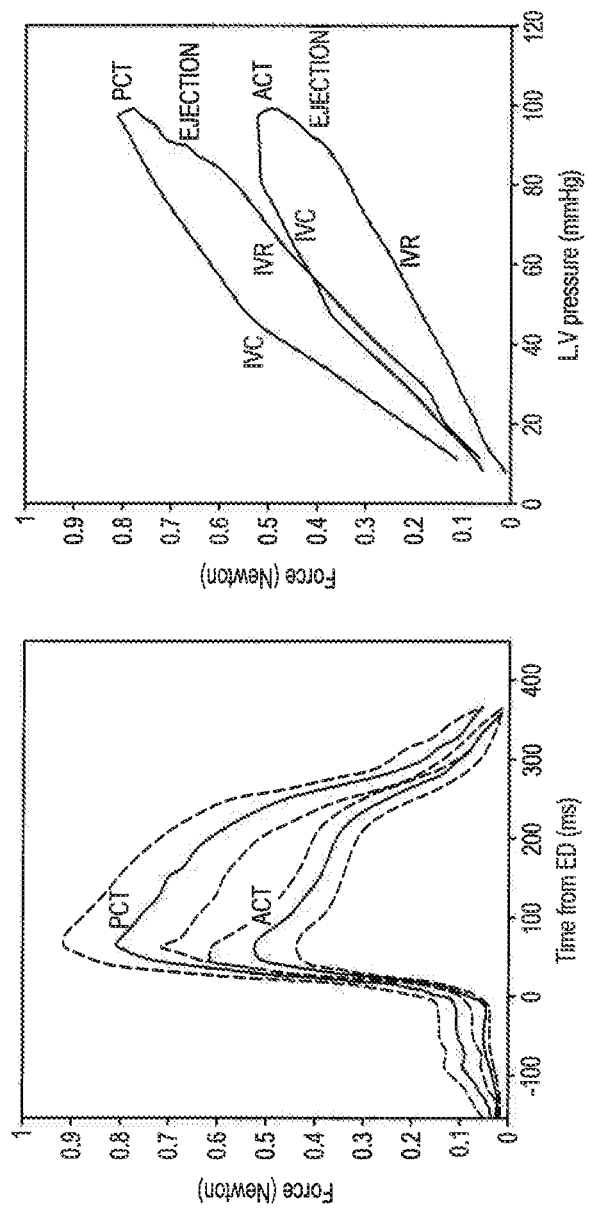
FIGS. 56A-B are graphs illustrating data regarding chordal physiologic force experiments.
Figure 56B:
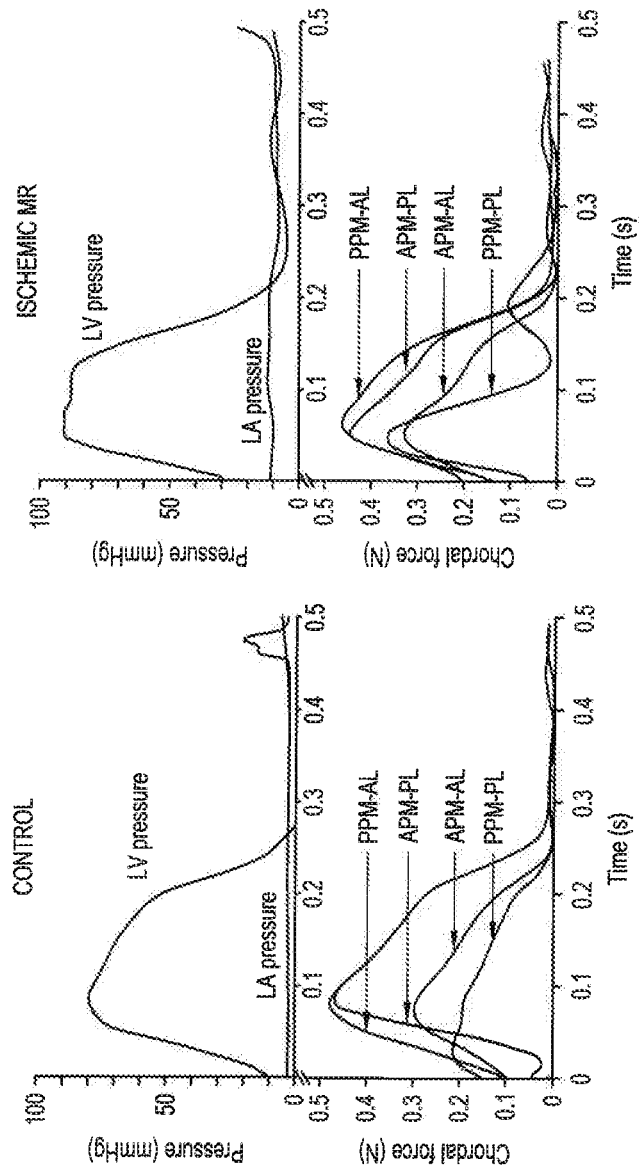

In some embodiments, disclosed is a transvalvular band that provides resistance to coaptation in the same manner as the chordae provides resistance to coaptation in a continuously nonlinear fashion, like a viscoelastic response. This band could have a configuration such as described and illustrated above, and could have material properties or additional features to provide non-linear resistance to coaptation. Such embodiments could retain a curvature mimicking the natural three dimensional surface of the coapted mitral valve yet could displace in the retrograde direction up to the anatomically correct plane of coaption when appropriate. The direction of displacement, for example, with respect to the mitral valve is better described in the atrial direction during systole to provide a cushioned impact for the valve leaflets as opposed to the leaflets striking a ridged implant structure and remodeling in a potentially deleterious fashion such as fibrosis or thinning around impact edges. FIG. 56A is reproduced from Nielsen et al, Circulation 2003; 108:486-491, *Influence of Anterior Mitral Leaflet Second-Order Chordae Tendineae on Left Ventricular Systolic Function*, which is hereby incorporated by reference in its entirety, illustrating a bilinear relationship between LV pressure and chordal tension during isovolumic contraction, a decrease in chordal tension despite high LV pressure during ejection, and an almost linear decline during isovolumic relaxation. FIG. 56B is reproduced from Nielsen et al, J Thorac Cardiovasc Surg 2005; 129:525-31, *Imbalanced chordal force distribution causes acute ischemic mitral regurgitation: Mechanistic insights from chordae tendineae force measurements in pigs*, which is incorporated by reference in its entirety. These figures demonstrate that chordae force with respect to time increases and then decays in a non-linear manner during systole. A band mimicking this performance could benefit the valvular surface as it returns its coaptive forces to a near normal state. In some embodiments, a band could cushion or physiologically reduce or prevent physical stress caused by repetitive contact with the coaptive leaflet surfaces. The band could accomplish this by virtue of construction such as chambered struts that may or may not be filled with a media such as a fluid. These chambers would be enclosed and impermeable or substantially impermeable to blood or blood component penetration within a lifetime. Another method of cushioned coaption would be a device that allows some flexing during coaption. This flexibility could be designed based upon strut material, thickness, width, inferior and superior cross-section such as a ripple, or encapsulation material such as an elastomer or elastomeric foam. The foam material could be sealed by an exterior polymer of equal overall flexibility. Additional embodiments would be coils (such as illustrated in FIG. 51D above) or coils within coils to produce unique nonlinear displacement signatures or tubes such as Nitinol laser cut tubes that could optionally be filled with a polymer. Yet another embodiment would include struts that loop towards the ventricle crossing itself. This loop would also create this nonlinear resistance to coaption by its spring force. In other embodiments, the band can proceed down to the chordae and devices can be adapted to shorten or augment the chordae to achieve natural physiology. Devices of this manner can be, for example, crimped bands with elastomer bodies between the crimped bands. The elastomeric bodies would replicate the deficient portion of the chordae to mimic the correct force curve during coaptation. This may provide enough benefit in some grades of the disease so as to provide palliative care or resolve it.

Any of a wide variety of specific tissue anchor constructions may be utilized in combination with the transvalvular band of the present invention. In addition, a variety of features have been described as illustrative in connection with a variety of implementations of the invention. Any of the features described above, may be recombined with any other of the embodiments disclosed herein, without departing from the present invention, as should be apparent to those of skill in the art.

Figure 57:
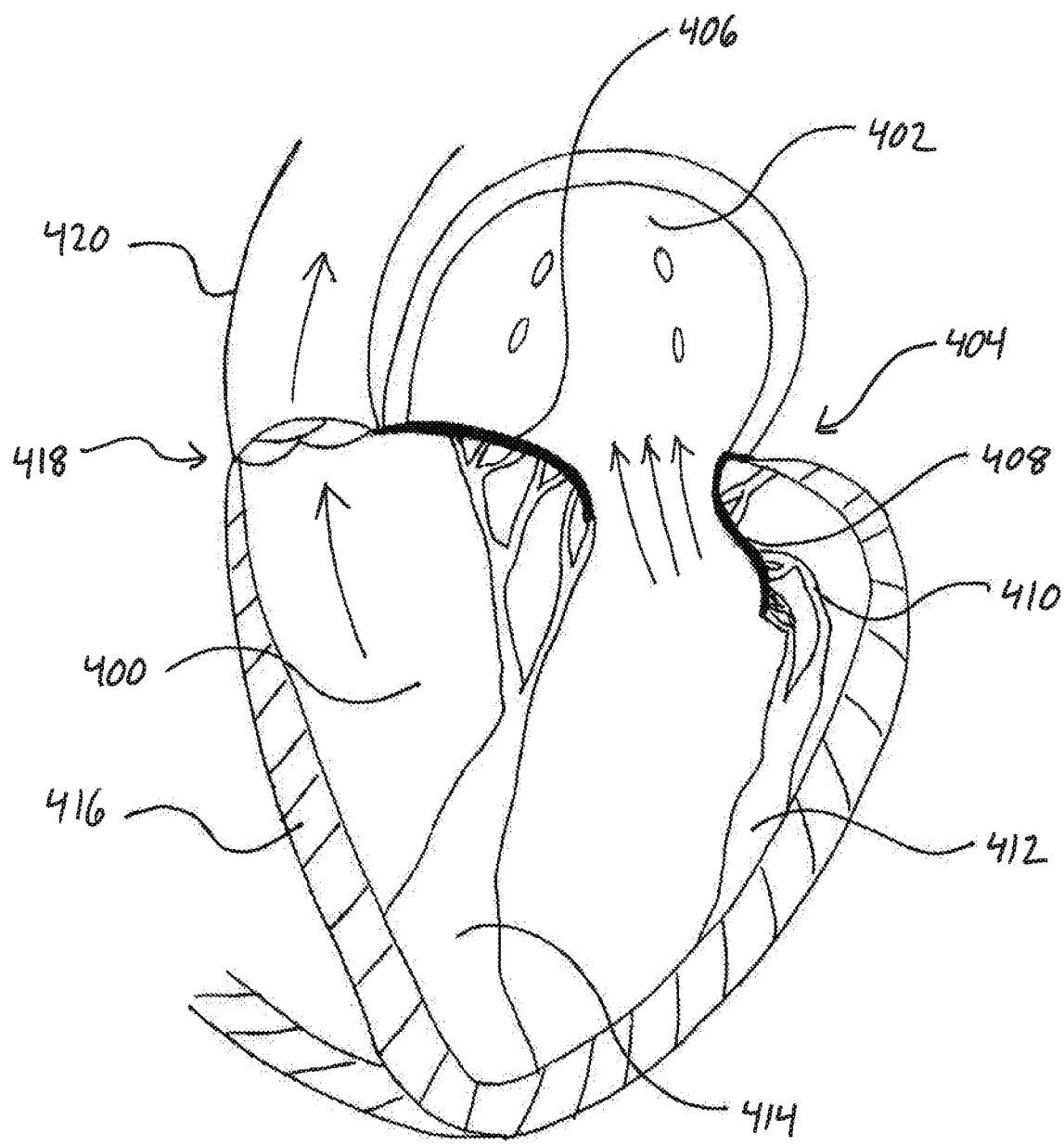
FIG. 57 Illustrates a dilated mitral annulus with restricted posterior leaflet motion due to distortion of posterior papillary muscle due to enlargement of left ventricular chamber in ischemic or dilated cardiomyopathy. This shows malcoaptation of leaflets causing central mitral regurgitation.

Referring to FIG. 57, there is illustrated a dilated mitral annulus with restricted posterior leaflet motion due to distortion of the posterior papillary muscles due to enlargement of the left ventricular chamber. This condition occurs in ischemic or dilated cardiomyopathy. The schematically illustrated result is malcoaption of leaflets, causing central mitral regurgitation.

FIG. 57 schematically illustrates a heart, in which left ventricle 400 is separated from left atrium 402 by a mitral valve 406. The mitral valve 406 comprises an annulus, anterior leaflet 406 and posterior leaflet 408. Posterior leaflet 408 is distorted due to expansion of the ventricular wall pulling the posterior leaflet via marginal chordae 410, which connect to the posterior papillary muscle 412. The anterior leaflet 406 is properly restrained by the anterior papillary muscle 414. Also illustrated are the intraventricular septum 416, aortic valve 418, and the aorta 420.

Figure 58:
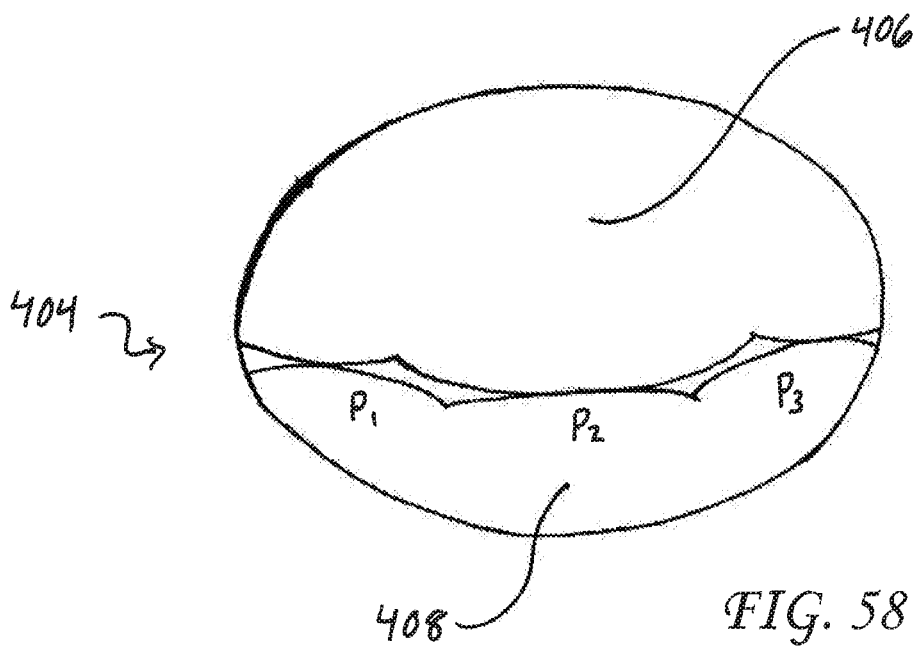
FIG. 58 is a view of the normal mitral annulus during systole looking from the left atrium to the left ventricle.
Figure 59:
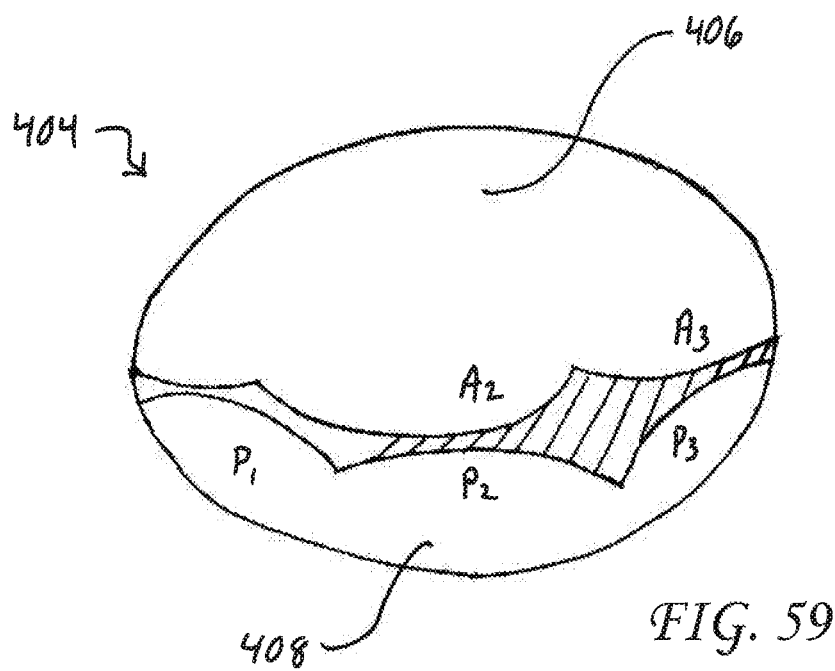
FIG. 59 is a view of the mitral valve in ischemic and dilated cardiomyopathy in systole looking from the left atrium to the left ventricle. This shows central mitral regurgitation in the region of P2 P3 scallops of the posterior leaflet.

Referring to FIG. 58, there is illustrated a schematic view of the normal mitral annulus during systole, looking from the left atrium in the direction of the left ventricle. FIG. 59 illustrates a mitral valve in ischemic and dilated cardiomyopathy, in systole, looking from the left atrium in the direction of the left ventricle. The illustration of FIG. 59 shows central mitral regurgitation in the region of the P2 and P3 scallops of the posterior leaflet.

Mitral regurgitation is the frequent cause of severe congestive heart failure in many patients with progressive left ventricular chamber enlargement due to primary dilated or ischemic cardiomyopathy. Mechanism of mitral regurgitation is due to mitral annular dilatation casing malcoaptation of the mitral valve leaflets during ventricular systole (FIG. 57, FIG. 59), and distortion of papillary muscles (to which mitral valve leaflets are attached) due to left ventricular chamber enlargement which causes restricted leaflet motion. This process frequently affects the posterior leaflet of mitral valve (FIG. 57, FIG. 59)

Current surgical treatment consists of mitral annuloplasty and many complex subvalvular procedures i.e. papillary muscle repositioning and cutting only the strut chordae near the base of the leaflet and the left ventricle. These open heart surgical procedures are time consuming, invasive and require cardiopulmonary bypass. They have not yielded satisfactory results because of the progressive enlargement of the left ventricle and further distortion of attached leaflet chordae papillary muscle apparatus. For the same reason transcatheter annuloplasty and edge to edge repair of mitral valve leaflets have not been very successful.

In accordance with aspects of the present invention described above, there has been provided a simple transvalvular intraannular band device for treating mitral regurgitation due to mitral valve prolapse where there is excessive motion of the valve leaflets above the plane of the annulus. Implantation may be accomplished surgically or transvascularly. But in certain patients, continued enlargement of the left ventricular chamber cooperates with intact chordae to produce or progress regurgitation.

Figure 61:
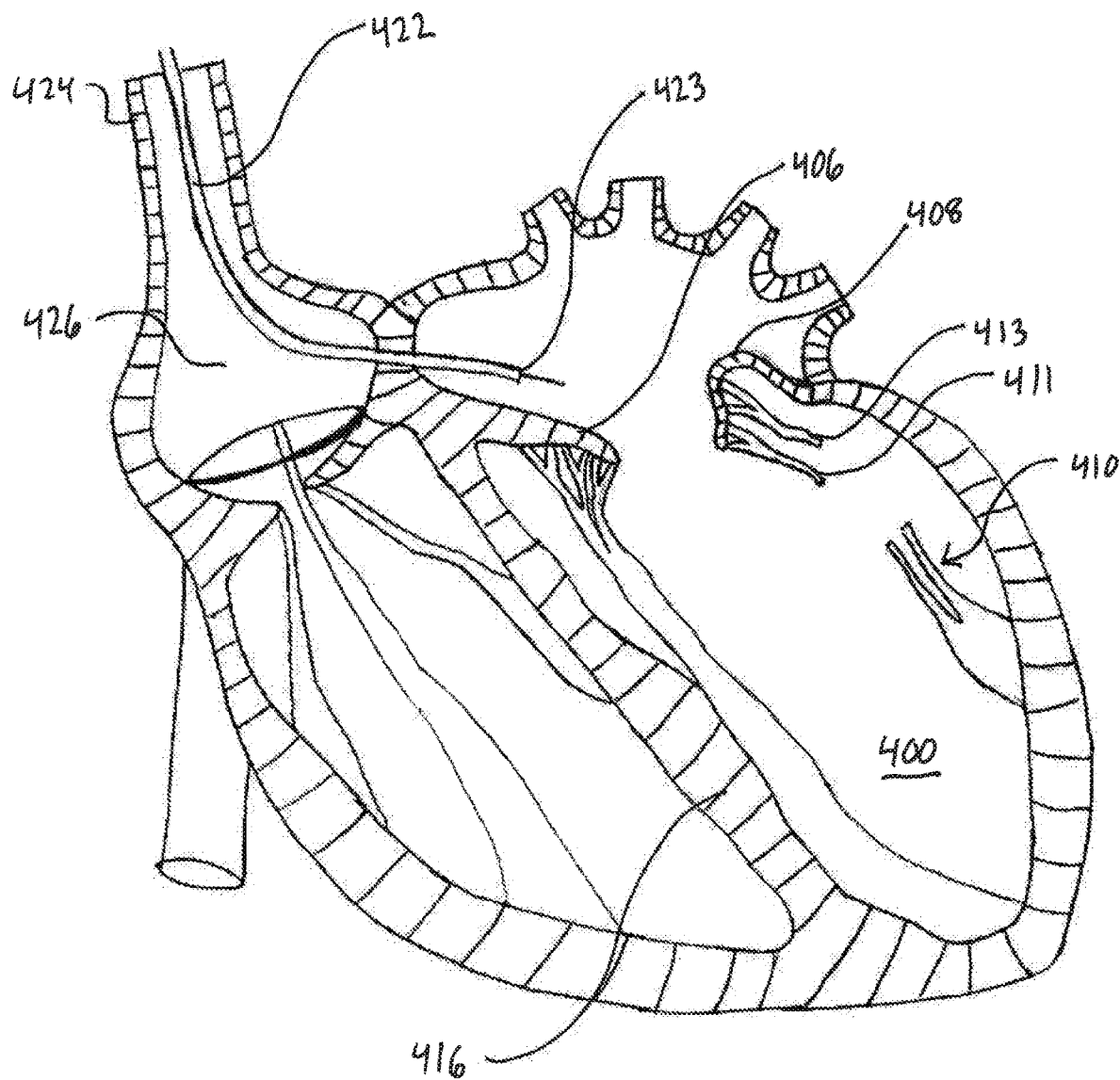
FIG. 61 illustrates a transseptal catheter with the cutting instrument pulled back into the left atrium showing the cut marginal chordae of the posterior leaflet of the mitral valve with prolapsed posterior mitral valve leaflet into the left atrium.

Thus, in accordance with a further aspect of the present invention, there are provided methods and devices for treatment of ischemic and dilated cardiomyopathy patients with mitral regurgitation. In accordance with the methods, the main marginal chordae of the posterior mitral valve leaflets are cut, preferably in the region of P2 P3 scallops of the valve then the posterior leaflet will be allowed to prolapse into the left atrium above the plane of the mitral annulus (FIG. 61). Then this prolapse will be treated by inserting one of the transvalvular intraannular bands in the mitral annulus (FIG. 62), as has been described elsewhere herein.

Figure 60:
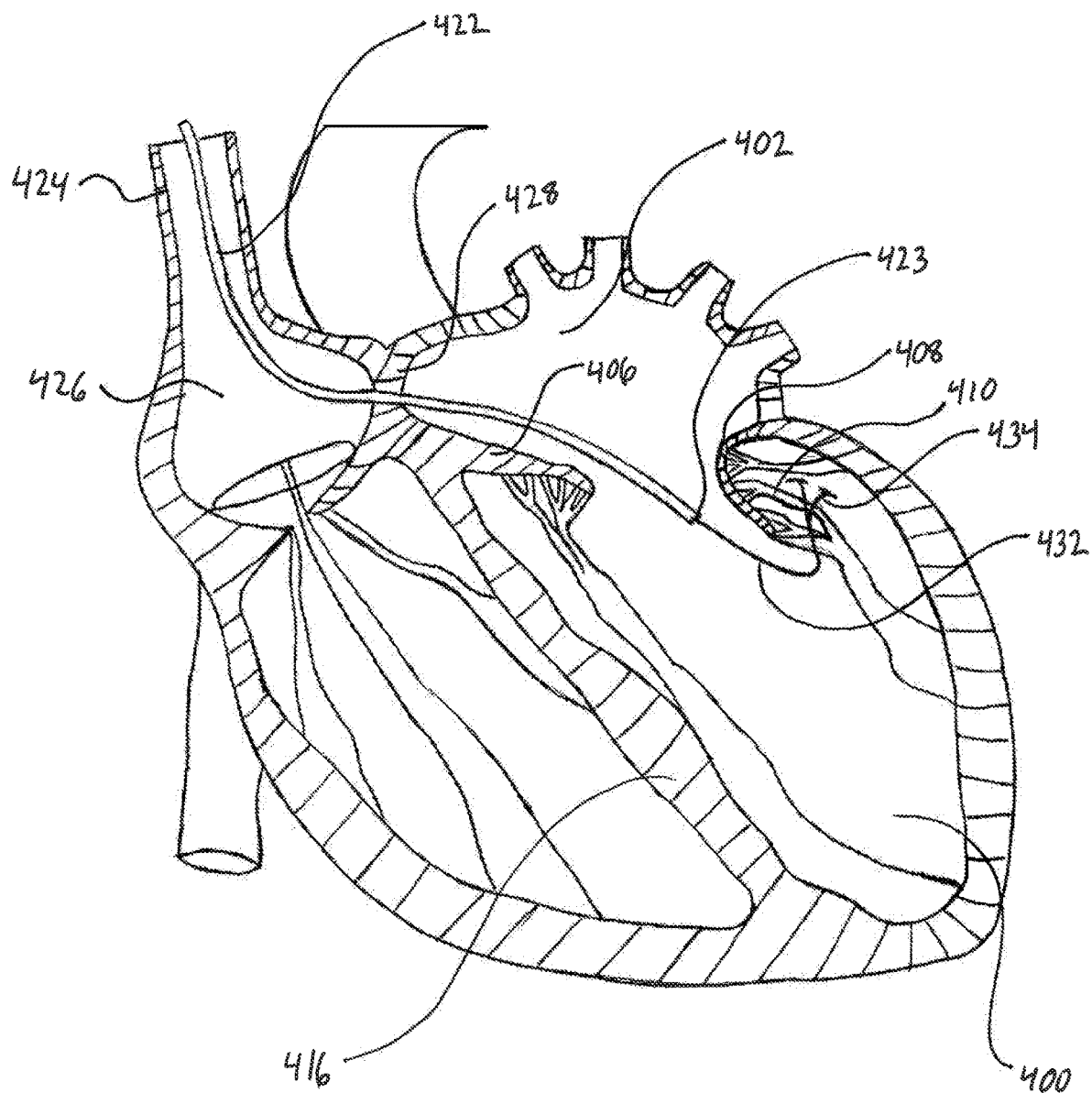
FIG. 60 illustrates a transseptal catheter with cutting instrument engaged into the marginal chordae of the posterior mitral valve leaflet in ischemic dilated cardiomyopathy.
Figure 62:
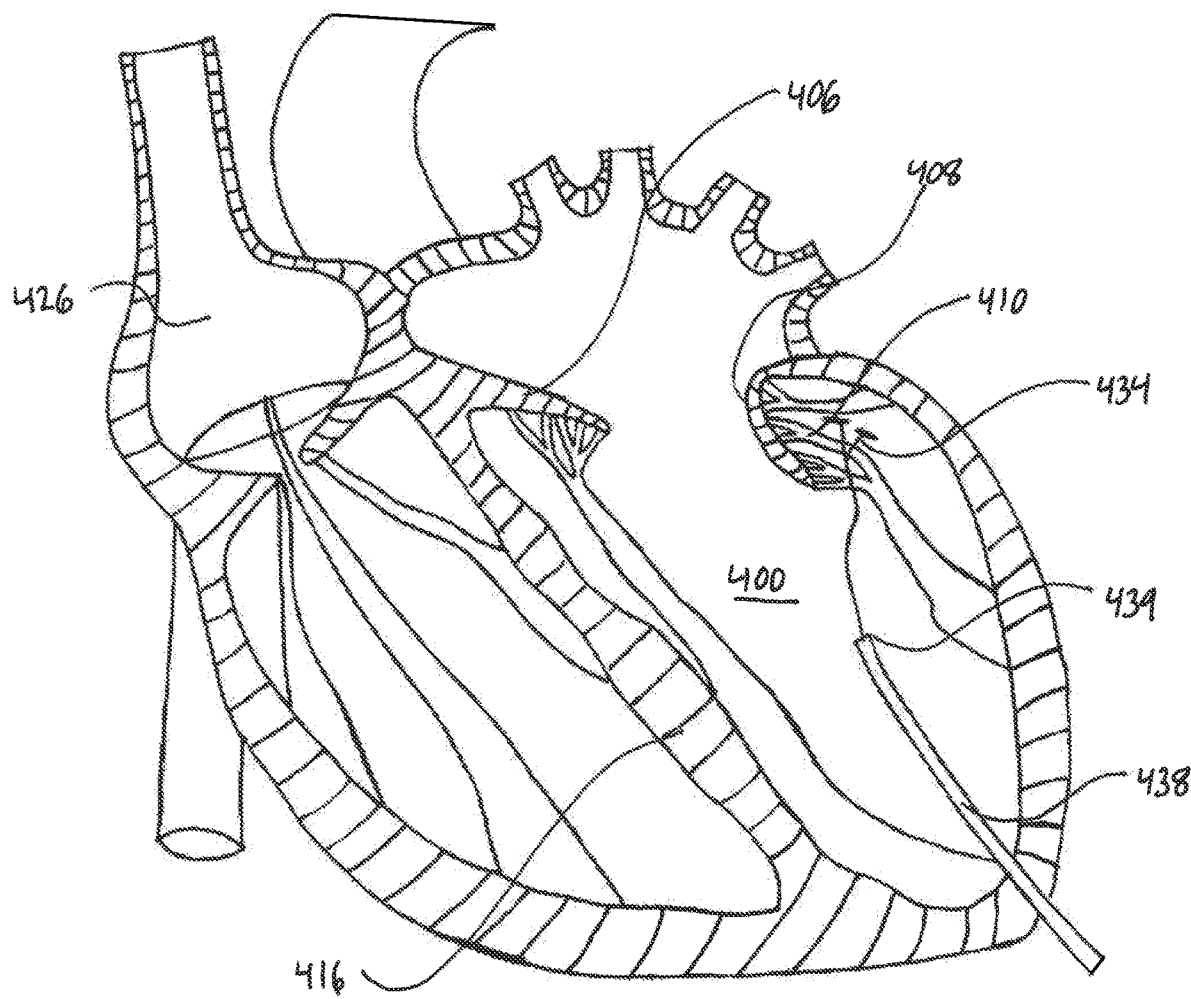
FIG. 62 illustrates a transapical catheter with chordae cutting instrument engaged in the marginal chordae of the posterior leaflet of the mitral valve.

This procedure can be accomplished through a surgically open, minimally invasive approach with a very short operative time. The chordal cutting and the band deployment could be done percutaneously by a transcatheter technique with access via the femoral vein into interatrial septum entering the left atrium and left ventricle (FIGS. 60-61). Alternatively, this could be done from femoral artery approach into the ascending aorta and through the aortic valve for cutting the chordae and deployment of the band. Another access could be through transapical approach from the left ventricular apex (FIG. 62). Any two or all of these percutaneous approaches could be also combined.

The chordae cutting instruments vary from microscissors, microknife or other sharpened edge based cutting instruments, to cryoablation, ultrasonic, radiofrequency, microwave, laser energies or other cutting techniques known in the art.

Thus, referring to FIG. 60, a transseptal catheter 422 has been placed across the septum 428 between the right atrium 426 and left atrium 402, via a superior vena cava 424 access. A distal end 423 of the transseptal catheter 422 is positioned in the vicinity of the mitral valve. A cord cutting instrument 430 is advanced through the transseptal catheter and out the distal end 423, to selectively sever one or two or four or more of the marginal chordae 410. The cord cutting instrument 430 comprises an elongate flexible body 432 having a proximal end with a cutter control thereon (not illustrated) and a distal end with a tissue cutter 434. The control may be varied considerably, depending upon the nature of the cord cutting modality. For example, mechanical knobs, levers and sliders may be utilized to control mechanical cutters such as scissors or knives. Electrical switch, button or knob may be utilized to control other energy based cutting modalities, such as radio frequency, microwave, laser or ultrasound.

Figure 63:
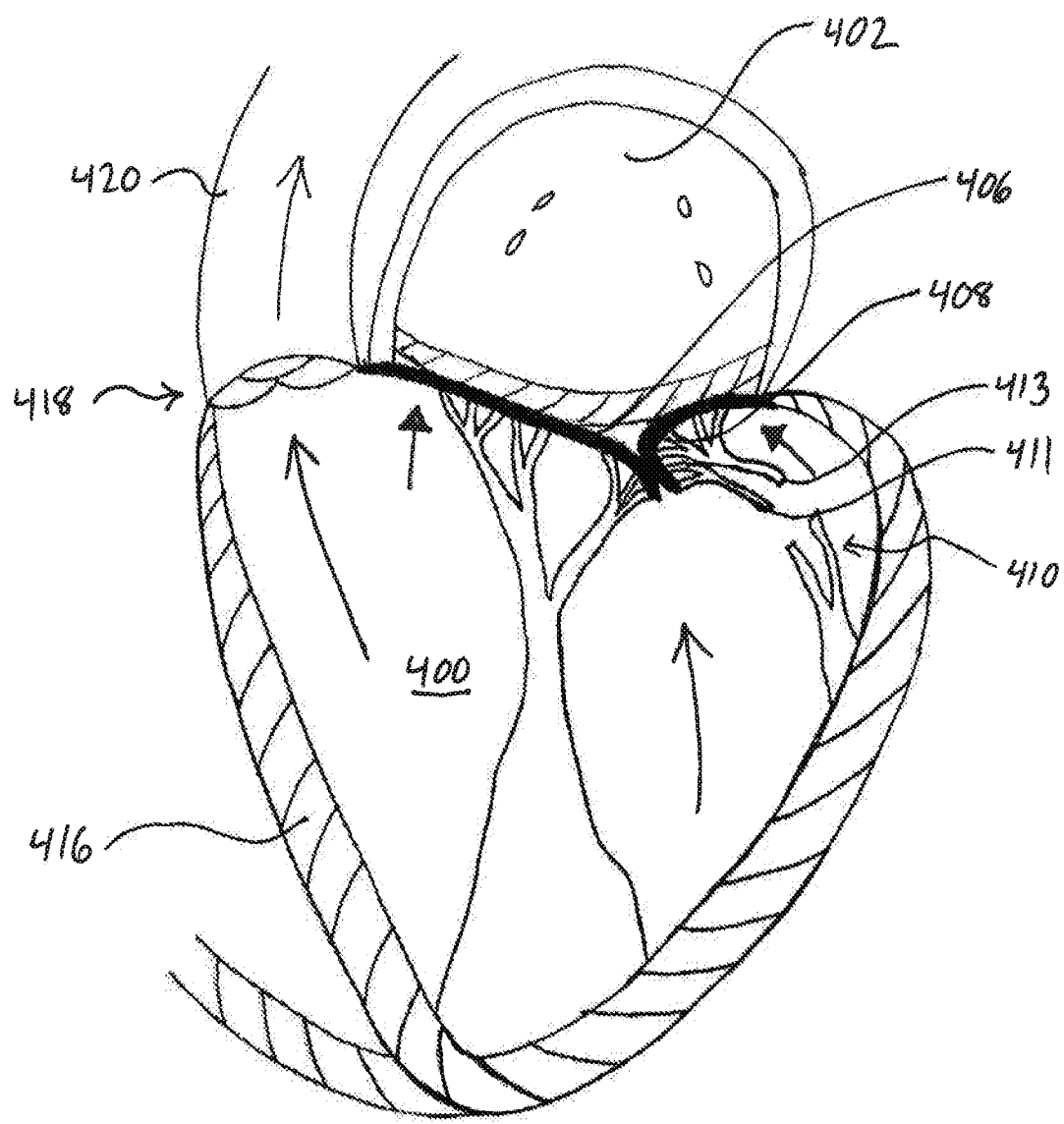
FIG. 63 illustrates the transmitral annular band in place across the mitral annulus, in systole, preventing the prolapse of the posterior leaflet into the left atrium. The cut marginal chordae are shown. The coaptation of the leaflet shown with no regurgitation into the left atrium during systole.

Once sufficient marginal chordae have been severed to release the posterior leaflet from the constraint imposed by the dilated cardiomyopathy, the posterior leaflet is freed to prolapse as illustrated in FIG. 61. However, either prior to severing the marginal chordae or following the severing of the marginal chordae, a mitral valve leaflet support in the form of any of the transvalvular bands disclosed previously herein is positioned across the mitral valve, as schematically illustrated in FIG. 63. The transmitral band (e.g., transvalvular) prevents prolapse of the posterior leaflet into the left atrium, despite the cut marginal chordae, and the cut marginal chordae enables complete coaption of the leaflets shown with no regurgitation into the left atrium during systole.

Referring to FIG. 62, there is illustrated an alternative access to the mitral valve, via a transapical catheter 438. A distal end 439 of the transapical catheter 438 is positioned within the left ventricle. A cord cutting instrument 430 is advanced therethrough, such that an elongate flexible body 432 carries a tissue cutter 434 into the marginal chordae 410. Any of a variety of tissue cutting tips may be utilized for tissue cutter 434 as has been described elsewhere herein. The marginal chordae may be severed via transapical approach either prior to or following implantation of the transvalvular band described elsewhere herein.

Although the foregoing description has been primarily in the context of severing the marginal chordae to release the posterior leaflet, that is merely an example of the invention which involves manipulating the heart to release the leaflet from a constraint imposed by a heart condition, and then treating the resulting prolapse by implantation of a leaflet support. Manipulation can be any procedure that increases the range of travel of the constrained leaflet, with complete severing of at least one marginal chordae being a convenient technique. Manipulations that stretch the marginal chordae, or which sever or stretch the corresponding papillary muscle may alternatively be used. A portion or all of the severed chordae or papillary muscle may be removed, or left in situ as illustrated in FIGS. 61 and 63.

While the foregoing detailed description has set forth several exemplary embodiments of the apparatus and methods of the present invention, it should be understood that the above description is illustrative only and is not limiting of the disclosed invention. It will be appreciated that the specific dimensions and configurations disclosed can differ from those described above, and that the methods described can be used within any biological conduit within the body.

What is claimed is:

1. A method, comprising:
providing an intraannular band dimensioned for attachment within a valve annulus, wherein the intraannular band comprises a body having a first end, a second end, and a convex shaped central portion, wherein the body further comprises first and second anchoring portions, the first anchoring portion located proximate the first end and comprising an opening, the second anchoring portion located proximate the second end; and
attaching the intraannular band within the valve annulus such that the convex shaped central portion extends transversely across a coaptive edge formed by valve leaflets, wherein attaching the intraannular band comprising passing an anchor through the opening formed in the intraannular band in a first direction, wherein the anchor resists retraction in a second, opposite direction, back through the opening in the intraannular band.

2. The method as in claim 1, further comprising elevating a position of the coaptive edge by at least about 4 mm.

3. The method as in claim 1, further comprising elevating a position of the coaptive edge.

4. The method as in claim 1, wherein the convex shaped central portion comprises a narrowed portion configured to reduce resistance to blood flow.

5. The method as in claim 1, wherein the body further comprises first and second shoulder portions, the first shoulder portion located between the first anchoring portion and the convex shaped central portion, the second shoulder portion located between the second anchoring portion and the convex shaped central portion, wherein part of the convex shaped central portion is narrower than the first and second shoulder portions to reduce resistance to blood flow, and wherein part of the first and second shoulder portions are narrower than the first and second anchoring portions to reduce resistance to blood flow.

6. The method as in claim 1, wherein the body further comprises first and second shoulder portions, the first shoulder portion located proximate the first anchoring portion and the convex shaped central portion, the second shoulder portion located proximate the second anchoring portion and the convex shaped central portion.

7. The method as in claim 6, wherein the first and second shoulder portions taper from a first width to a second width, the second width less than the first width.

8. A method, comprising:
implanting in an annulus an intraannular band comprising a body having a first end, a first anchoring portion located proximate the first end, a second end, a second anchoring portion located proximate the second end, and a convex shaped central portion, wherein the convex shaped central portion is displaced out of a reference plane containing the first and second ends, wherein the body further comprises first and second shoulder portions, the first shoulder portion located between the first anchoring portion and the convex shaped central portion, the second shoulder portion located between the second anchoring portion and the convex shaped central portion, wherein part of the convex shaped central portion is narrower than the first and second shoulder portions to reduce resistance to blood flow, and wherein part of the first and second shoulder portions are narrower than the first and second anchoring portions to reduce resistance to blood flow;
attaching the first anchoring portion to a first portion of tissue; and attaching the second anchoring portion to a second portion of tissue such that the intraannular band extends transversely across a coaptive edge formed by the closure of valve leaflets,
wherein attaching the first and second anchoring portions comprises passing a first anchor and a second anchor through the first anchoring portion and the second anchoring portion, respectively, wherein the first anchor and the second anchor pass through the corresponding anchoring portion, but resist retraction back through the corresponding anchoring portion.

9. The method as in claim 8, wherein the first and second shoulder portions taper from a first width to a second width, the second width less than the first width.

10. The method as in claim 8, further comprising elevating a position of the coaptive edge.

11. A method, comprising:
providing an intraannular band dimensioned for attachment within an intraannular plane of a heart valve annulus, wherein the intraannular band comprises a body having a first end, a second end, and a convex shaped central portion; and
attaching the intraannular band within the intraannular plane of the heart valve annulus such that the convex shaped central portion extends out of a reference plane including a portion of the first and second ends, such that the convex shaped central portion extends transversely across a coaptive edge formed by two or three valve leaflets,
wherein attaching the intraannular band comprises passing at least two anchors through the intraannular band and into tissue of the heart valve annulus, wherein at least one anchor resists retraction.

12. The method as in claim 11, wherein the body further comprises first and second anchoring portions and first and second shoulder portions, the first anchoring portion located proximate the first end, the second anchoring portion located proximate the second end, the first shoulder portion located proximate the first anchoring portion and the convex shaped central portion, the second shoulder portion located proximate the second anchoring portion and the convex shaped central portion, wherein the convex shaped central portion comprises a narrowed portion narrower than part of the first and second shoulder portions to reduce resistance to blood flow, and wherein the first and second shoulder portions comprise a narrowed portion narrower than part of the first and second anchoring portions to reduce resistance to blood flow.

13. The method as in claim 12, wherein the first and second shoulder portions taper from a first width to a second width, the second width less than the first width.

14. The method as in claim 11, wherein the convex shaped central portion comprises at least one strut.

15. The method as in claim 11, wherein the heart valve annulus is a mitral valve annulus.

16. The method as in claim 11, wherein the heart valve annulus is an aortic valve annulus.

17. The method as in claim 11, wherein the cardiac valve is a tricuspid valve.

* * * * *